US008535726B2

(12) United States Patent
Dai et al.

(10) Patent No.: US 8,535,726 B2
(45) Date of Patent: Sep. 17, 2013

(54) SUPRAMOLECULAR FUNCTIONALIZATION OF GRAPHITIC NANOPARTICLES FOR DRUG DELIVERY

(75) Inventors: Hongjie Dai, Cupertino, CA (US); Zhuang Liu, Stanford, CA (US); Xiaolin Li, Menlo Park, CA (US); Xiaoming Sun, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 796 days.

(21) Appl. No.: 12/178,891

(22) Filed: Jul. 24, 2008

(65) Prior Publication Data
US 2009/0087493 A1 Apr. 2, 2009

Related U.S. Application Data

(60) Provisional application No. 60/962,192, filed on Jul. 27, 2007.

(51) Int. Cl.
*A61K 9/16* (2006.01)
*A61K 9/50* (2006.01)

(52) U.S. Cl.
USPC .......................................... 424/490; 977/742

(58) Field of Classification Search
USPC ....................................................... 424/490
See application file for complete search history.

(56) References Cited

U.S. PATENT DOCUMENTS

| | | | |
|---|---|---|---|
| 6,187,823 B1 | 2/2001 | Haddon et al. | |
| 6,896,864 B2 | 5/2005 | Clarke | |
| 7,009,033 B2 * | 3/2006 | Varshney et al. | 528/421 |
| 7,070,810 B2 | 7/2006 | Hirsch et al. | |
| 7,731,929 B2 | 6/2010 | Clarke | |
| 7,968,073 B2 | 6/2011 | Clarke et al. | |
| 2002/0150524 A1 | 10/2002 | Smalley et al. | |
| 2002/0179434 A1 | 12/2002 | Dai et al. | |
| 2003/0012723 A1 | 1/2003 | Clarke | |
| 2005/0031526 A1 | 2/2005 | Clarke | |
| 2005/0100960 A1 | 5/2005 | Dai et al. | |
| 2005/0229335 A1 | 10/2005 | Huang et al. | |
| 2006/0018826 A1 | 1/2006 | Unger et al. | |
| 2006/0199770 A1 | 9/2006 | Bianco et al. | |
| 2006/0275371 A1 | 12/2006 | Dai et al. | |
| 2007/0117109 A1 | 5/2007 | Rothemund | |

FOREIGN PATENT DOCUMENTS

| | | |
|---|---|---|
| EP | 1605265 A1 | 12/2005 |
| WO | 02095099 A1 | 11/2002 |
| WO | 2004089818 A1 | 10/2004 |

OTHER PUBLICATIONS

Kam et al., "Carbon Nanotubes as Intracellular Transporters for Proteins and DNA: An Investigation of the Uptake Mechanism and Pathway," Angew. Chem., 2006, vol. 118, pp. 591-595.*
Chen et al., "Noncovalent functionalization of carbon nanotubes for highly specific electronic biosensors," PNAS, 2003, vol. 100, pp. 4984-4989.*
Kam, "Biological Applications of Carbon Nanotubes: Paving the Way to Nanotube-based Delivery Vehicles and Therapies for Living Systems," Stanford University dissertation; May 2006; ProQuest Information and Learning Company.*
Chen et al., "Noncovalent Sidewall Functionalization of Single-Walled Carbon Nanotubes for Protein Immobilization," J. Am. Chem. Soc., 2001, vol. 123, pp. 3838-3839.*
Kam, et al., "Nanotube Molecular Transporters: Internalization of Carbon Nanotube-Protein Conjugates into Mammalian Cells," J. Am. Chem. Soc., 2004, vol. 126, No. 22, 6850-6851.
Kam, et al., "Carbon Nanotubes as Intracellular Transporters: Generality and Biological Functionality," J. Am. Chem., 2005, vol. 127, 6021-6026.
Kam, et al., "Functionalization of Carbon Nanotubes via Cleavable Disulfide Bonds for Efficient Intracellular Delivery of siRNA and Potent Gene Silencing," J. Am. Chem. Soc., 2005, vol. 127, 12492-12493.
Won Seok Seo, et al., "FeCo/graphitic-shell nanocrystals as advanced magnetic-resonance-imaging and near-infrared agents," Nature Materials, 2006, vol. 5, 971.
Zhang Liu, et al., "siRNA Delivery into Human T Cells and Primary Cells with Carbon-Nanotube Transporters," Angew. Chem. Int. Ed., 2007, vol. 46, 2023-2027.
Siqun Wang, et al., "Peptides with selective affinity for carbon nanotubes," Nature Materials, Mar. 2003, vol. 2, 196-200.
PCT International Search Report mailed Oct. 10, 2008.
Nadine Wong Shi Kam, et al., "Carbon nanotubes as multifunctional biological transporters and near-infrared agents for selective cancer cell destruction," PNAS, Aug. 16, 2005, vol. 102, No. 33, 11600-11605.
Jian Chen, et al., "Solution Properties of Single-Walled Carbon Nanotubes," Science, 1998, vol. 282, 95-98.
Ralph Weissleder, et al., "In vivo imaging of tumors with protease-activated near-infrared fluorescent probes," Nature Biotechnology, 1999, vol. 17, 375-378.
Dunwei Wang, et al., "Surface Chemistry and Electrical Properties of Germanium Nanowires," J. Am. Chem. Soc., 2004, 126, 11602-11611, published online Aug. 25, 2004.
Paul Cherukuri, et al., "Near-Infrared Fluorescence Microscopy of Single-Walled Carbon Nanotubes in Phagocytic Cells," J. Am. Chem. Soc., 2004, 126, 15638-15639, published online Nov. 11, 2004.

(Continued)

*Primary Examiner* — Fereydoun G Sajjadi
*Assistant Examiner* — Michael B Pallay
(74) *Attorney, Agent, or Firm* — David J. Aston; Peters Verny, LLP

(57) ABSTRACT

Disclosed are nanoparticles, such as carbon nanotubes or other graphitic sheet materials having extended aromatic surfaces, which are used to deliver active agents such as drugs, labels or dyes (termed for convenience a "drug") to the interior of cells. The nanoparticles are functionalized by a hydrophilic polymer or adsorption of an amphiphilic molecule to render them stable in suspension. The drug is therefore capable of release in the cell exterior. The drug is more rapidly released at lower pH, as found e.g., in tumor cells. The drug may also be linked to a branched chain hydrophilic polymer, so that each polymer molecule carries more than one drug bound by a cleavable linker.

51 Claims, 32 Drawing Sheets

(56) References Cited

OTHER PUBLICATIONS

Davide Pantarotto, et al., "Translocation of bioactive peptides across cell membranes by carbon nanotubes," Chem. Commun., 2004, vol. 16, 16-17, published online Nov. 3, 2003.

Alberto Bianco, "Carbon nanotubes for the delivery of therapeutic molecules," Expert Opin. Drug Deliv., Nov. 2004, vol. 1, No. 1, 57-65.

Chris Dwyer, et al., "DNA-functionalized single-walled carbon nanotubes," Nanotechnology, 2002, vol. 13, 601-604.

Theodoros A. Felekis, et al., "Single-Walled Carbon Nanotube-Based Hybrid Materials for Managing Charge Transfer Processes," Rev. Adv. Mater. Sci., Aug. 2005, vol. 10, 272-276.

Ming Zheng, et al., "Structure-Based Carbon Nanotube Sorting by Sequence-Dependent DNA Assembly," Science, 2003, vol. 302, 1545-1548.

Enzo Menna, et al., "Shortened single-walled nanotubes functionalized with poly(ethylene glycol): preparation and properties," ISSN, 2003, xiii, 64-73.

S. G. Chou, et al., "Optical characterization of DNA-wrapped carbon nanotube hybrids," Chemical Physics Letters, Sep. 16, 2004, 397, 296-301.

G. Gruner, "Carbon Nanotube Transistors for Biosensing Applications," University of California Los Angeles and Nanomix Inc., Emeryville CA, at www.physica.ucla.edu/research/biophysics/pubs/paper 2006, 13 pp.

Tara Elkin, et al., "Immuno-Carbon Nanotubes and Recognition of Pathogens," ChemBioChem May 1, 2005 epub. 6;640-643).

Keith A. Williams, et al., "Carbon nanotubes with DNA recognition," Nature Dec. 19-26, 2002, vol. 420, 761.

Alberto Bianco, et al., "Cationic Carbon Nanotubes Bind to CpG Oligodeoxynucleotides and Enhance Their Immunostimulatory Properties," J. Am. Chem. Soc., 2005, 127:58-59, published online Dec 16, 2004.

* cited by examiner

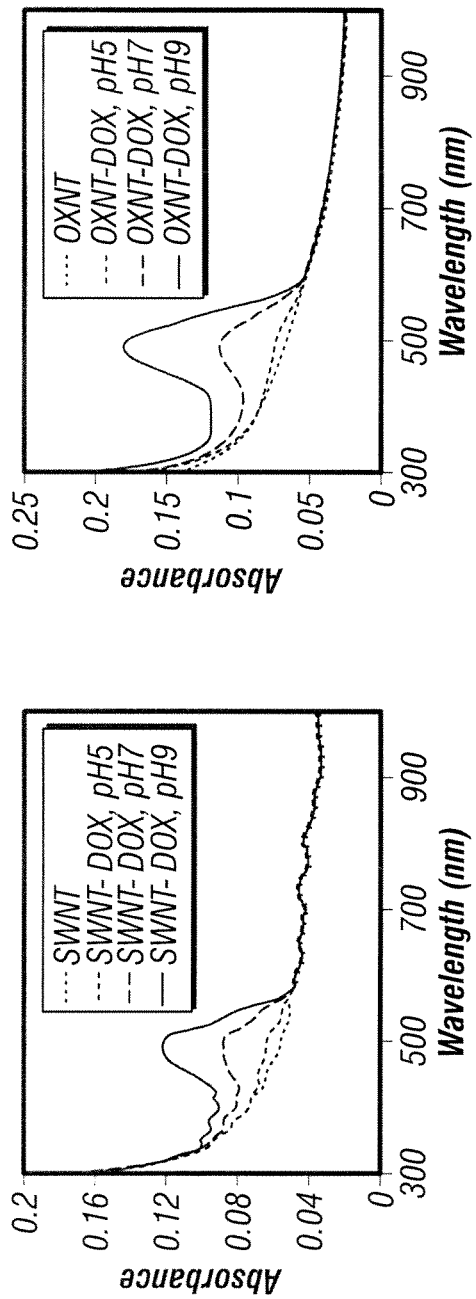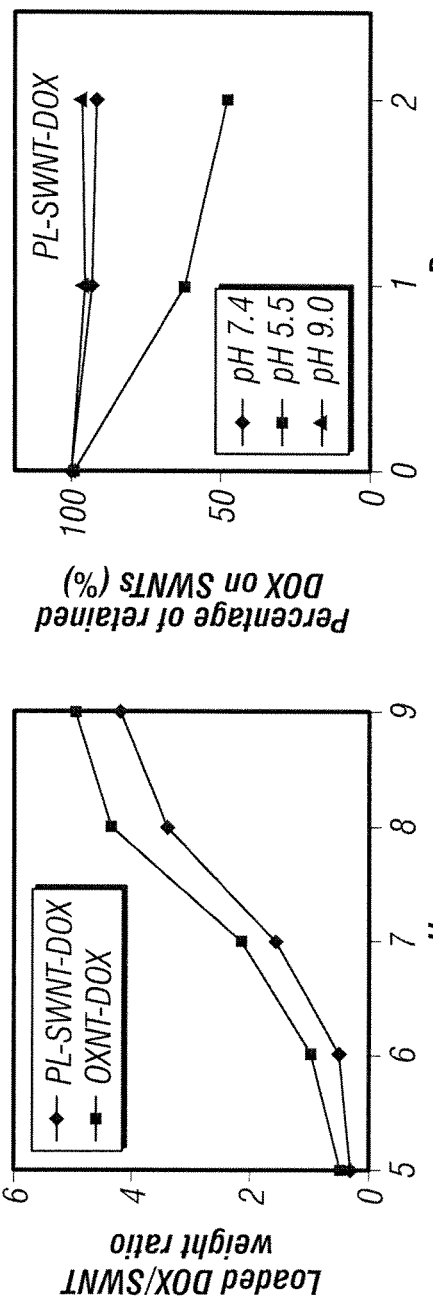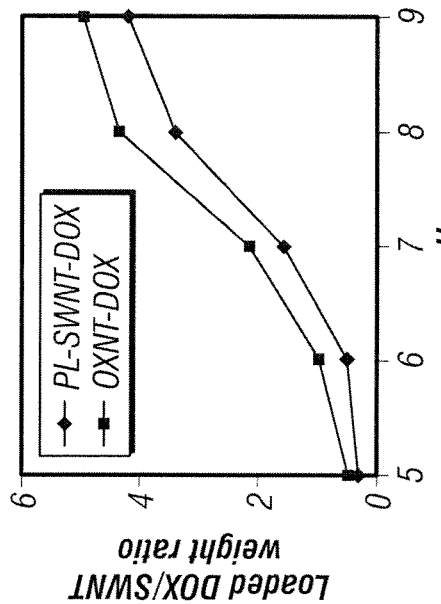
FIG. 3A
FIG. 3B
FIG. 3C
FIG. 3D

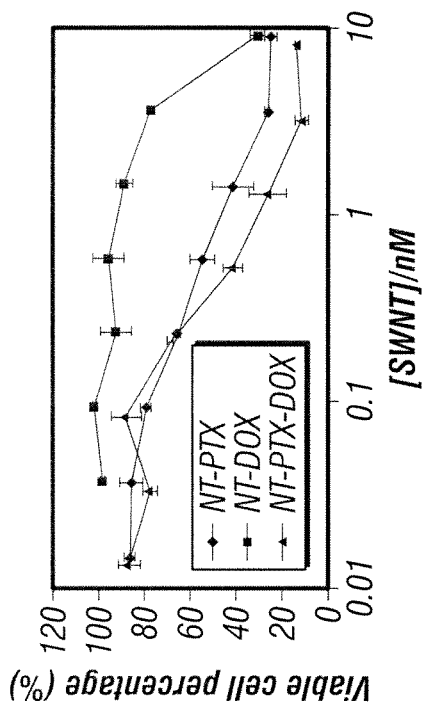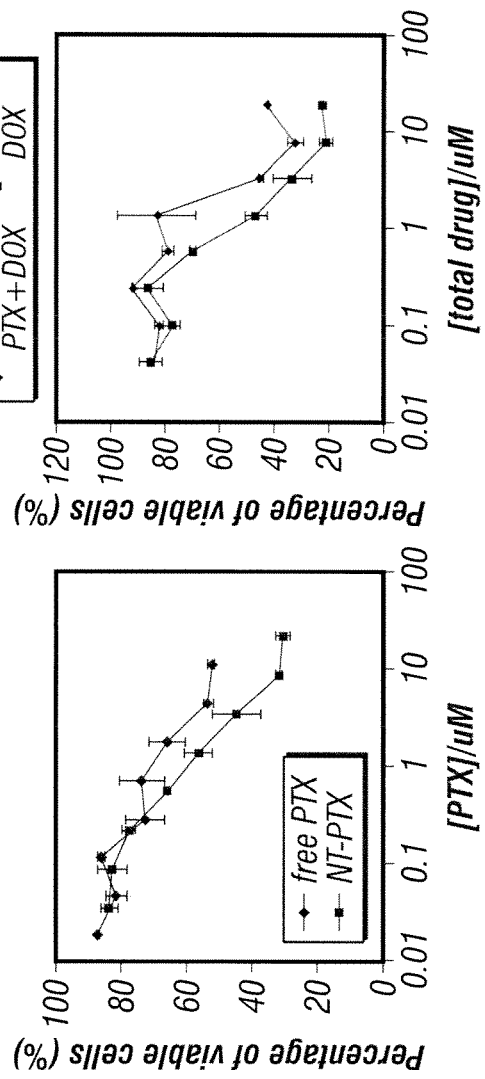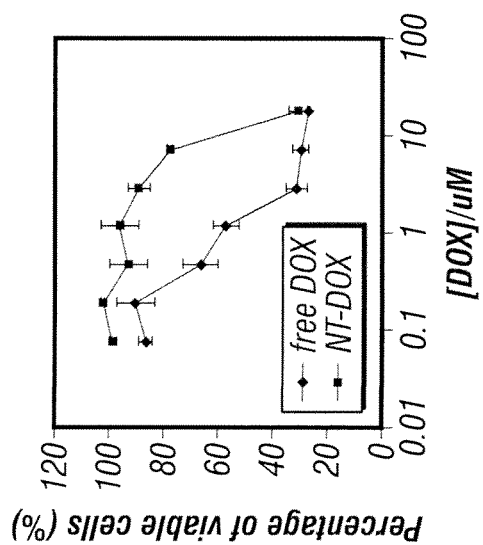
FIG. 15A
FIG. 15B
FIG. 15C
FIG. 15D

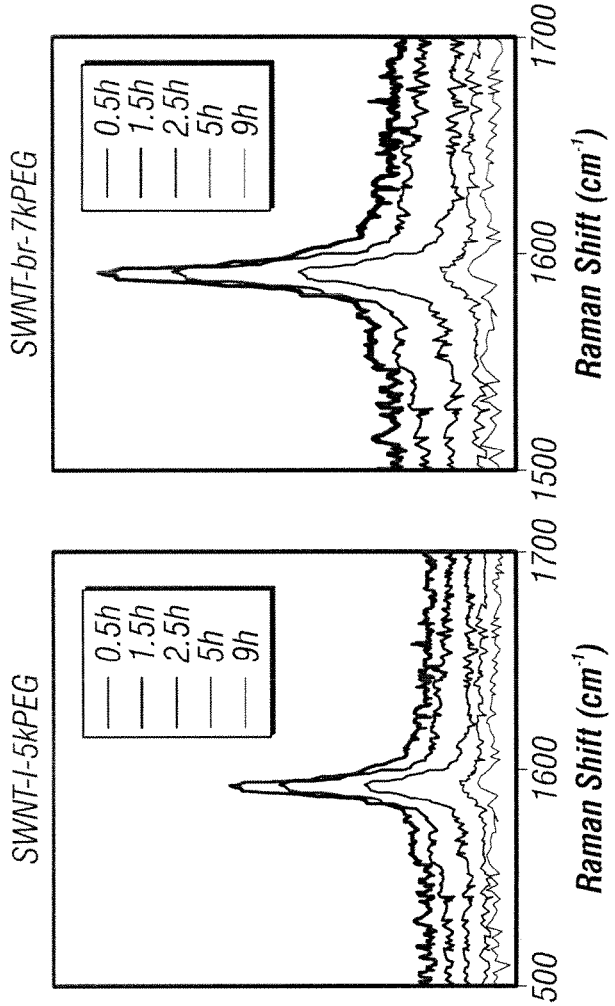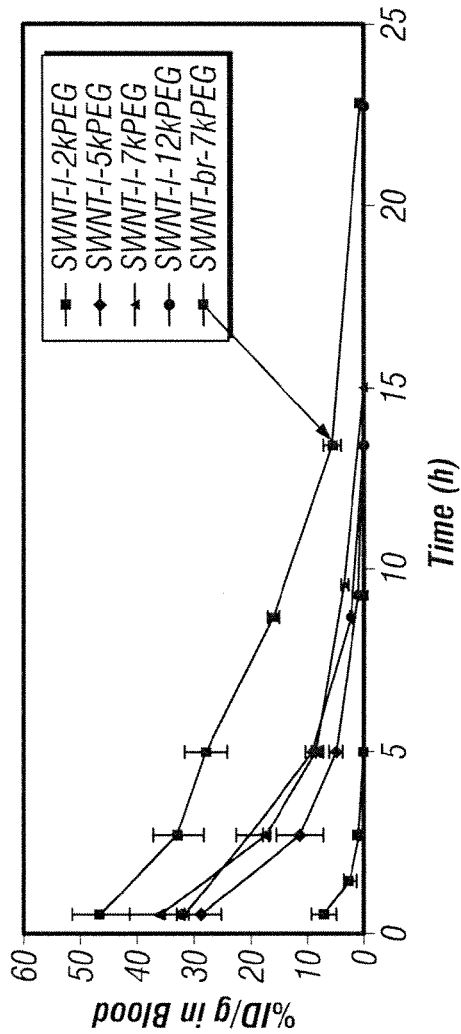
FIG. 22A  FIG. 22B  FIG. 22C  FIG. 22D

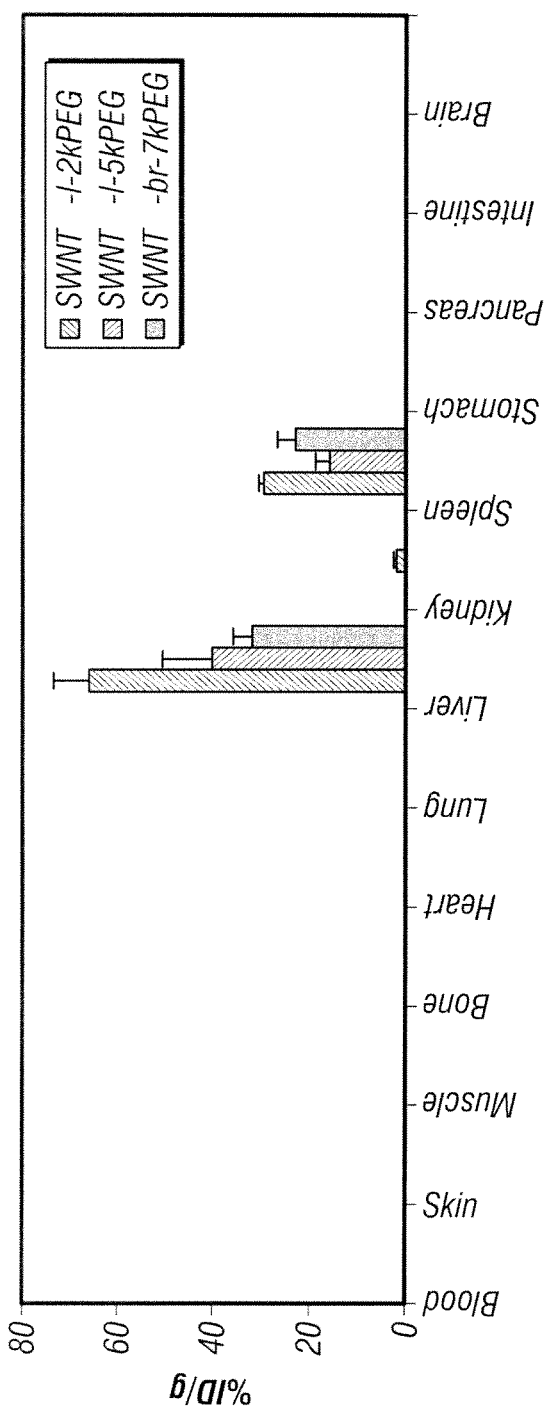
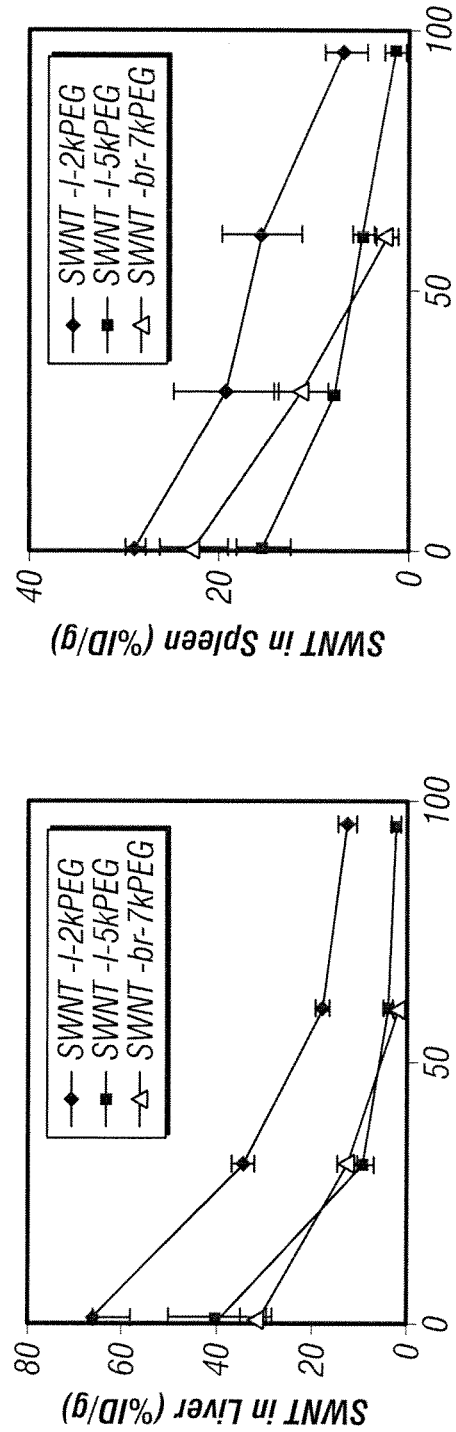
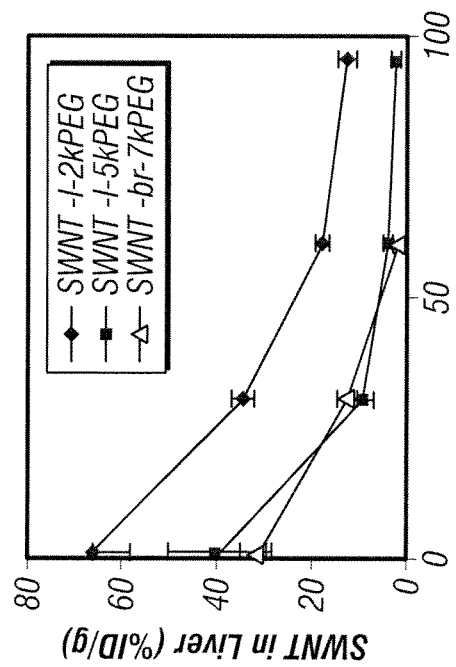
FIG. 23A
FIG. 23B
FIG. 23C

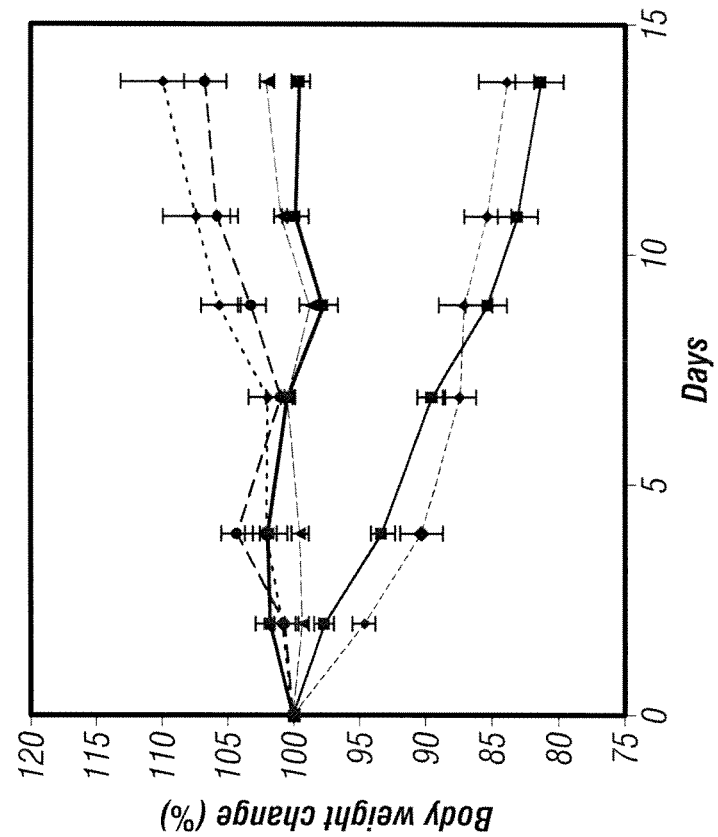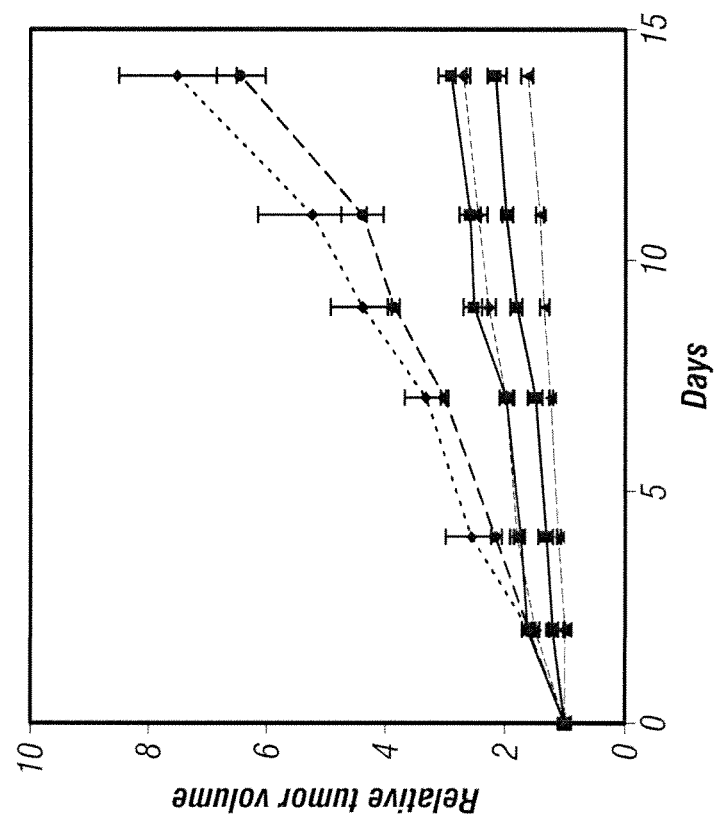
FIG. 26A
FIG. 26B

SUPRAMOLECULAR FUNCTIONALIZATION OF GRAPHITIC NANOPARTICLES FOR DRUG DELIVERY

CROSS-REFERENCE TO RELATED APPLICATIONS

This application claims priority from U.S. Provisional Patent Application No. 60/962,192 filed on Jul. 27, 2007, which is hereby incorporated by reference in its entirety.

STATEMENT OF GOVERNMENTAL SUPPORT

This invention was made with U.S. Government support under National Cancer Institute Grant U54CA119367. The U.S. Government has certain rights in this invention.

REFERENCE TO SEQUENCE LISTING, COMPUTER PROGRAM, OR COMPACT DISK

None.

BACKGROUND OF THE INVENTION

1. Field of the Invention

The present invention relates to the field of nanoparticles such as carbon nanotubes and to the field of delivery of drugs to cells.

2. Related Art

Single-walled carbon nanotubes (SWNT) are novel polyaromatic molecules with ultra-high surface areas of ~2600 $m^2/g$. While sidewall functionalization has been actively pursued,[1] little has been done to partition nanotube surfaces chemically and facilitate basic and practical applications for chemistry, biology and medicine.2-6 Accordingly, there is a need in the art for methods to partition nanotube surfaces.

Zheng, et al., "DNA-assisted dispersion and separation of carbon nanotubes" (2003) *Nature Mater.* 2: 338-342 describe the solubilization of carbon nanotubes by single stranded DNA molecules, wherein the DNA molecule wraps helically around the carbon nanotube through π-stacking interactions to form a soluble complex. See also, Zheng, et al., "Structure-Based Carbon Nanotube Sorting by Sequence-Dependent DNA Assembly," *Science* 29:1545-1548 (November 2003).

Dai, et al., WO 02/095099, entitled "Noncovalent sidewall functionalization of carbon nanotubes" (published Nov. 28, 2002 and related to PNAS 100:4984 cited below, as well as US PGPUB 2005/0100960) relates to complexes formed from the irreversible adsorption of molecules to the sidewalls of carbon nanotubes through π-stacking, van der Waals and hydrophobic interactions. As shown in the US PGPUB 2005/0100960, a plurality of noncovalently-bonded molecules, having a highly aromatic group such as a pyrenyl group, are configured and arranged for bonding to additional molecules, e.g., biomolecules such as antibodies, antigens and DNA. These complexes are intended for in vitro use, e.g., as biosensors, where the attached molecules do not dissociate from the nanotubes.

Chen et al., "Noncovalent functionalization of nanotubes for highly specific electronic biosensors", *PNAS*, 100:4984-4989 (2003) shows the binding of various proteins (Steptavidin, avidin, BSA, staphylococcal protein A and α-glucosidase) to as-grown nanotubes, and nanotubes treated with surfactants such as Tween, Pluronic P103 and Triton-X. It was reported that a monolayer of Tween 20 anchored on a nanotube would repel non-specific binding of proteins in solution. Ten different polypropylene oxide molecules were investigated for their ability to adsorb onto nanotube walls.

Hannah, US PGPUB 2004/0110128, published Jun. 10, 2004, entitled "Carbon Nanotube Molecular Labels," discloses that carbon nanotubes may be derivatized with reactive groups to facilitate attachment to analytes or probes. Nanotubes may be derivatized to contain carboxylic acid groups (U.S. Pat. No. 6,187,823). Carboxylate derivatized nanotubes may be attached to nucleic acid probes or other analytes by standard chemistries, for example by carbodiimide mediated formation of an amide linkage with a primary or secondary amine group located on a probe or analyte. The methods of derivatization and cross-linking are not limiting and any reactive group or cross-linking methods known in the art may be used.

US PGPUB 20040038251 to Smalley, et al., published Feb. 26, 2004, entitled "Single-wall carbon nanotubes of precisely defined type and use thereof," discloses that surfactants can also be used as non-perturbing coatings for suspending individual single-wall carbon nanotubes. The surfactant may be BRIJ® surfactants (polyethylene glycol dodecyl ether, polyethylene glycol lauryl ether, polyethylene glycol hexadecyl ether, polyethylene glycol stearyl ether, and polyethylene glycol oleyl ether), and other surfactants.

US PGPUB 20060014375 to Ford et al., published Jan. 19, 2006, entitled "Soluble carbon nanotubes," discloses a method of solubilizing carbon nanotubes. Carbon nanotubes and urea are mixed together and then heated.

Dwyer, et al., "DNA functionalized single-walled carbon nanotubes," *Nanotechnology*, 13:601-604 (2002) discloses linking DNA to nanotubes through amino-terminated DNA strands. A lambda DNA cluster is shown attached to a defect site and ends of an SWNT bundle.

Felekis, et al., "Single-walled carbon nanotube-based hybrid materials for managing charge transfer processes," *Rev. Adv. Mater. Sci.*, 10:272-276 (2005) discloses formation of nanohybrids consisting of SWNT units and electron donor moieties such as porpyrinic and ferrocenyl units.

Menna et al., in a conference paper dated Oct. 1, 2003, "Shortened single-walled nanotubes functionalized with poly (ethylene glycol): preparation and properties," disclose the grafting of PEG onto SWNTs after acid oxidative cutting, treatment with SOCl2 to yield SWMT-COCL, and amidation with PEG-monoamine.

Kam et al. "Nanotube Molecular Transporters: Internalization of Carbon Nanotube-Protein Conjugates into Mammalian Cells," *J. Am. Chem. Soc.*, 126 (22), 6850-6851, (2004) discloses SWNT-protein conjugates delivered to cells. The authors used an oxidation/sonication procedure, which introduced surface carboxylates on the nanotubes for chemical derivatization. The carboxylic acid was treated with aminobiotin or a fluorescent label.

Zhang Liu, Weibo Cai, Lina He, Nozomi Nakayama, Kai Chen, Xiaoming Sun, Xiayuan Chen, Hongjie Dai. "In vivo biodistribution and highly efficient tumour targeting of carbon nanotubes in mice," *Nature Nanotechnology*, Vol. 2, 47-52, January 2007 disclose the preparation of SWNTs, which were functionalized by the strong adsorption of phospholipids grafted onto amine-terminated polyethylene glycol. Thiol-modified siRNA cargo molecules were linked to the amine groups on the sidewalls of SWNTs through cleavable disulfide bonds.

Won Seok Seo, Jin Hyung Lee, Xiaoming Sun, Yoriyasu Suzuki, David Mann, Zhuang Liu, Masahiro Terashima, Philip C. Yang, Michael V. McConnell, Dwight G. Nishimura, and Hongjie Dai. "FeCo/graphitic-shell nanocrystals as advanced magnetic-resonance-imaging and near-infrared agents," *Nature Materials*, VOL 5, 971, 2006 discloses the preparation of pure FeCo/graphitic carbon nanocrystals. These were PL-PEG functionalized for MRI imaging.

Nadine Wong Shi Kam, Zhuang Liu, and Hongjie Dai "Carbon Nanotubes as Intracellular Transporters for Proteins and DNA: An Investigation of the Uptake Mechanism and Pathway," *Angew. Chem. Int. Ed.*, 44, 1-6, 2005, discloses acid oxidized SWNTs, which were used for conjugation with proteins, and non-oxidized SWNTs, which were used to complex with DNA molecules.

Nadine Wong Shi Kam and Hongjie Dai "Carbon Nanotubes as Intracellular Protein Transporters: Generality and Biological Functionality," *J. Am. Chem. Soc.*, 127, 6021-6026, 2005, discloses that SWNTs are generic intracellular transporters for various types of proteins (less than or equal to 80 kD) noncovalently and non-specifically bound to nanotube sidewalls.

Nadine Wong Shi Kam, Theodore C. Jessop, Paul A. Wender, and Hongjie Dai, "Nanotube Molecular Transporters: Internalization of Carbon Nanotube-Protein Conjugates into Mammalian Cells," *J. Am. Chem. Soc.*, 126, 6850-6851 2004, discloses the preparation of SWNTs refluxed in $HNO_3$ followed by sonication, resulting in negatively charged acidic groups on the surface, which were used to couple various molecules such as biotin.

BRIEF SUMMARY OF THE INVENTION

The following brief summary is not intended to include all features and aspects of the present invention, nor does it imply that the invention must include all features and aspects discussed in this summary.

The present invention provides methods using supramolecular chemistry (i.e., interactions between, rather than within, molecules) on nanoparticles exemplified by single wall carbon nanotubes and graphitic sheet materials, and further including nanoparticles in the form of ribbons or spheres. (SWNTs) are pre-functionalized non-covalently or covalently by common surfactant or acid-oxidation routes. Aqueous soluble SWNTs prepared with polyethylene-glycol (PEG) by the routes described below allow for π-stacking of various aromatic molecules, including a chemotherapy cancer drug doxorubicin with an ultrahigh loading capacity of ~400% by weight, a widely used fluorescence molecule fluorescein and combinations of molecules. Binding and releasing of molecules on the nanotubes exhibit novel diameter dependence and can be controlled by pH. These results uncover exciting opportunities for supramolecular chemistry on water soluble SWNTs, for applications ranging from drug delivery to chemical and biological imaging and sensing.

As described in the examples below, graphene sheets may be may be prepared in pristine form or in the form of graphene oxide. The sheets may be linked to a hydrophilic polymer such as PEG, either covalently, through the functional groups introduced into the nanoparticle graphene oxide (NGO), or through supramolecular bonding to a lipid polymer attached to the hydrophilic polymer, as described in connection with the SWNTs. As described below, it has been found that aromatic drugs may be bonded to the surface of the sheets through supramolecular bonding, and PEGylated. In one aspect, the present invention involves the use of camptocethin derivatives, aromatic drug molecules, such as SN-38, and geftinib, a quinazolamine. In some cases, the graphene is prepared as a single atom-thick molecular sheet. The sheets are controlled in width and length, and may in some cases be less than 100 nm, 20 nm, or less than 10 nm on a side, and, in all cases, of a size suitable for in vivo administration.

In addition, multiple different drugs may be delivered, including protein or peptide drugs covalently linked to the hydrophilic polymer, e.g., on the arms of branched PEG. As described below, an antibody may be used to target the complex, e.g., anti-CD20 to target B cells. The complex is further characterized as bearing a drug bonded to the nanoparticle, e.g., doxorubicin supramoleclularly bonded to the nanoparticle (e.g., NGO sheet).

Accordingly, the present invention comprises, in some embodiments, a nanoparticle complex for delivery of a small molecule active agent into a cell, comprising: a nanoparticle, a hydrophilic polymer bound to the nanoparticle, and a small molecule active agent, which may comprise an aromatic structure attached to the surface of the nanoparticle through supramolecular bonding. In certain embodiments the drug is bonded to the nanoparticle through supramolecular bonding, as in the case of pi-pi stacking between an aromatic drug and graphene on a nanoparticle surface. In another embodiment, the supramolecular bonding is between the nanoparticle and a solubilizing molecule, the solubilizing molecule having the drug attached to in through a cleavable linkage. The nanoparticle may be a carbon nanotube, which has a large surface area (up to ~2600 m2/g) available for supramolecular chemistry. The nanotube may be an SWNT, which can be made by a variety of processes, resulting in different diameters. Alternatively, the nanoparticle may be in the form of an aromatic structure as may be found in an SWNT, but in an unrolled form, i.e., a sheet. In general, the nanoparticle will have an extended aromatic structure as a pristine surface, i.e., with few blemishes, and will be hydrophobic. If an SWNT is used, it may have an average length of about 50-500 nm. It has been shown that diameter affects drug binding and/or release, and, in certain embodiments, the SWNT (or other nanotube) has a diameter of between about 1 and 2 nm prior to functionalization. The term "functionalization" refers to the addition of a solubilizing material, namely the hydrophilic polymer. In certain embodiments, this may be from about 10 to 500 PEO (polyethylene oxide) units, and may be straight chain or branched. In certain embodiments, the PEG (polyethylene glycol) is coupled to a phospholipid, and for that reason is amine-terminated. In this case, the solubilizing material may be referred to as an organic amphiphilic molecule, i.e., having a lipid or aliphatic (hydrophobic) portion and a hydrophilic portion. The lipid portion may comprise a polar lipid, e.g., a phospholipid. Branched hydrophilic polymers are preferred, and are shown to improve in vivo circulation. Branches may be linked at a single point of juncture, as in a + shape, so that three active agents are linked to the polymer, with the fourth arm linked to the nanoparticle.

The PEG or other hydrophilic polymer may be linked at an end opposite from the amine coupling end to a further molecule, which may be an active agent or a targeting agent for homing the complex to a particular cell type. In certain embodiments, the targeting agent is an RGD peptide, which is a specific ligand for extracellular receptors, such as integrins.

The hydrophilic polymer (e.g., PEG or dextran) may be covalently bound to the nanoparticle, or adsorbed to it by supramolecular chemistry, such as hydrophobic forces or π-stacking.

The small molecule active agents to be delivered by the present materials may be selected from a group of small molecule drugs comprising a fused aromatic ring structure. This permits π-stacking to the aromatic structure of the nanoparticle. In certain embodiments, the active agent may be selected from the group consisting of: doxorubicin (DOX), 7-Ethyl-10-hydroxycamptothecin (SN38), other camptothecin derivatives, daunorubicin, fluorescein and paclitaxel (PTX). The active agent may be selected from the class of anthracycline-based drugs (e.g., DOX). The active agent may be one of a number of anticancer drugs, which may be generally defined as antiproliferative agents, cytotoxic agents and immunosuppressive agents, e.g., toxorubicin, vinca-alcaloide, actinomycin, toposites, tamoxifen, cisplatin, carboplatin, satraplatin etc.

The present complexes may exhibit a high degree of loading with small molecule active agent. In certain embodiments, the nanoparticle complex may have about 5-40% of the nanoparticle surface complexed with the hydrophilic polymer and 60-95% complexed with the small molecule active agent. More than one agent may be employed in a single complex or mixture of complexes.

The complexes may be prepared in advantageous forms for drug delivery. They may be prepared as a stable aqueous suspension, and/or in unit dosage form.

In certain embodiments, the invention comprises a method for preparing a nanoparticle complex for delivery of a small molecule active agent inside a cell, where one first prepares nanoparticles in a suitable form, e.g., in dispersed form suitable for in vivo administration. In the method, one then attaches a hydrophilic polymer to the nanoparticles; attaches through supramolecular bonding an active agent to the surface of the nanoparticle; and forms a stable aqueous suspension of the complex. In certain embodiments, the supramolecular bonding is used to attach a linker molecule to which may be attached a hydrophilic molecule and/or an active agent. The present materials exist in dispersed form as opposed to aggregates, which may commonly form in the preparation of hydrophobic nanoparticles.

In certain embodiments, the invention comprises a method for delivering an active agent inside a cell, comprising contacting the cells with a nanoparticle; a hydrophilic polymer bound to the nanoparticle; and an active agent comprising an aromatic molecule non-covalently linked to the surface of the nanoparticle. The delivery may be targeted to certain cell types by attaching targeting agents to the complex.

BRIEF DESCRIPTION OF THE DRAWINGS

FIGS. 3A and 3B are graphs showing pH dependent supramolecular loading of doxorubicin on non-covalent and covalently PEGylated SWNTs, based on UV-Vis-NIR absorbance spectra of (3A) PL-PEG functionalized Hipco SWNTs (PL-SWNT) and (3B) PEGylated nitric acid-oxidized SWNTs (OXNT), with and without doxorubicin loaded at different pHs indicated. FIG. 3C is a graph of doxorubicin loading efficiency at various pH values for the two types of SWNTs, and FIG. 3D is a graph showing percentage of retained doxorubicin on PL-PEG SWNTs over time in buffers under the three pH values indicated.

FIG. 11B is a graph showing fluorescence spectra of PL-SWNT loaded with doxorubicin and fluorescein (same solution as in (11A) with the peak at 520 nm corresponding to emission of fluorescein bound to nanotubes and little fluorescence of the co-adsorbed doxorubicin despite the 2:1 doxorubicin to fluorescein ratio.

FIG. 15A-D is a series of graphs showing in vitro toxicity tests, as viable cell percentage of cells (15A) having NT-PTX, NT-DOX, or NT-PT-DOX; (15B) free DOX or NT-DOX; (15C), free PTX or NT-PTX; and (15D) free PTX+DOX or NT-PTX-DOX.

FIG. 22A-D are graphs showing blood sample analysis. 22A-C shows raw Raman spectra of blood samples from balb/c mice injected with SWNT-1-2kPEG (22A), SWNT-1-5kPEG (22B) or SWNT-br-7kPEG (22C). Blood was drawn at different time points post injection for Raman measurement. FIG. 22D shows blood circulation curves of SWNT-1-2kPEG, SWNT-1-5kPEG and SWNT-1-7kPEG, SWNT-1-12kPEG and SWNT-br-7kPEG. The SWNT levels in blood were determined as percentage of injected SWNT amount per gram of blood (% ID/g in blood). SWNT-1-5kPEG, SWNT-1-7kPEG and SWNT-1-12 kPEG showed similar blood circulation lives, which was significantly longer than that SWNT-2kPEG. The longest blood circulation was observed for SWNT-br-7kPEG. The error bars are based on 4 mice in each group. Note that spectrum baselines were subtracted in FIG. 22 A-C.

FIG. 23A-C is a series of graphs that show biodistribution of the SWNTs. FIG. 23A is a bar chart showing biodistribution of SWNT-1-2kPEG, SWNT-1-5kPEG and SWNT-br-7kPEG at 1-day p.i. measured by Raman spectroscopy; FIGS. 23B and 23C are graphs showing SWNT levels in liver and spleen over time. Compared with SWNT-1-2kPEG, obviously less retained nanotube Raman signal was observed for SWNT-1-5kPEG and SWNT-br-7kPEG. The latter exhibited the lowest retention at 2-month p.i. The error bars in a-c are based on 3-4 mice per group.

FIG. 26A-D is a series of graphs showing relative tumor volumes (A,C) and body weight changes (B,D) observed when Raji tumor bearing SCID mice were treated with different DOX formulations once a week with tumor sizes and body weights recorded. FIG. 26 (A) is a graph of tumor growth curves of untreated (n=7), 5 mg/kg free DOX treated (n=10, 2 mice died in the second week), plain SWNT treated (n=5), 5 mg/kg free followed by plain SWNT treated (n=5), 5 mg/kg SWNT-DOX treated (n=10) and 10 mg/kg untreated (n=10) mice. FIG. 26 (B) is a graph of body weight curves of mice in FIG. 26A. FIG. 26 (C) is a graph of tumor growth curves of 5 mg/kg Doxil treated (n=5, 2 mice died in the second week) mice compared with untreated and SWNT-DOX treated mice. FIG. 26 (D) is a graph of body weight curves of mice in FIG. 26(C). SWNT-DOX exhibited slightly higher efficacy than free DOX but lower efficacy than Doxil at the same dose (5 mg/kg). However drastically lower side effects were observed for SWNT-DOX treated mice at normal (5 mg/kg) or even doubled dose (10 mg/kg), compared with quick body weight drop and mouse death in the free DOX and Doxil groups at normal dose.

FIG. 28 (B) shows relative cell viability data of HCT-116 cells after incubation with NGO-PEG with (lower line) and without (upper line) SN38 loading. Plain NGO-PEG exhibited no obvious toxicity even at very high concentrations. Error bars were based on triplet samples.

DETAILED DESCRIPTION OF THE PREFERRED EMBODIMENT

Definitions

Figure 1A:
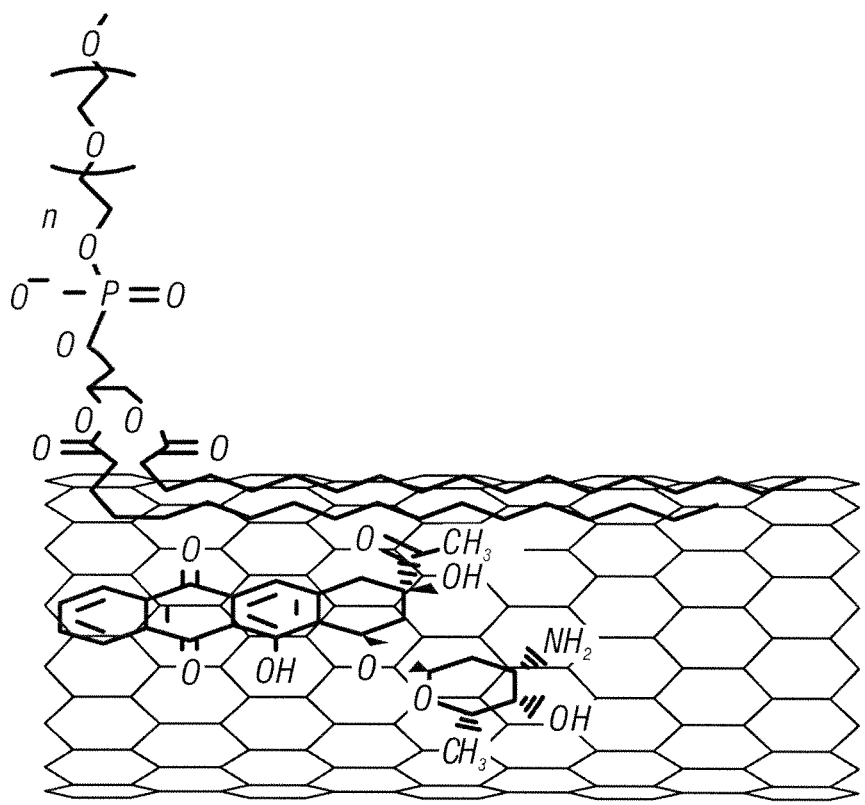
FIG. 1A is a schematic drawing of doxorubicin π-stacking onto a nanotube with non-covalently bound phospholipid (PL)-PEG (left)

Unless defined otherwise, all technical and scientific terms used herein have the same meaning as commonly understood by those of ordinary skill in the art to which this invention belongs. Although methods and materials similar or equivalent to those described herein can be used in the practice or testing of the present invention, the preferred methods and materials are described. Generally, nomenclatures utilized in connection with, and techniques of, materials science and chemistry are those well known and commonly used in the art. Certain experimental techniques, not specifically defined, are generally performed according to conventional methods well known in the art and as described in various general and more specific references that are cited and discussed throughout the present specification. For purposes of the clarity, following terms are defined below.

The term "active agent" means a molecule that imparts some activity to a cell, which takes up the agent. The activity may be a marker activity, as in the uptake of a fluorescent probe, or it may be a metabolic activity such as apoptosis. Preferably the active agent is biologically active. The agent may modulate any number of biological functions in the cell, such as cell division, a cellular infection, cellular expression of cell surface proteins, cellular response to a hormone such as insulin, etc. The term "biologically active" further refers to polynucleotides, small molecules, and polypeptides which cause a metabolic change in a cell, generally by increasing transcription or expression or translocation of one or more genes, or by binding to an expressed protein. The term "small molecule" is used in a conventional sense, more particularly a monomeric compound having a molecular weight less than about 1000 Daltons. The active agent may preferably be a small molecule, which is an aromatic molecule.

The term "aliphatic," as used herein, includes both saturated and unsaturated, straight chain (i.e., unbranched), branched, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl," "alkynyl" and the like. Furthermore, as used herein, the terms "alkyl," "alkenyl," "alkynyl" and the like encompass both substituted and unsubstituted groups, such as alkoxy, thioalkyl, or alkyl amino groups. In certain embodiments, as used herein, "lower alkyl" is used to indicate those alkyl groups (cyclic, acyclic, substituted, unsubstituted, branched or unbranched) having 1-6 carbon atoms.

The aliphatic (lipid) alkyl groups employed in the lipids of the invention preferably contain 4-20, more preferably 10-20 aliphatic carbon atoms. In certain other embodiments, the lower alkyl, (including alkenyl, and alkynyl) groups employed in the invention contain 1-10 aliphatic carbon atoms. Illustrative aliphatic groups thus include, but are not limited to, for example, methyl, ethyl, n-propyl, isopropyl, cyclopropyl, —CH2-Cyclopropyl, allyl, n-butyl, sec-butyl, isobutyl, tert-butyl, cyclobutyl, —CH2-cyclobutyl, n-pentyl, sec-pentyl, isopentyl, tert-pentyl, cyclopentyl, —CH2-cyclopentyl-n, hexyl, sec-hexyl, cyclohexyl, —CH2-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like. The aliphatic groups are hydrophobic and adsorb to the hydrophobic nanoparticle.

The term "alkoxy" (or "alkyloxy"), or "thioalkyl" as used herein refers to an alkyl group, as previously defined, attached to the parent molecular moiety through an oxygen atom or through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkoxy include, but are not limited to, methoxy, ethoxy, propoxy, isopropoxy, n-butoxy, tert-butoxy, neopentoxy and n-hexoxy. Examples of thioalkyl include, but are not limited to, methylthio, ethylthio, propylthio, isopropylthio, n-butylthio, and the like.

The term "alkylamino" refers to a group having the structure —NHR' wherein R' is alkyl, as defined herein. The term "dialkylamino" refers to a group having the structure —N(R')2, wherein R' is alkyl, as defined herein. The term "aminoalkyl" refers to a group having the structure NH2 R'—, wherein R' is alkyl, as defined herein. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkylamino include, but are not limited to, methylamino, ethylamino, iso-propylamino and the like.

The term "aryl" means 5- and 6-membered single-ring aromatic radicals which may include from zero to four heteroatoms in the ring, and which further include from zero to two heteroatoms in the ring, selected from oxygen, nitrogen and sulfur and which may be unsubstituted or be substituted with alkyl, halogen or alkoxy. Representative aryls include phenyl, thienyl, furanyl, pyridinyl, imidazolyl, thiazolyl, pyrimidinyl, pyrazinyl, pyridazinyl, (is)oxazolyl, triazolyl, tetrazolyl, pyrrolyl, pyridinyl-N-oxide and the like.

The term "aromatic molecule" means an aromatic molecule which functions as an "active agent" in a defined environment such as a biological environment, more particularly, within a cell. The aromatic molecule is preferably a biologically relevant molecule including DNA, RNA, proteins, peptide, polypeptide or polynucleotide or a small molecule that normally has poor cellular uptake by itself, such as the exemplified doxorubicin, daunorubicin, fluorescein, SN38, or paclitaxel. Cellular uptake is measured by intracellular concentration in target cells or organs, e.g., by immunofluorescence, confocal microscopy or flow cytometry or radio imaging. The term "aromatic" is used in a conventional sense to mean a compound that has special stability and properties due to a closed loop of electrons. The compound (including hetero-aromatic structures) has a planar ring with 4n+2 pi-electrons where n is a non-negative integer (Hülckel's Rule). The prototypical aromatic molecule is benzene, but the present aromatic molecules include fused ring structures, and heterocyclic rings such as pyridines, pyrimidines, and pyrazines, which are frequently used in drugs. The term "aromatic small molecule" means a molecule such as those exemplified, and may include nucleic acids or polypeptides in oligomeric (e.g., less then about 4 residue) form, but excludes polymers such as RNA, DNA or polypeptides, where the nanoparticle and the molecule may be simply entangled.

The term "camptothecin" means a cytotoxic quinoline alkaloid, including known derivatives and analogs, such as SN38, which has the formula below:

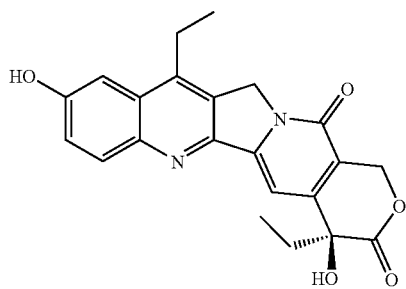 [SMILES: CCc1c2c(nc3ccc(O)cc13)-c1cc3c(c(=O)n1C2)COC(=O)[C@]3(O)CC]

Aromatic small molecule drugs include the exemplified doxorubicin, dauonorubicin SN38 and taxol, as well as a wide variety of other drugs such as antibiotics ciprofloxacin, telithromycin (Ketek, Aventis Pharmaceuticals), tetracycline (which is also an MMP inhibitor) and doxycycline. As further examples, the most common drugs used against malaria and as HIV integrase inhibitors including the anti-malarial chloroquine, are based on quinoline, a heteroaromatic compound (similar to naphthalene, except with one carbon replaced by nitrogen). Morphine and other morphanans, based on fused ring aromatic structures, are also included in the present definition. Various nucleic acid analogs also contain aromatic structures, such as the pro-drug 5-fluorocytosine (5-FC) used in cancer therapy. The present complexes are well suited for use with small aromatic ligand molecules that bind to DNA double helical structures by (i) intercalating between stacked base pairs thereby distorting the DNA backbone conformation and interfering with DNA-protein interaction or (ii) the minor groove binders. Both work through non-covalent interaction.

The present aromatic molecules will contain an aryl group.

The term "carbon nanotube" means a tube that contains a sheet of graphene rolled into a cylinder as small as 1 nm in diameter. Both single-walled nanotubes (SWNTs) and multiwalled nanotubes (MWNTs), with many concentric shells, have been synthesized. The electronic properties of a nanotube depend on the angle (chirality) with which it is rolled up—the present nanotubes can be metals, small-gap semiconductors, or large-gap semiconductors. Carbon nanotubes may include other materials. Metallic tubes have shown ballistic conduction on length scales of a micron or more. Nanotubes are also the stiffest known material, with a Young's modulus of ~1 TPa, which makes them excellent candidates for nanomechanical systems. Carbon nanotubes, as used herein, includes structures that are not entirely carbon, such as BCN nanotubes. The present carbon nanotubes may also be graphene in other forms. This includes a single sheet of graphene formed into a sphere, which constitutes a carbon nanosphere, commonly referred to as a buckyball or fullerene. Sheets of graphene are also included. In particular, the term "graphene sheet" means a one-atom-thick two-dimensional layer of sp2-bonded carbon. Further exemplary description may be found at Stankovich et al., "Graphene-based composite materials," Nature, 442, 282-286 (20 Jul. 2006). As described there, these sheets may incorporate graphite oxide, a layered material produced by the oxidation of graphite. In contrast to pristine graphite, the graphene-derived sheets in graphite oxide (graphene oxide sheets) are heavily oxygenated, bearing hydroxyl and epoxide functional groups on their basal planes, in addition to carbonyl and carboxyl groups located at the sheet edges. The presence of these functional groups makes graphene oxide sheets strongly hydrophilic, which allows graphite oxide to readily swell and disperse in water.

The expression "dosage unit form" means a physically discrete unit of therapeutic agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts (see, for example, Goodman and Gilman's, "The Pharmacological Basis of Therapeutics," Tenth Edition, A. Gilman, J. Hardman and L. Limbird, eds., McGraw-Hill Press, 155-173, 2001, which is incorporated herein by reference in its entirety).

The term "effective amount" means a sufficient amount of agent to cause a detectable decrease in the condition to be modulated in the cell, or an increase in the desired effect, e.g., detectability of acellular process. It may reduce the severity of the disease or increase or decrease caspase activity and/or cell apoptosis, as measured by any of the assays described in the examples herein. The exact amount required will vary from subject to subject, depending on the species, age, and general condition of the subject, the severity of the infection, the particular therapeutic agent, its mode of administration, and the like. The compounds of the invention are preferably formulated in dosage unit form for ease of administration and uniformity of dosage.

The term "hydrophilic polymer" means a material that has the property of dissolving in, absorbing, or mixing easily with water, and comprises repeating units constituting an MW of at least 200 (e.g., PEG 200) up to 8,000 or more. Hydrophilic polymers include PEG as well as other materials, which can be used to solubilize nanoparticles. Materials for this purpose include poly(hydroxyalkyl methacrylates), poly(N-vinyl-2-pyrrolidone), anionic and cationic hydrogels, polyelectrolyte complexes, poly(vinyl alcohol) having a low acetate residual and cross-linked with glyoxal, formaldehyde, or glutaraldehyde, methylcellulose cross-linked with a dialdehyde, a mixture of agar and sodium carboxymethyl cellulose, a water-insoluble, water-swellable copolymer produced by forming a dispersion of finely divided copolymer of maleic anhydride with styrene, ethylene, propylene, butylene or isobutylene cross-linked with from about 0.001 to about 0.5 mole of a polyunsaturated cross-linking agent per mole of maleic anhydride in the copolymer as disclosed in U.S. Pat. No. 3,989, 586, water-swellable polymers of N-vinyl lactams as disclosed in U.S. Pat. No. 3,992,562, and the like (See U.S. Pat. No. 4,207,893 to Michaels, issued Jun. 17, 1980, entitled "Device using hydrophilic polymer for delivering drug to biological environment.") A preferred polymer is dextran, which may be branched. The dextran straight chain consists of α1->6 glycosidic linkages between glucose molecules, while branches begin from α1->3 linkages (and in some cases, α1->2 and α1->4 linkages as well). One may apply Dextran 10, Dextran 40 and Dextran 70 (Mw=10,000, 40,000 and 70,000, respectively) at a concentration analogous to those described for PEG.

Hydrophilic polymers suitable for use herein include polyethylene glycol (PEG), polyoxyethylene, polymethylene glycol, polytrimethylene glycols, polyvinyl-pyrrolidones, poly lysine (D or L) and derivatives thereof with PEG being particularly preferred. The polymers can be linear or multiply branched, and will not be substantially crosslinked. Other suitable polymers include polyoxyethylene-polyoxypropylene block polymers and copolymers. Polyoxyethylene-polyoxypropylene block polymers having an ethylene diamine nucleus (and thus having four ends) are also available and may be used in the practice of the invention.

The hydrophilic polymer used here will render the nanoparticles soluble when attached thereto in sufficient numbers. A precise hydrophobic/hydrophilic measurement can be made as described in Bowe et al., "Design of compounds that increase the absorption of polar molecules," *Proc. Natl. Acad. Sci. USA*, Vol. 94, pp. 12218-12223, October 1997.

Figure 16:
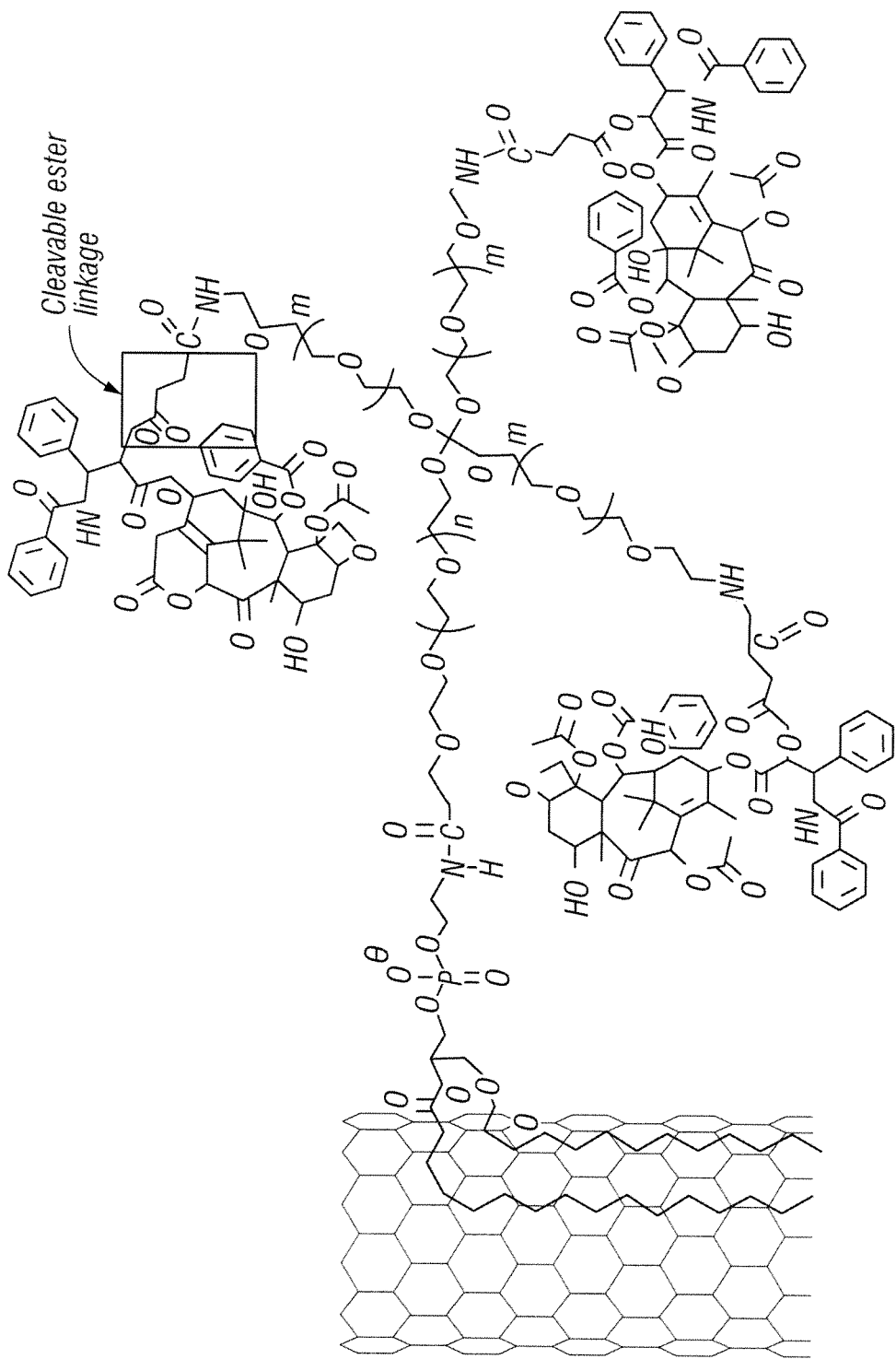
FIG. 16 is a schematic drawing showing the structure of PTX attached to branched PEG amine coupled to a phospholipid, with the lipid portion on an SWNT.

The hydrophilic polymer may be branched, as shown in FIG. 16 which shows PEG having 4 branches, thus providing three attachment sites for the active agent. For example, 2, 3, 4 and 8 arm branched PEGs are available from NOF Corporation, Tokyo Japan. Further description of multi-arm hydrophilic molecules is found in "Multi-arm block copolymers as drug delivery vehicles," U.S. Pat. No. 6,730,334.

The term "nanoparticle" means a material having the properties of a carbon nanotube insofar as the material is essentially aromatic. The present nanoparticles will typically be a hydrophobic material and will have a diameter on the order of the diameter of an SWNT or MWNT (preferably 10-20 nm, not more than 100 nm) or smaller, and length not more than about 20 μm, preferably of not more than 50-500 nm in length. They will be atomically ordered and generally chemically inert, such as a nanowire (see, e.g., "Controlled growth of highly uniform, axial/radial direction-defined, individually addressable InP nanowire arrays," Premila Mohan et al 2005 *Nanotechnology* 16 2903-2907, and US PGPUB 20050221083 to Belcher, et al., published Oct. 6, 2005, entitled "Inorganic nanowires," hereby incorporated by reference), fullerenes, fullerenols, etc. The term "nanoparticles" is also intended to include nanostructured materials <100-1000 nm in at least one of the three dimensions such as tubes, wires, particles, sheets and crystals. The term "nanoparticles" also includes carbon black, whose primary particles range in size from 10 nm to 500 nm. Carbon blacks are commercially available in a variety of particle sizes and morphologies. The term "nanoparticle" also includes hydrophobic polymeric particles, such as spheres of nanoparticle size, i.e., less than 1000 nm, e.g., polystyrene beads of 20, 50 or 100 nm as exemplified below. The term "hydrophobic polymer" is used herein to mean any polymer resistant to wetting, or not readily wet, by water, i.e., having a lack of affinity for water. A hydrophobic polymer typically will have a surface free energy of about 40 dynes/cm ($10^{-5}$ Newtons/cm or N/cm) or less.

Examples of hydrophobic polymers which can be used to form nanoparticles include, by way of illustration only, polylactide; polylactic acid; polyolefins, such as poylethylene, poly(isobutene), poly(isoprene), poly(4-methyl-1-pentene), polypropylene, ethylene-propylene copolymers, and ethylenepropylene-hexadiene copolymers; ethylene-vinyl acetate copolymers; and styrene polymers, such as poly(styrene), poly(2-methylstyrene), styrene-acrylonitrile copolymers having less than about 20 mole-percent acrylonitrile, and styrene-2,2,3,3, -tetrafluoro-propyl methacrylate copolymers. Further examples are given in U.S. Pat. No. 6,673,447, hereby incorporated by reference.

As exemplified by polystyrene and ordered graphene carbon sheets, tubes, spheres, or other shapes, the preferred nanoparticle has an extended aromatic structure, i.e., materials which comprise at least one repeating unit that includes an extended aromatic ring or a polycyclic aromatic ring system containing 2, 3, 4 or more rings, preferably at least two of the rings being fused, from about 3 to 8 ring members in each ring. The term "extended aromatic ring system" refers to an aromatic group, particularly a single ring group such as phenyl, that is either fused to another ring or contains one or more unsaturated ring substituents such as cyano, alkenyl, alkynyl, alkanoyl, nitro, etc. Compounds with extended aromatic structures are further exemplified in U.S. Pat. No. 3,197,475 issued Jul. 27, 1965. Elemental carbon consists of an extended aromatic-ring structure where the carbon atoms are bonded by $sp^2$-bonds and delocalized pi-bonds. As the number of rings increase, these pi-bonding electron orbitals become degenerate across the entire structure and end up existing at a level with little or no gap between the valence bands and conduction bands.

Also included are particles such as Boron nitride (BN) nanotubes, which have been synthesized and shown to behave in many ways like their carbon nanotube analogues [Chopra et al., *Solid State Commun*, (1998) 105: 297-300; Cumings et al., *Chem. Phys. Lett.*, (2000) 316: 211-216]. For example, they show the same propensity to agglomerate into bundles held together by van der Waals attractive forces. Furthermore, they have been observed to exist as single- or multi-walled varieties. Other boron nanoparticles suitable for use are described in Suenaga et al., "Synthesis of Nanoparticles and Nanotubes with Well-Separated Layers of Boron Nitride and Carbon," *Science,* 24 Oct. 1997: Vol. 278. no. 5338, pp. 653-655.

Another exemplary nanoparticle having an extended aromatic structure, i.e., a graphene surface, is a coated metal or metal oxide nanocrystal. Seo et al., 'FeCo/graphitic-shell nanocrystals as advanced magnetic-resonance-imaging and near-infrared agents," *Nature Materials* 5, 971-976 (2006) describes, in the preferred embodiment, the preparation of a scalable chemical vapor deposition method to synthesize FeCo/single-graphitic-shell nanocrystals that are soluble and stable in water solutions. In addition, U.S. Pat. No. 6,843,919 to Klabunde, et al., issued Jan. 18, 2005, entitled "Carbon-coated metal oxide nanoparticles," discloses methods of preparation of nanoparticles having from about 10-20% by weight carbon coating layer, based upon the total weight of the final coated composite taken as 100% by weight. The coating layer is graphitic and carbonaceous in nature and will comprise at least about 90% by weight carbon and preferably at least about 98% by weight carbon. Hollow graphitic nanoparticles may also be prepared, as described in US PGPUB 2006/0198949 by Phillips et al., published Sep. 7, 2006, entitled "Preparation of graphitic articles." Sutter et al., "Assembly and interaction of Au/C core-shell nanoparticles," *Surface Science*, Volume 600, Issue 18, Pages 3525-4404 (15 Sep. 2006) discloses that, at high temperatures (400-800° C.), Au particles are transformed into Au/C core-shell structures via encapsulation into curved, fullerene-like C shells, thus describing another method for preparing nanoparticles having a graphitic surface.

In summary, a nanoparticle is a nanostructured material <100-1000 nm in the shape of a tube, sheet, ribbon or spheres, having an extended aromatic structure.

The term "organic amphiphilic molecule" means an amphiphile containing a hydrophobic portion, such as an alkyl group of at least 3 carbon atoms, linked to a hydrophilic portion, e.g., a hydrophilic polymer, for stabilizing the molecule in aqueous solution. The alkyl group may be a lipid attached to a polar head group, which itself is hydrophilic or is bonded to a hydrophilic polymer. The hydrophilic polymer is preferably a polymer such as PEG.

The term "PEG" means Polyethylene glycol, a polymer with the structure $(-CH_2CH_2O-)_n$ that is synthesized normally by ring opening polymerization of ethylene oxide. The PEG used herein will impart water (and serum) solubility to the hydrophobic nanoparticle and lipid portion of the polar lipid. The polymer is usually linear at molecular weights (MWs)≦10 kD. The PEG used here will have an MW below 5,400, preferably below 2,000, or about 45 repeating ethylene oxide units. However, the higher MW PEGs (higher "n" repeating units) may have some degree of branching. Polyethylene glycols of different MWs have already been used in pharmaceutical products for different reasons (e.g., increase in solubility of drugs). Therefore, from the regulatory standpoint, they are very attractive for further development as drug or protein carriers. The PEG used here should be attached to the nanoparticles at a density adjusted for the PEG length. For example, with PL-PEG 2000, we have an estimate of ~4 nm spacing between PEG chains along the tube. At this spacing, PEG5400 is too long and starts to block interaction with the cell surface. For PEG at ~1 nm distance, the PEG MW should be less than about 200, to allow hydrophobicity.

For coupling proteins to PEG, usually monomethoxy PEG [CH3(—O—CH2-CH2)$_n$—OH] is first activated by means of cyanuric chloride, 1,1'-carbonyldiimidazole, phenylchloroformate, or succidinimidyl active ester before the addition of the protein. In most cases, the activating agent acts as a linker between PEG and the protein, and several PEG molecules may be attached to one molecule of protein. The pharmacokinetics and pharmacodynamics of the present nanotubes-PEG-protein conjugates are expected to be somewhat dependent on the MW of the PEG used for conjugation. Generally the presently used PEG will have a molecular weight of approximately 100-2,000 Daltons.

The present PEG may also be modified PEG such as PolyPEG® (Warwick Effect Polymers, Ltd., Coventry, England), which is new range of materials suitable for the attachment of polyethylene glycol (PEG) to therapeutic proteins or small molecules. These are prepared using Warwick Effect Polymers' polymerization technology, (See U.S. Pat. No. 6,310,149) and contain terminal groups suitable for conjugation with, among other things, lysine, terminal amino and cysteine residues.

The term "polar lipid" refers to a molecule having an aliphatic carbon chain with a terminal polar group. Preferred polar lipids include but are not limited to acyl carnitine, acylated carnitine, sphingosine, ceramide, phosphatidyl choline, phosphatidyl glycerol, phosphatidyl ethanolamine, phosphatidyl inositol, phosphatidyl serine, cardiolipin and phosphatidic acid. Further polar lipids are exemplified in U.S. Pat. No. 6,339,060, "Conjugate of biologically active compound and polar lipid conjugated to a microparticle for biological targeting," to Yatvin, et al., hereby incorporated by reference.

The term "phospholipid" means a molecule having an aliphatic carbon chain with a terminal phosphate group. Typically the phospholipids will comprise a glycerol backbone, attached to two fatty acid (aliphatic groups) esters and an alkyl phosphate. Suitable phospholipids for use in this invention include, without limitation, dimyristoyl phosphatidylcholine, distearoyl phosphatidylcholine, dilinoleoyl-phosphatidylcholine (DLL-PC), dipalmitoyl-phosphatidylcholine (DPPC), soy phophatidylchloine (Soy-PC or PCs) and egg phosphatidycholine (Egg-PC or PCE). Suitable phospholipids also include, without limitation, dipalmitoyl phosphatidylcholine, phosphatidyl choline, or a mixture thereof. Exemplified below are 1,2-dipalmitoyl-sn-glycero-3 phosphoethanolamine phospholipid and 1,2-Distearoyl-sn-Glycero-3-Phosphoethanolamine.

The term "stable" means a solution or suspension in a fluid phase wherein solid components (i.e., nanotubes and drugs) possess stability against aggregation sufficient to allow manufacture and delivery to a cell and which maintain the integrity of the compound for a sufficient period of time to be detected and preferably for a sufficient period of time to be useful for the purposes detailed herein. The present complexes are "dispersed" in that they are soluble or form stable suspensions. They may contain some degree of nanoparticle aggregation, but are sufficiently individualized such that they may readily be formed in such preparations, as opposed to continuous sheets or clumps of such complexes.

The term "soluble" refers to solubility in water or aqueous medium, including physiological fluids, which are salty and contain other components. It is not intended to require that 100% of the "soluble" nanoparticles be in solution, or that the particles be in a true solution, or that they remain in solution for a lengthy period of time. It is required that they remain in stable suspension, without settling or clumping, and, preferably for at least about 30 days.

The term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds.

In a broad aspect, the permissible substituents include acyclic and cyclic, branched and unbranched, carbocyclic and heterocyclic, aromatic and non-aromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example, of cancer.

The term "supramolecular bonding" is used in a conventional sense to mean noncovalent bonding interactions of molecules. Traditional organic synthesis involves the making and breaking of covalent bonds to construct a desired molecule. In contrast, supramolecular chemistry utilizes far weaker and reversible noncovalent interactions, such as hydrogen bonding, metal coordination, hydrophobic forces, van der Waals forces, pi-pi interactions, and/or electrostatic effects to assemble molecules into multimolecular complexes. It is used to build molecularly defined, organic assemblies in two or three dimensions via non-covalent interactions between the constituents. Conventionally, supramolecular bonding has been associated with self-assembling complexes, as described, e.g., in U.S. Pat. No. 5,714,167 to Milstein, et al., issued Feb. 3, 1998, entitled "Active agent transport systems." However, in the present case, the bonding of the aromatic molecule to the nanostructure does not involve self-assembly of the nanostructures, as the hydrophilic polymers attached either through covalent bonding or supramolecular functionalization (i.e., hydrophobic interaction between an aliphatic lipid and the hydrophobic nanoparticle) prevent nanotube aggregation. In particular, the supramolecular bonding used in the preferred embodiment involves hydrophobic forces and pi bonding.

The term "targeting agent" means a molecule, which is a specific ligand for a cell surface protein, and can be coupled to the present nanoparticle complex without rendering the complex insoluble or preventing release of the attached drug. The targeting agent is preferably linked to the hydrophilic polymer, e.g., through an amine terminus on a PEG molecule. The exemplified targeting agent is a cyclic RGD peptide, as described, for example, in U.S. Pat. No. 5,192,746 to Lobl, et al., issued Mar. 9, 1993, entitled "Cyclic cell adhesion modulation compounds," and in "Cyclic RGD Peptide-Labeled Liposomes for Targeting Drug Therapy of Hepatic Fibrosis in Rats," *J Pharmacol Exp Ther.* 2007 May 17 (E_PUB).

Other examples of targeting agents include the 14 amino acid peptide bombesin, as described for example in Ma et al., "In Vitro and In Vivo Evaluation of Alexa Fluor 680-Bombesin[7-14]NH(2) Peptide Conjugate, a High-Affinity Fluorescent Probe with High Selectivity for the Gastrin-Releasing Peptide Receptor," *Mol Imaging*, 2007 July-September; 6(3): 171-80. The 12 amino acid peptide FROP1 was identified by phage screening, as other targeting agents useful here may be. See, Zitzmann et al., "Identification and Evaluation of a New Tumor Cell-Binding Peptide, FROP-1," *J Nucl Med.* 2007 June; 48(6):965-972. Epub 2007 May 15.

The present targeting agents may also include antibodies and antibody fragments, such as Affibody® molecules, 58-amino acid three-helix bundle proteins directed to different targets by combinatorial engineering of staphylococcal protein A.

The term "antibody" includes antibodies obtained from both polyclonal and monoclonal preparations, as well as: hybrid (chimeric) antibody molecules (see, for example, Winter et al. (1991) *Nature*, 349:293-299; and U.S. Pat. No. 4,816,567); F(ab')2 and F(ab) fragments; Fv molecules (non-covalent heterodimers, see, for example, Inbar et al. (1972) *Proc Natl Acad Sci USA*, 69:2659-2662; and Ehrlich et al. (1980) *Biochem*, 19:4091 4096); single-chain Fv molecules (sFv) (see, for example, Huston et al. (1988) *Proc Natl Acad Sci USA*, 85:5879-5883); dimeric and trimeric antibody fragment constructs; minibodies (see, e.g., Pack et al. (1992) *Biochem*, 31:1579-1584; Cumber et al. (1992) *J Immunology*, 149B: 120-126); humanized antibody molecules (see, for example, Riechmann et al. (1988) *Nature*, 332:323-327; Verhoeyan et al. (1988) *Science*, 239:1534-1536; and U.K. Patent Publication No. GB 2,276,169, published 21 Sep. 1994); and, any functional fragments obtained from such molecules, wherein such fragments retain specific-binding properties of the parent antibody molecule. Exemplary targeting antibodies include antibodies to cellular receptors such as the HER-2 or EGF receptor, as well as antibodies to cell surface cluster determinant ("CD") antigens, such as CD20. Other antibody targets include alpha fetal protein, CA-125, HLA and other antigens.

Other targeting agents which recognize particular cell types include, e.g., VEGF, which binds to VEGF receptors, or folic acid, which binds to particular receptors. Analogs of folic acid with these same properties are known and may also be used. Analogs are discussed in Roos et al., "Toxicity of Folic Acid Analogs in Cultured Human Cells: A Microtite Assay for the Analysis of Drug Competition," *PNAS*, Jul. 15, 1987, vol. 84, no. 14, 4860-4864. Certain tumor cells over express the folic acid receptor.

The present targeting agents may also be used for intracellular targeting to a specific organelle such as a nuclear membrane.

General Methods and Materials

Described below are methods and materials involving supramolecular chemistry (Lehn, J. M., "Supramolecular chemistry: receptors, catalysts, and carriers," *Science*, 1985, 227, (4689), 849) for the assembly of molecules on SWNTs pre-functionalized non-covalently or covalently by common surfactant or acid-oxidation routes. Aqueous soluble SWNTs with polyethylene-glycol (PEG) functionalization by these routes allow for $\pi$-stacking of various aromatic molecules, including a chemotherapy cancer drug doxorubicin with an ultrahigh loading capacity of ~400% by weight, a widely used fluorescence molecule fluorescein and combinations of molecules. Binding and releasing of molecules on nanotubes exhibit novel diameter dependence and can be controlled by pH. Based on optical absorbance data and molar extinction coefficients of doxorubicin (DOX) and SWNTs, the present methods are shown to produce ~50 DOX molecules bound to each 10 nm length of SWNT, corresponding to a high weight ratio of ~4:1 between DOX and nanotube. Radio-labeling was used to estimate the number of PEG functionalization (on both PL-PEG-SWNT and PEG-OXNT) to be ~3 per 10 nm of SWNT length. These suggested ~10% of the SWNT surface area was occupied by phospholipid molecules with extended PEG chains while ~70-80% was complexed with DOX. Similar degrees of PEGylation and DOX loading were observed with PEG-OXNT (oxidized nanotubes). It was shown that a certain degree of coverage of PEG chains on nanotubes was both necessary and sufficient to impart aqueous solubility of SWNTs without aggregation (especially for stability in high salt solutions and biological solutions such as serum. Furthermore, it is shown that unoccupied surface areas on functionalized SWNTs were useful for binding of other molecules. We suggest that non-covalent binding of DOX on SWNTs most likely occurred via $\pi$-stacking and hydrophobic interactions due to the aromatic nature of the DOX molecule and relatively low solubility of deprotonated DOX at basic condition. Free unbound DOX exhibited high fluorescence, while much weaker fluorescence was observed for DOX after binding to SWNTs. This high degree of fluorescence quenching is evidence of $\pi$-stacked DOX, similar to other aromatic molecules $\pi$-stacked onto nanotubes. Thus there is described a way to attach drugs to nanomaterials in a manner unique to carbon nanotubes owing to the extended polyaromatic sidewalls of these materials. Notably, in control experiments, we found that DOX alone was incapable of solubilizing pristine SWNTs in water, and nor did we find DOX replacing phospholipid molecules on SWNTs to any significant degree.

Given the present description, one can thus substitute other nanoparticles for the exemplary SWNTs.

The amount of doxorubicin bound onto SWNTs was pH dependent, decreasing from a loading factor of ~4 (defined as DOX/SWNT weight ratio ~4) to ~2 and ~0.5 as pH was reduced from 9 to 7 and 5 (FIGS. 3A, 3B and 3C). This trend may be attributed to the increased hydrophilicity and higher solubility of DOX at lower pH caused by increased protonation of the —NH2 group on DOX, thereby reducing the hydrophobic interaction between DOX and SWNTs. In terms of releasing, we found that DOX stacked on SWNTs remained stably bound in basic buffer solutions, in physiological buffers and serum at pH=7.4 (FIG. 3D) at room temperature.

However, in an acidic pH of 5.5, we observed appreciable release of DOX from Hipco SWNTs by ~40% in 1 day (FIG. 3D), attributed to the increased hydrophilicity and solubility of DOX at this pH. The pH dependent drug releasing from SWNTs could be exploited for drug delivery applications since the micro-environments of extra-cellular tissues of tumors and intra-cellular lysosomes and endosomes are acidic, potentially facilitating active drug release from SWNT delivery vehicles. In this case, the active agent is favorably dissociated at low pH so that the active agent is delivered to a desired cellular environment having a lower pH.

See for example S Matsuyama and J C Reed, "Mitochondria-dependent apoptosis and cellular pH regulation," *Cell Death and Differentiation*, December 2000, Volume 7, Number 12, Pages 1155-1165 and Yatvin et al., "Temperature- and pH-sensitive liposomes for drug targeting," *Methods Enzymol.*, 1987; 149:77-87. Dissociation in low pH tumor tissue by a different mechanism is described in U.S. Pat. No. 4,997,913 to Hellstrom, et al. Mar. 5, 1991, entitled "pH-sensitive immunoconjugates and methods for their use in tumor therapy."

Figure 4A:
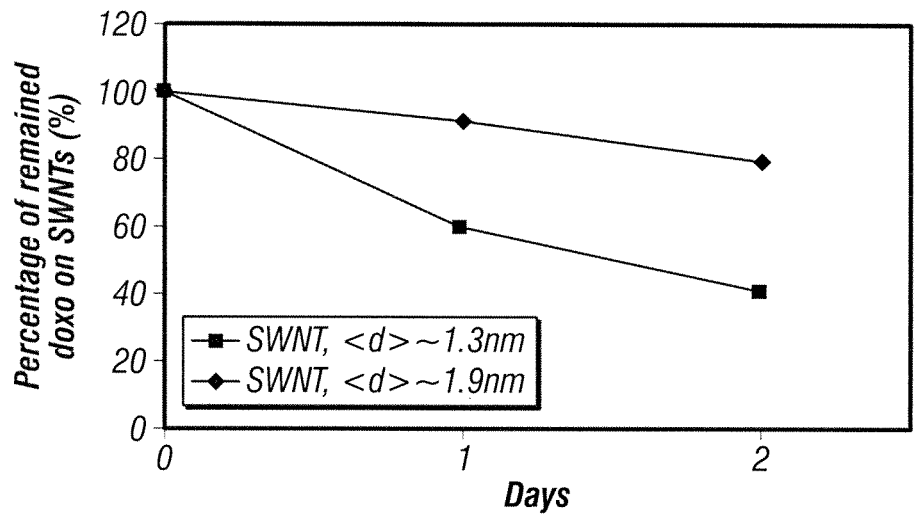
FIG. 4A shows doxorubicin releasing curves from Hipco SWNTs and laser-ablation SWNTs at an acidic pH=5.5.
Figure 4B:
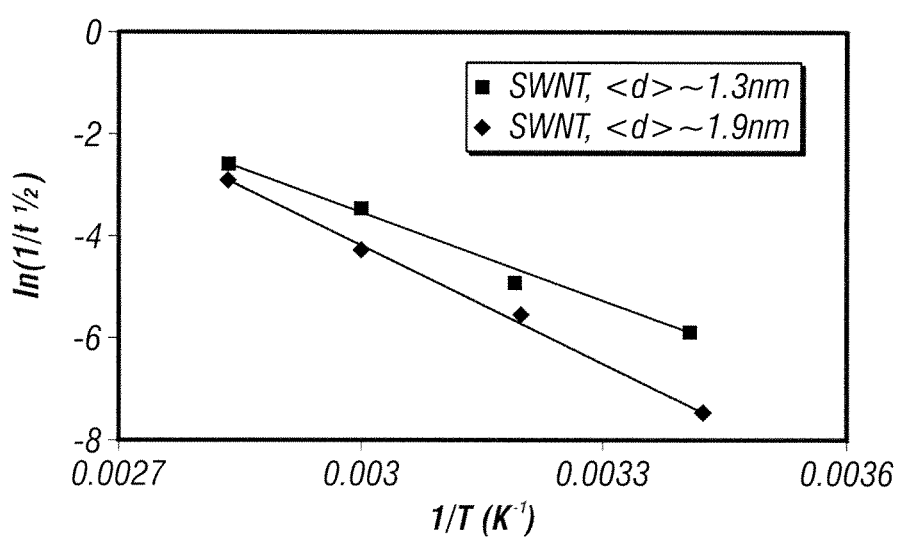
FIG. 4B shows the half life ($t\frac{1}{2}$) of doxorubicin on PL-PEG functionalized Hipco and laser SWNTs, respectively, at various temperatures from 20-80° C. at pH=7.4. Solid lines are Arrhenius fits of $1/t\frac{1}{2}(T)=A\times\exp(-EB/kBT)$ where A is a constant for extracting binding energy EB of doxorubicin (DOX) on nanotubes.

Furthermore, when using larger diameter laser-ablation grown SWNTs (mean d~1.9 nm) rather than Hipco material (d~1.3 nm) (FIG. 4A), we observed obviously slower releasing of DOX (at the same pH=5.5) than from Hipco tubes (FIG. 4B). We heated up the SWNT-DOX solutions to measure temperature dependent release rate and half-life $t_{1/2}$ and found shorter $t_{1/2}$ or more rapid DOX release from SWNT surfaces at higher temperatures. This difference may be conceptualized as stronger π-stacking of aromatic molecules onto larger tubes with flatter graphitic sidewalls. Thus, by choosing SWNTs of a specific diameter, one can tailor the molecular binding strength on SWNTs to vary the release rate and suit different applications.

As further described below, SWNTs without any DOX loading (PL-SWNT) exhibited no toxic effect to cells. DOX loaded SWNTs (PL-SWNT-DOX) induced significant U87 cancer cell death and cell apoptosis similar to free DOX at a DOX concentration of 10 μM.

Figure 5:
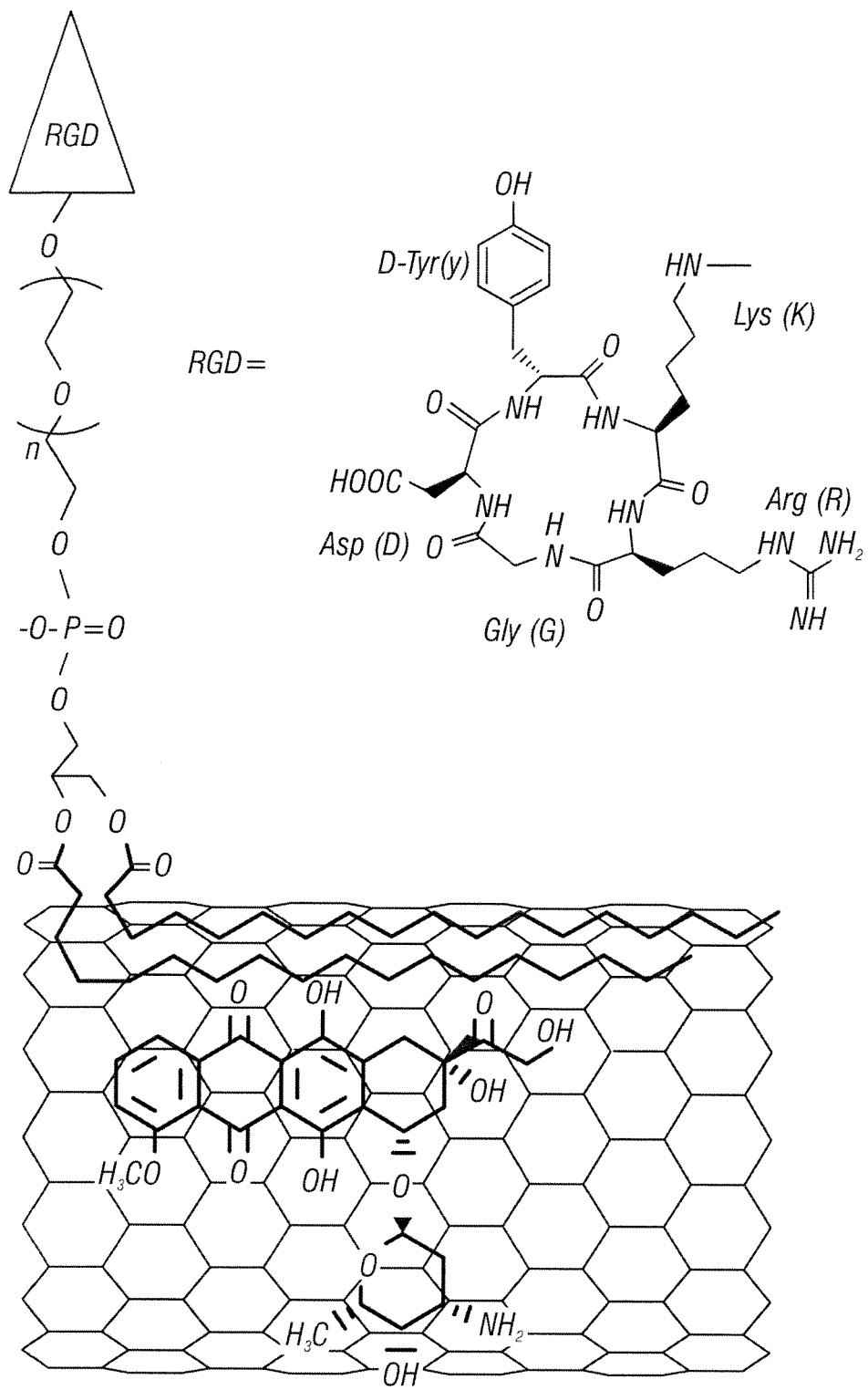
FIG. 5 is a diagram showing a schematic structure of PL-SWNT-RGD-DOX, i.e., SWNTs functionalized with RGD covalently linked to a terminus of PEG (lipid at the other terminus) and where the nanotube is loaded with doxorubicin on the sidewall by π-stacking. The structure of RDG is also shown.
Figure 6A:
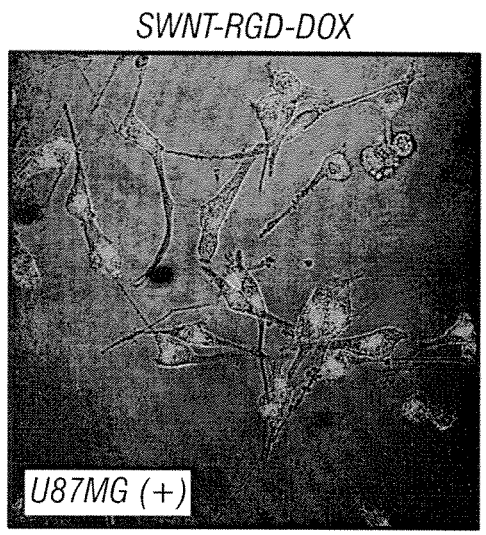
FIG. 6A-D is a series of four confocal fluorescence images of integrin $\alpha_v\beta_3$ positive U87MG cells (A, B) and negative MCF-7 cells (C, D) treated with either PL-SWNT-DOX (right) or PL-SWNT-RGD-DOX (left). The concentration of DOX was 2 μM in all experiments. The U87MG cells incubated with PL-SWNT-RGD-DOX showed stronger DOX fluorescence in the cells than in the other three cases.
Figure 6B:
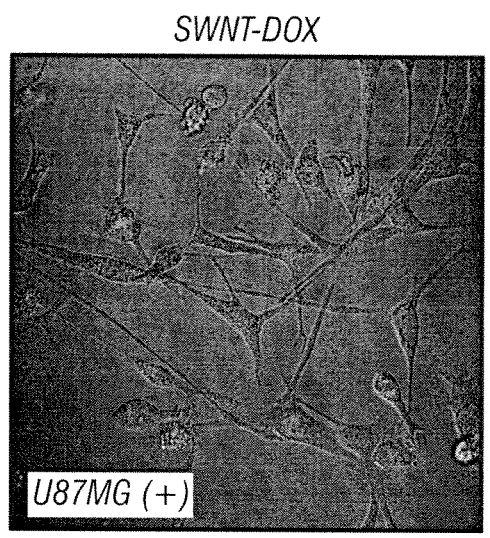
Figure 6C:
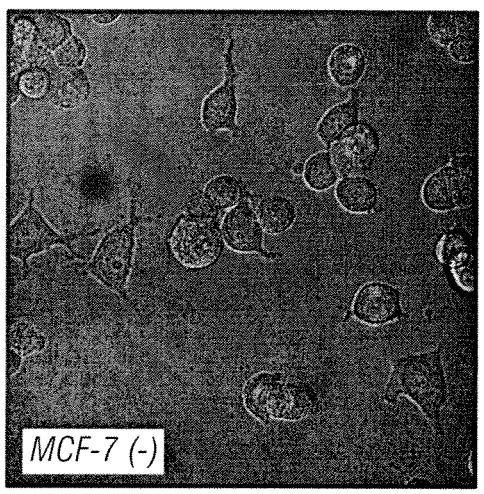
Figure 6D:
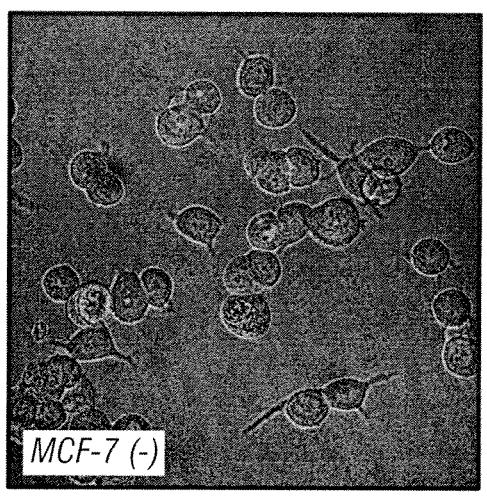
Figure 7A:
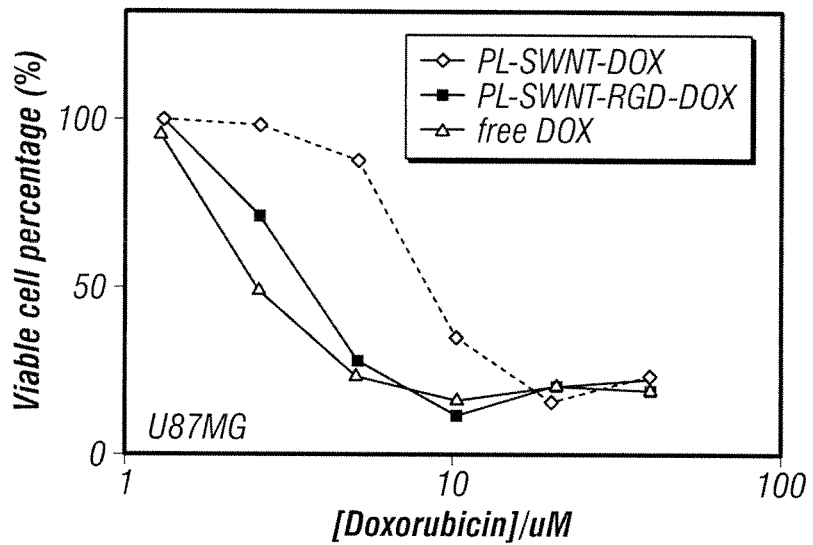
FIGS. 7A and 7B are graphs showing concentration dependent survival curves of U87MG cells (4C) and MCF-7 cells (7B) treated by various samples indicated (PL-SWNT-DOX, PL-SWNT-RGD-DOX or free DOX). The viable cell percentage was measured by the MTS assay. PL-SWNT-DOX had relatively lower toxic effect than free DOX to both types of cells while PL-SWNT-RGD-DOX exhibited increased toxicity to U87MG cells but not to MCF-7 cells.
Figure 7B:
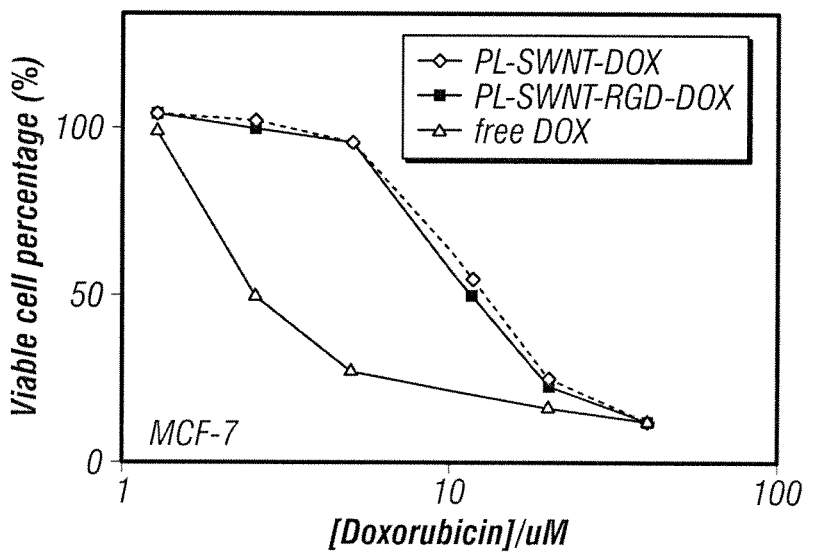

Also described below is the conjugation of a cyclic RGD (as shown in FIG. 5) on the terminal groups of PEG on SWNTs, imparting a recognition moiety for integrin $\alpha_v\beta_3$ receptors, which are up-regulated in a wide range of solid tumors. Ultra-high DOX loading was observed on PEG-RDG functionalized SWNTs, without any loss of capacity due to the added RGD. Enhanced doxorubicin delivery to integrin $\alpha_v\beta_3$ positive U87MG cells by RGD conjugated SWNTs was evidenced (FIG. 6A-D). The PL-SWNT-RGD-DOX showed enhanced cell killing effect to U87MG cells with a lower IC50 value (~3 μM) than prior to RGD conjugation (~8 μM), owing to specific RGD-integrin recognition and enhanced cellular uptake of the SWNT-drug (FIG. 7A). In contrast, for integrin $\alpha_v\beta_3$ negative MCF-7 cells, RGD conjugation onto SWNT-DOX gave no obvious enhancement in intracellular DOX delivery. Concentration dependent toxicity data showed that free DOX exhibited higher toxicity than both PL-SWNT-DOX and PL-SWNT-RGD-DOX to MCF cells (FIG. 7B), suggesting RGD conjugation to SWNTs afforded no enhancement in DOX delivery and destruction of integrin $\alpha_v\beta_3$ negative MCF cells. These results suggested the potential of selectively enhancing the toxicity of drugs to certain type of cells by using SWNTs conjugated with a targeting moiety as drug carriers.

Also described below are specific examples showing that molecular binding and adsorption onto SWNTs is general to several types of aromatic molecules. These data include a fluorescent dye molecule fluorescein (Nakayama-Ratchford, N.; Bangsaruntip, S.; Sun, X. M.; Welsher, K.; Dai, H. J., Noncovalent functionalization of carbon nanotubes by fluorescein-polyethylene glycol: Supramolecular conjugates with pH-dependent absorbance and fluorescence. *J. Am. Chem. Soc.*, 2007, 129, (9), 2448-2449) and other chemotherapy drugs (daunorubicin, SN38), though the degree of loading on SWNTs and pH dependence varied for different molecules. Fluorescein derivative fluorescein cadaverine (FITC-NH$_2$, Molecular Probes) was loaded onto PEG-SWNTs with high efficiency at the isoelectric pH (pI~6) of fluorescein. About 40 FITC molecules were loaded per 10 nm length of SWNT (vs. ~50 DOX per 10 nm of SWNT loaded at pH 9). FITC was released from PL-SWNTs at high pHs due to increased hydrophilicity resulting from deprotonation of the carboxylic acid group on the molecule. These results suggest that various types of small aromatic and hydrophobic molecules with low water solubility can be loaded onto the surface of SWNTs in aqueous phase via non-covalent π-interaction. Such interaction is sufficiently strong against rapid desorption in normal physiological conditions. Molecular releasing of the non-covalently bound molecules can be triggered by environmental changes such as pH or using other external stimuli.

Nanoparticles

The present carbon nanotubes may be made by a variety of processes including those made by arc discharge, laser ablation, chemical vapor deposition (CVD) and Hipco. Hipco is the High-pressure CO disproportionation process for catalytic production of SWNTs in a continuous-flow gas phase using CO as the carbon feedstock and Fe(CO)$_5$ as the iron-containing catalyst precursor. SWNTs are produced by flowing CO, mixed with a small amount of Fe(CO)$_5$, through a heated reactor. Size and diameter distribution of the nanotubes can be roughly selected by controlling the pressure of CO.

Other known manufacturing processes can be used. Carbon nanotubes are generally produced by three main techniques, arc discharge, laser ablation and chemical vapor deposition. In arc discharge, a vapor is created by an arc discharge between two carbon electrodes with or without catalyst. Nanotubes self-assemble from the resulting carbon vapor. In the laser ablation technique, a high-power laser beam impinges on a volume of carbon-containing feedstock gas (methane or carbon monoxide). At the moment, laser ablation produces a small amount of clean nanotubes, whereas arc discharge methods generally produce large quantities of impure material. In general, chemical vapor deposition (CVD) results in MWNTs or poor quality SWNTs. The SWNTs produced with CVD have a large diameter range, which can be poorly controlled. But on the other hand, this method is very easy to scale up.

Multiple walled nanotubes can be made by chemical vapor deposition or arc discharge. Size-controlled, soluble SWNTs are described, for example in Czerw, et al., "Organization of Polymers onto Carbon Nanotubes: A route to Nanoscale Assembly," NanoLetters, 1(8):4230427 (2001).

Another aspect of the present nanotubes is that they are controlled in size and aggregation (i.e., bundling). The sizes are between 50 and 500 nm in length, and clumps are between a single tube (~1 nm) to clumps of 5 nm. This is done by rinsing and sonication, as described in detail below. The specific steps described may be routinely varied in time, temperature, concentration, etc. in accordance with the present teachings. The nanotube rinsing and sonication provides a stable nanotube suspension. In a preferred process, the nanotubes are optionally refluxed in very low pH (<2) oxidizing acid, sonicated to cut the nanotubes into short segments, refluxed in strong acid again and filtered, rinsed and resuspended and reacted in suspension with the linking agent. Oxidation, if used, is adjusted to produce about 0.5 to 2 oxidized sites per nm length of nanotube.

Graphene coated nanocrystals may be prepared as described in Nature Materials, 5, 971-976 (2006). In addition, the present nanoparticles may be prepared as graphene sheets, either in the form of graphite oxide or graphene sheets. The sheets may be only a single atomic layer deep, and are controlled as to their two dimensions.

Functionalization with Hydrophilic/Amphiphilic Polymers

Aqueous solutions of Hipco SWNTs (mean diameter d~1.3 nm and length~200 nm) were functionalized non-covalently by a surfactant of phospholipids-PEG (~120 polyethylene-oxide PEO units)[3, 7] or covalently by PEGylation (~220 PEO units) of —COOH groups on SWNTs generated by refluxing in 2.6M nitric acid[8].

Supramolecular Bonding of Aromatic Molecules to Functionalized Nanoparticles

Figure 1B:
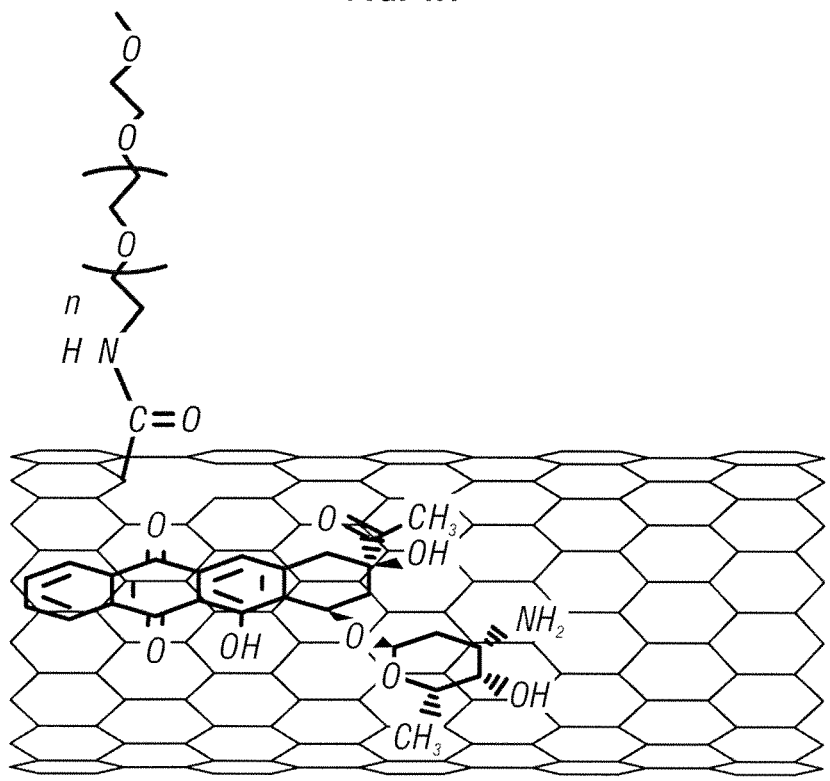
FIG. 1B shows covalent PEGylation where a PEG is covalently attached to a nanotube sidewall which contains a —COOH group.
Figure 2A:
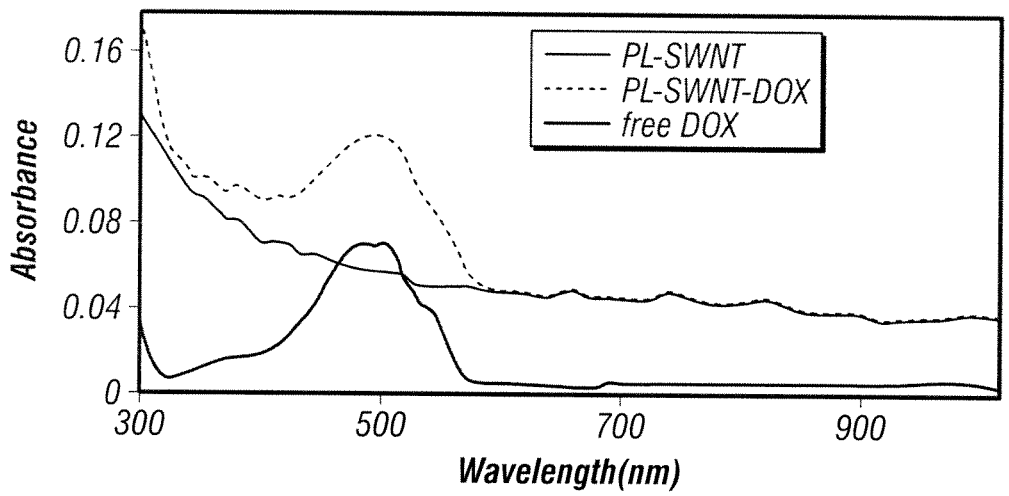
FIG. 2A is a plot showing UV-Vis-NIR absorbance spectra of solutions of free doxorubicin, SWNTs with PL-PEG functionalization, and PL-PEG SWNTs complexed with doxorubicin.
Figure 2B:
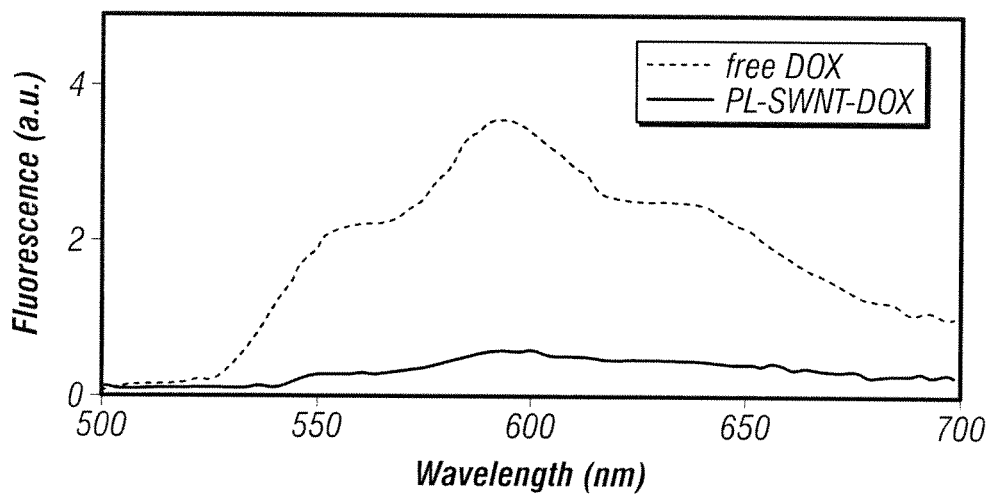
FIG. 2B shows fluorescence spectra of solutions of free doxorubicin and doxorubicin bound to SWNTs with PL-PEG functionalization (excitation at 488 nm) with the same doxorubicin concentration.

After simple mixing of PEG-SWNT solution with doxorubicin (DOX) at pH=9 overnight and then repeated filtering to remove free DOX in solution, we observed the formation of bound SWNT-DOX complexes for both phospholipid (PL-SWNT) and oxidized SWNTs (OXNT) (FIG. 1). This was evidenced by a reddish color of the SWNT-DOX solutions due to adsorbed DOX and its characteristic UV-vis absorbance peak at 490 nm (FIG. 2A). While free unbound DOX exhibited high fluorescence, much weaker fluorescence was observed for DOX bound to SWNTs (FIG. 3B) due to quenching. SWNTs were observed to increase in average diameter when imaged by atomic force microscopy (AFM) after DOX loading (data not shown). Based on optical absorbance data and molar extinction coefficients of DOX and SWNTs, we estimated ~50 DOX molecules bound to each 10 nm length of SWNT (see below), corresponding to a high weight ratio of ~4:1 between DOX and nanotube.

Binding of Drugs to Solubilized Nanoparticles

Figure 8A:
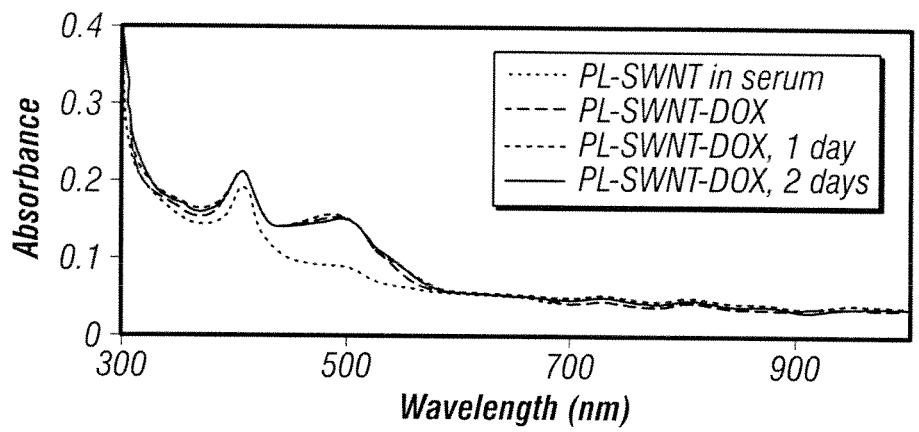
FIG. 8 A-C shows UV-VIS-NIR spectra of (8A) PL-SWNT-DOX and (8B) OXNT-DOX before and after incubation in serum for 1 and 2 days. Any detached DOX was removed by filtration. Note that the peak at ~400 nm was due to serum proteins in the solution. The broad peak around ~490 nm was due to DOX on the nanotubes.
FIG. 8C shows doxorubicin releasing curves of PL-SWNT-DOX and OXNT-DOX in serum.
Figure 8B:
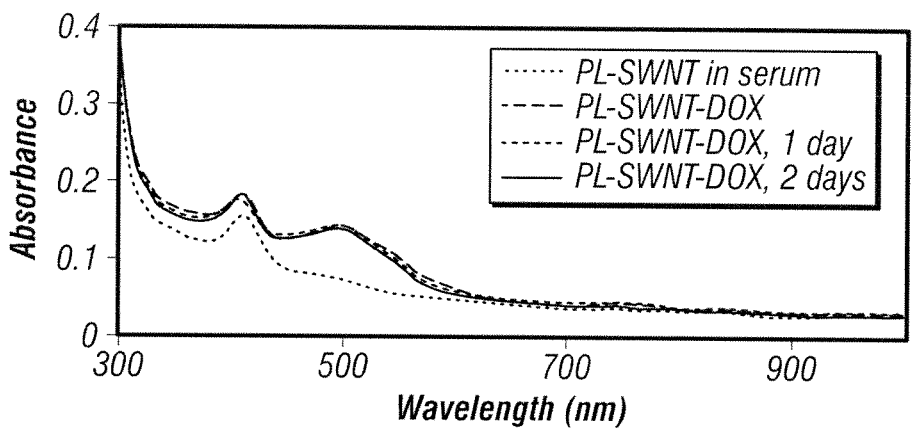
Figure 9:
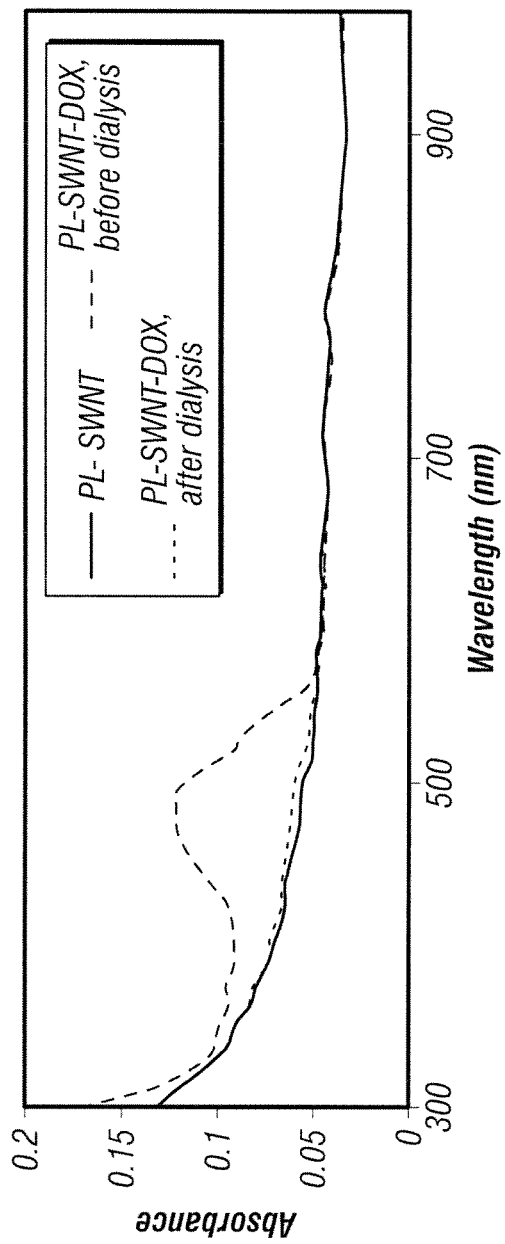
FIG. 9 is a graph showing UV-VIS-NIR spectra of PL-SWNT (no DOX loading), PL-SWNT-DOX before dialysis and PL-SWNT-DOX after dialysis at pH4 for 3 days.

While a certain coverage of PEG chains was both necessary and sufficient to impart aqueous solubility of SWNTs without aggregation especially in biological solutions such as serum[3] (FIG. 8A, 8B), our results suggested that unoccupied surface areas on PEG-coupled SWNTs were ample and useful for supramolecular binding of DOX and other aromatic molecules. Without wishing to be bound by any scientific theory, it is believed that the observed binding of DOX on SWNTs occurred most likely via π-stacking[9, 10] and hydrophobic interactions, forming a forest (PEG)-scrub (DOX) structure on SWNTs. This represented a partition and utilization of SWNT sidewalls, which involved both hydrophilic functionalization and aromatic pi bonding functionalization. We estimated that ~10% of the SWNT surface area was occupied by phospholipid molecules with extended PEG chains while ~70-80% was complexed with DOX (data not shown). Also, we did not find DOX replacing the PL-PEG molecules on SWNTs (FIG. 9).

Figure 8C:
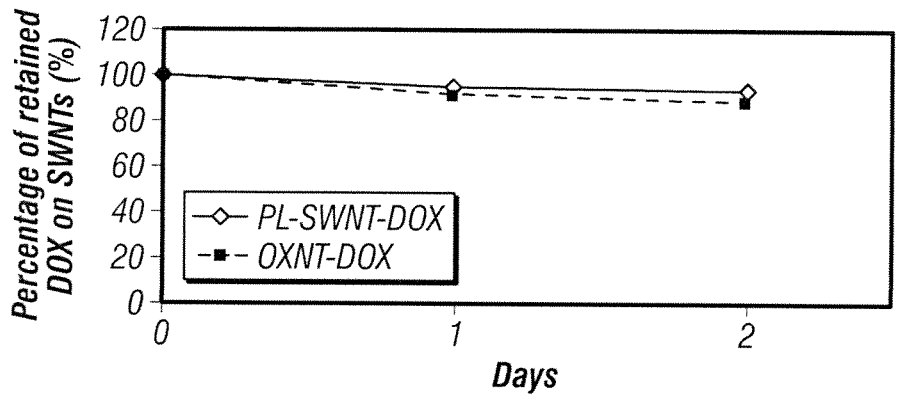

The binding and loading efficiency of DOX on SWNTs was found to be pH dependent, decreasing from a factor of ~4 (DOX/SWNT weight ratio) to ~2 and ~0.5 as pH decreased from 9 to 7 and 5 (FIG. 3C). This was attributed to the increased hydrophilicity and solubility of DOX at lower pH due to increased protonation of the —NH$_2$ group on DOX, thereby reducing the hydrophobic interaction with SWNTs. In terms of releasing, we found that DOX densely packed on SWNTs at pH=9 remained stably bound in physiological buffers and serum at pH=7.4 at room temperature (FIG. 3D and FIG. 8). In an acidic pH of 5.5, we observed more rapid release of DOX from Hipco SWNTs by ~50% in 1 day (FIG. 3D). The pH controlled releasing could be ideal for potential drug delivery since the micro-environments of extra-cellular tissues of tumors are acidic, which can facilitate active drug release from SWNT delivery vehicles. Acidity characterizes the environment of cells that are partially starved for oxygen, such as highly proliferative cancer cells or macrophages at sites of inflammation and infection. Almost all solid tumors develop an acidic environment, known as the Warburg effect (Nobel Prize, 1931).

Figure 10A:
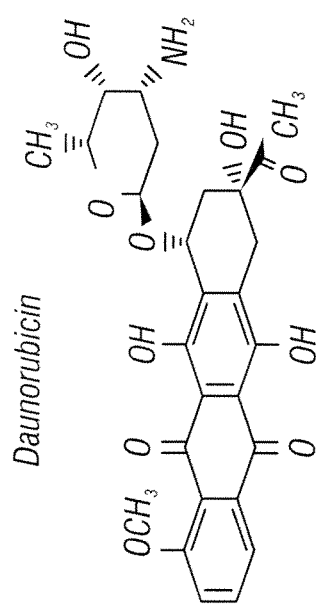
FIGS. 10A and 10B are structures of daunorubicin (10A) and fluorescein-NH2 (10B) and, to the right of each structure is a graph showing loading of daunorubicin (10A) and fluorescein (10B) on SWNTs. UV-VIS-NIR spectrums were taken after excess small molecules were removed by filtration and washing with water.
Figure 10A:
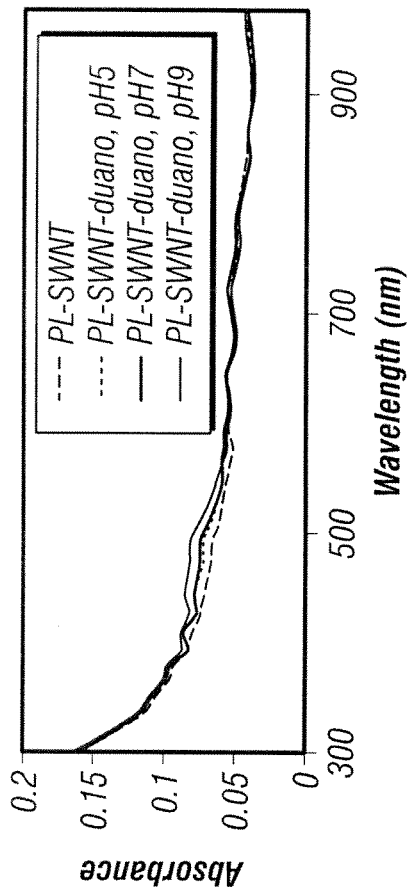

The examples demonstrate that supramolecular chemistry is general on various types of water solubilized SWNTs for several aromatic molecules tested, though the efficiency varies depending on the structure of molecules and pH. Notably, the acid-reflux covalent oxidation used here is perhaps the most widely used covalent functionalization scheme for SWNTs[8, 11], and the identification of ample surface area on these nanotubes for supramolecular chemistry was unexpected. Importantly, the supramolecular approach allows for loading multiple active aromatic molecules onto SWNTs, as illustrated by binding DOX and fluorescein (FITC) at different pHs successively (FIGS. 10-11). Thus, we can now readily obtain one-dimensional assemblies with various functional aromatic molecules non-covalently populating SWNT sidewalls and a small percentage of strongly bound PEG imparting aqueous solubility of the assembly.

EXAMPLES

Example 1

Preparation of Nanotube Materials for Improved Solubilization

Non-covalent functionalized SWNTs were prepared as follows (see, Kam, N. W. S.; Liu, Z.; Dai, H. J., Functionalization of carbon nanotubes via cleavable disulfide bonds for efficient intracellular delivery of siRNA and potent gene silencing. J. Am. Chem. Soc., 2005, 36, 12492-12493): As-grown Hipco or laser-ablation SWNTs were sonicated in aqueous solution of PL-PEG$_{5400}$-NH$_2$ for 1 h followed by centrifugation at 24,000 g for 6 h, yielding well suspended SWNTs (mostly individual SWNTs) in the supernatant. Unbound surfactant was thoroughly removed by repeated filtration through 100 KDa filters (Millipore) and re-suspending SWNTs in water by sonication. The PL-PEG functionalized SWNTs were finally re-suspended in phosphate buffer saline (PBS).

Covalently functionalized SWNTs were prepared by refluxing as-grown Hipco SWNTs in 2.5M nitric acid for 24 h. Acid was thoroughly removed by repeated filtration through 100 nm polycarbonate membrane (Millipore) and re-suspension in water. PEGylation of carboxylic acid groups on the oxidized SWNTs were done by adding 1 mM of 4-armed polyethylene glycerol-amine (Aldrich) into the OXNT (Oxidized nanotube) solution in the presence of 2 mM 1-ethyl-3-[3-dimethylaminopropyl]carbodiimide hydrochloride (EDC, Aldrich) under gentle sonication. After overnight reaction, unreacted reagents were removed by repeated filtration and re-suspension of the covalently PEGylated SWNTs.

Both the PL-PEG non-covalently functionalized and covalently PEGylated oxidized SWNTs were well solubilized and stable in water, PBS and cell medium containing 10% of fetal calf serum and full serum. Atomic force microscopy was used to measure the diameter and length of the functionalized SWNTs after deposition on a Si substrate.

Example 2

Supramolecular Assembly of Doxorubicin onto Solubilized SWNTs

DOX was attached to nanoparticles functionalized with lipid-PEG. SWNTs (PL-PEG-SWNT or PEG-OXNT) were mixed with 1 mM of DOX at a nanotube concentration of ~0.05 mg/ml at various pHs overnight. Unbound excess DOX was removed by filtration through a 100 kDa filter and washed thoroughly with water (over 10 times) and phosphate buffered saline (PBS) until the filtrate became free of reddish color (DOX). SWNT-DOX complexes thus formed were re-suspended and stored at 4° C.

UV-Vis-NIR absorbance spectra of the SWNT-DOX complexes were measured by a Cary-6000i spectrophotometer. The concentration of SWNTs was determined by the absorbance at 808 nm with a molar extinction co-efficient of $7.9 \times 10^6$ $M \cdot cm^{-1}$ for PL-PEG functionalized SWNTs and $4.0 \times 10^6$ $M \cdot cm^{-1}$ for the oxidized SWNTs for average tube length of 200 nm. (See Kam, N. W. S.; O'Connell, M.; Wisdom, J. A.; Dai, H. J., Carbon nanotubes as multifunctional biological transporters and near-infrared agents for selective cancer cell destruction. *PNAS* 2005, 102, 11600-5, and Liu, Z.; Cai, W. B.; He, L. N.; Nakayama, N.; Chen, K.; Sun, X. M.; Chen, X. Y.; Dai, H. J., In vivo biodistribution and highly efficient tumour targeting of carbon nanotubes in mice. *Nature Nanotechnology*, 2007, 2, (1), 47-52).

Concentration of DOX attached to SWNTs was measured by the absorbance peak at 490 nm (characteristic of DOX, after subtracting the absorbance of SWNTs at that wavelength) with a molar extinction coefficient of $1.05 \times 10^5$ $M \cdot cm^{-1}$. Fluorescence spectra were taken by Fluorolog-3 fluorimeter for free DOX and DOX bound to SWNTs at an excitation of 488 nm.

Example 3

Analysis of Molecular Release from Nanotubes

Figure 12:
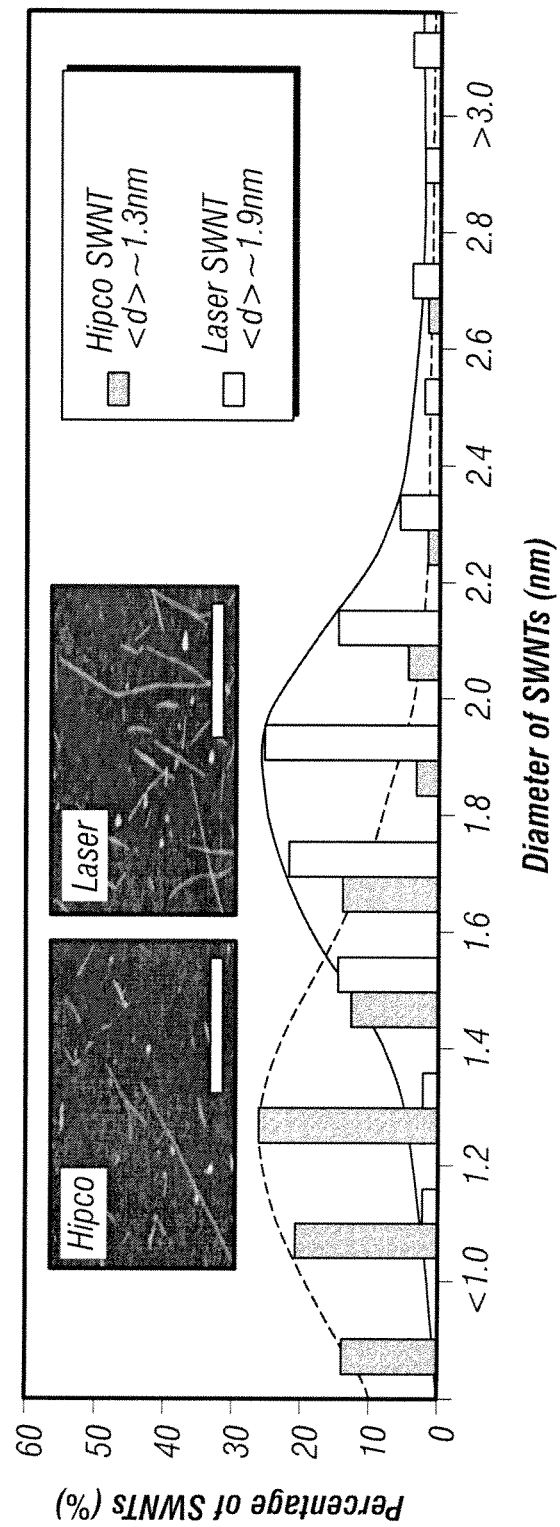
FIG. 12 shows diameter distributions of SWNTs in Hipco and laser-ablation materials respectively. Inset: atomic force microscopy (AFM) images of SWNTs in the two types of materials. Scar bar: 200 nm.
Figure 13A:
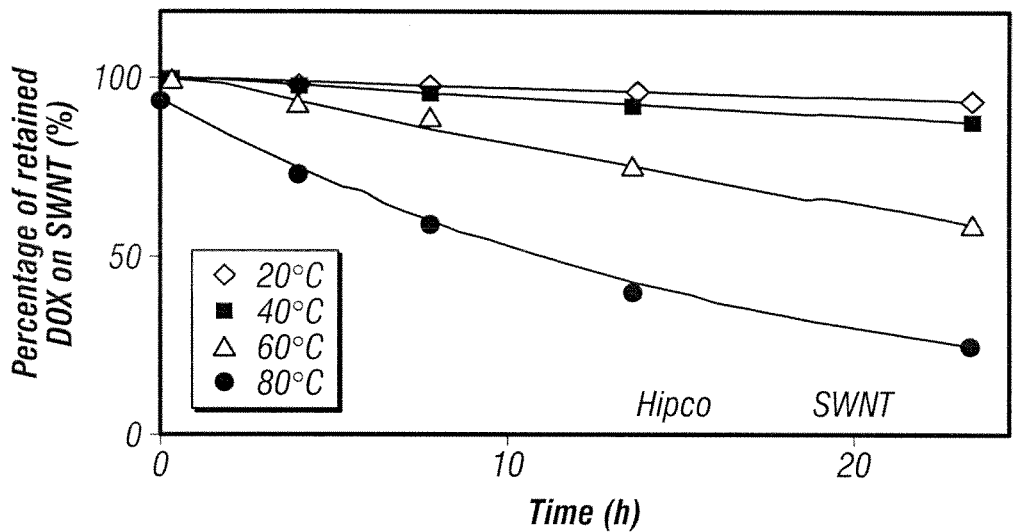
FIGS. 13A and 13B show temperature dependent doxorubicin releasing data (symbols) and exponential fits (solid lines) for (13A) Hipco PL-SWNT-DOX and (13B) Laser PL-SWNT-DOX.
Figure 13B:
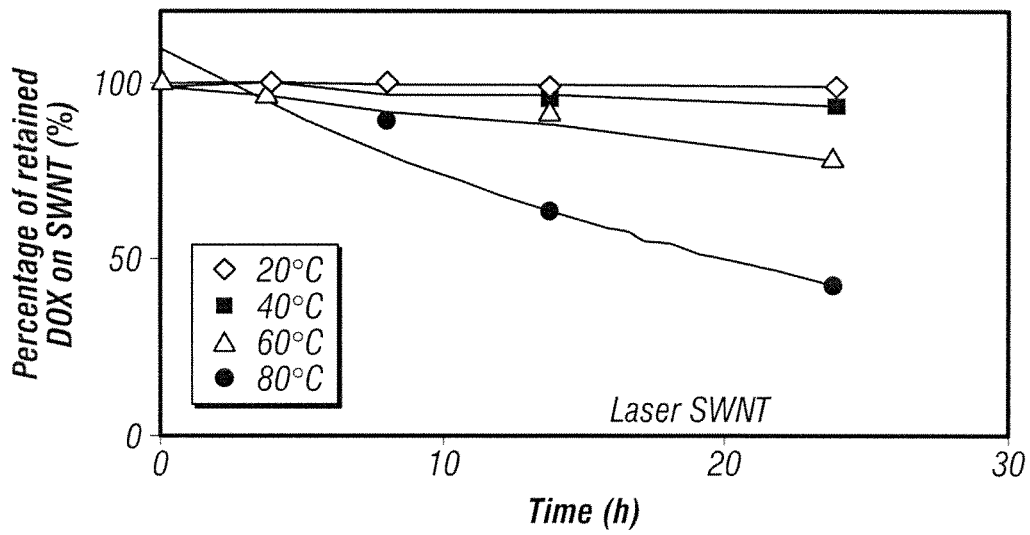

Solutions of PL-SWNT-DOX or OXNT-DOX complexes were incubated for various times at room temperature in PBS (pH=7.4) or acetate buffer (pH=5.5) with the same ionic strength adjusted by sodium chloride. DOX molecules detached from SWNT surfaces over time were removed from solution by filtration through 100 kDa filters. SWNTs were then re-suspended in water for UV-Vis-NIR measurement of the percentage of DOX retained (and thus released) on the nanotubes. For temperature dependent releasing, solutions of PL-SWNT-DOX complexes (for both Hipco and laser-ablation nanotubes) in PBS (pH=7.4) were kept at 20° C., 40° C., 60° C. and 80° C. respectively for various times. The released DOX was measured similarly at different time points to obtain retained DOX vs. time curves and half lives $t_{1/2}$ at various temperatures (FIGS. 12-13).

When using larger diameter laser-ablation grown SWNTs (mean d~1.9 nm) rather than Hipco material (d~1.3 nm), we observed obviously slower releasing of DOX (at pH=5.5) than from Hipco tubes (FIG. 4A). We heated up the solutions to measure temperature dependent release rate and half life $t_{1/2}$ (FIG. 4B and FIGS. 12-13) and estimated ~48 kJ/mol and ~59 kJ/mol binding energies for DOX on Hipco- and laser-SWNTs (at pH=7.4) respectively. This may be thought of as stronger π-stacking of aromatic molecules onto larger tubes with flatter graphitic sidewalls. Thus, by choosing SWNTs of a specific diameter, one can tailor the molecular binding strength on SWNTs to vary the release rate and suit different applications.

Example 4

RGD-PEG Functionalized SWNTs Taken Up by Cells

Doxorubicin is a widely used chemotherapy drug for treating various cancers. To demonstrate the power of supramolecular SWNT assembly, we conjugated a cyclic RGD peptide as shown in FIG. 5, having a lysine residue whose amino group is available for coupling. This peptide was linked to the terminal groups of PEG on SWNTs by linking the carboxylic group on RGD to the amine on PEG, imparting a recognition moiety for integrin $\alpha_v\beta_3$ receptors, which are up-regulated in a wide range of solid tumors[3]. Solutions of free DOX killed living cells non-discriminatively as expected. Under the same treatment condition, PL-SWNT-DOX without RGD appeared relatively low in toxicity (FIG. 6A, B), PL-SWNT-RGD-DOX were toxic selectively to integrin $\alpha_v\beta_3$ positive brain-cancer U87MG cells (owing to specific RGD-integrin recognition) and caused little death to integrin $\alpha_v\beta_3$ negative breast-cancer MCF-7 cells (FIG. 7A,B). This demonstrated the potential of targeted drug delivery using the supramolecular SWNT approach. Nanotubes were unique in affording ultrahigh molecular loading compared to liposome encapsulation[12] and dendrimer[13] approaches, molecular-scale diameters and one-dimensional shape. Combined with the ability of in vivo tumor targeting of SWNTs achieved in mice,[3] our current work of drug loading opens up the door of in vivo cancer therapy using nanotubes. Thus, the present supramolecular chemistry on SWNTs presents new opportunities in chemistry, biology and medicine.

RGD peptide was conjugated to PEGylated SWNTs as described previously. 1 mM of sulfo-SMCC (sulfosuccinimidyl 4-N-maleimidomethyl cyclohexane-1-carboxylate) was mixed with PL-SWNT with amine groups at PL-PEG termini (or OXNT with covalent attached PEG-NH$_2$) solutions at pH 7.4 for 2 h. Upon removal of excess reagents, the SWNTs were reacted overnight with 0.2 mM of thiolated RGD (See Liu, Z.; Cai, W. B.; He, L. N.; Nakayama, N.; Chen, K.; Sun, X. M.; Chen, X. Y.; Dai, H. J., In vivo biodistribution and highly efficient tumour targeting of carbon nanotubes in mice. *Nature Nanotechnology*, 2007, 2, (1), 47-52, and also Cai, W. B.; Shin, D. W.; Chen, K.; Gheysens, O.; Cao, Q. Z.; Wang, S. X.; Gambhir, S. S.; Chen, X. Y., Peptide-labeled near-infrared quantum dots for imaging tumor vasculature in living subjects. *Nano Lett.* 2006, 6, (4), 669) in the presence of 10 mM Tris(2-carboxyethyl)phosphine hydrochloride (TCEP) at pH 7.4, completing RGD conjugation to the terminal amine groups of PEG chains on SWNTs. DOX loading was then done at the same condition as for SWNTs without RGD with similar loading efficiencies observed. MCF-7 breast cancer cells and U87MG human glioblastoma cancer cells (both from American Type Culture Collection, ATCC) were cultured under standard conditions. Cell viability after various treatments was measured by the MTS assay with CellTiter96 kit (Promega).

Example 5

Estimation of Degree of PEGylation on the Starting Functionalized SWNTs

DOTA chelator for radiotracers was conjugated via EDC to the terminal amine groups on PL-PEG-NH$_2$ functionalized SWNTs (PL-SWNT) and PEGlyated oxidized SWNTs (OXNT) as described previously. The average number of DOTA chelators per SWNT was measured using a previously reported procedure with slight modifications. (See Meares, C. F.; McCall, M. J.; Reardan, D. T.; Goodwin, D. A.; Diamanti, C. I.; McTigue, M., Conjugation of antibodies with bifunctional chelating agents isothiocyanate and bromoacetamide reagents methods of analysis and subsequent addition of metal ions. *Anal. Biochem.*, 1984, 142, (1), 68).

Briefly, a defined amount of non-radioactive CuCl$_2$ (~150 fold excess of SWNT concentration) in 40 μl 0.1 M NaOAc buffer (pH=6.5) was added to 0.2 mCi of radioactive $^{64}$CuCl$_2$ in 20 μl 0.1 M NaOAc buffer. 20 μl of SWNT solution in 100 μl 0.1 M NaOAc buffer was added to the above carrier-added $^{64}$CuCl$_2$ solution. The reaction mixtures were incubated with constant shaking at 40° C. for 1 h. $^{64}$Cu-labeled SWNTs were purified using 100 kDa filters and the radio-labeling yield was calculated by measuring the radio activity retained in the SWNTs solution. The number of DOTA per SWNT (average length ~150 nm) was determined as moles (Cu$^{2+}$)×yield/moles (SWNT). The DOTA number assay was used for estimation of the number of amine terminated PEG chains on SWNTs. Standard deviations (std.) were obtained from 4 parallel samples, and the results are shown in the Table 1 below.

TABLE 1

| | Average number of DOTA per 200 nm of SWNT | Std. |
|---|---|---|
| PL-SWNT | 61.9 | 3.5 |
| OXNT | 44.8 | 1.2 |

The measured number of DOTA provided an estimate for the number of amine terminated PEG chains on functionalized SWNTs. For both non-covalent and covalent functionalization, the density of PEGylation on the tubes was low, but the PEG chain length (100-200 PEO units) was long, which was found sufficient to impart high aqueous solubility and stability of SWNTs in buffer solutions and in serum with aggregation of nanotubes.

Example 6

Stability of PEGylated-SWNT-DOX (Hipco Tubes) Complexes in Serum

PL-SWNT-DOX and OXNT-DOX (with DOX loaded onto the functionalized nanotubes by simple incubation at pH=9 as described in the heading "Binding of drugs to solubilized nanoparticles" under "General Methods and Materials") were incubated in 100% fetal bovine serum (FBS) at 37° C. Released doxorubicin was removed by filtration at different time points and the remaining PEGylated nanotubes were measured by UV-VIS-NIR. SWNTs without any DOX loading were incubated with FBS in the same way and also characterized by UV-VIS-NIR after filtration. We observed that only 8~12% of DOX was detached from SWNTs after incubating the complexes in serum for 2 days (FIG. 8A-C) for both PL-SWNT-DOX and OXNT-DOX. This result showed that our SWNT-DOX complexes exhibited good stability in physiological solution containing various salts and proteins. Further, no aggregation of nanotubes in serum was seen through the entire experimental duration.

Example 7

Control Experiments for Doxorubicin Loading on PEGylated SWNTs

Several control samples were used to confirm the doxorubicin loading. 1 mM free doxorubicin and doxorubicin mixed with 1 mg/ml PL-PEG (no SWNTs) were incubated at pH9 overnight. After centrifugation to remove any precipitates, the solution was filtered and washed with water and phosphate buffered saline until the filtrate became colorless. The same procedure was done for doxorubicin after mixing with PL-SWNTs and OXNTs. It was visually observed by color change that free doxorubicin and doxorubicin mixed with PL-PEG can be washed away easily after filtration. The latter had slight color likely due to a small amount of DOX trapped in micelles formed by PL-PEG since the PL-PEG concentration used was very high (1 mg/ml). Most of the excess free PL-PEG molecules in the PL-SWNT solution were removed thoroughly by filtration. We also observed (data not shown) the retention of DOX (a red color) in SWNT solutions after filtration owing to the formation of SWNT-DOX complexes (for both PL-SWNTs and OXNTs). The color of the PEGylated SWNTs appeared black, while the DOX complexed PEG-SWNTs appeared dark red.

Atomic force microscope images were taken for PL-SWNTs before and after doxorubicin loading. A drop of PL-SWNT or PL-SWNT-DOX solution was deposited on a clean Si substrate for ~10 minutes and blow-dried after AFM imaging. The average diameter of SWNTs was found to be increased from ~1.3 nm to ~3 nm due to the loading of doxorubicin on nanotubes.

Example 8

Estimation of Surface Area Coverage of Molecules on SWNTs

The percentages of surface area coverage by molecules on SWNTs were estimated by assuming the diameter of nanotubes to be 1.5 nm, which would make the total surface area of the 10 nm nanotubes 47 nm$^2$. We estimated based on our measurements that ~3 PL-PEG and ~50 DOX were attached on a 10 nm length of nanotube. The size of the carbon hydrogen chains in PL-PEG and the aromatic structure of DOX were estimated by Chem3D software. The Dox was estimated to be approximately 1.06 nm long (transverse to the ring) and 0.66 nm wide, with an area of 0.7 nm$^2$. The size of one carbon chain (about 9 Carbons) in the PL-PEG was estimated to be 2.13 nm long and 0.34 nm wide, giving an area of 0.72 nm$^2$.

The percentage of surface area covered by PL-PEG (two carbon hydrogen chains) was then 0.72×2×3/47≈10%. For DOX, the coverage was ~0.70×50/47≈75%.

Example 9

Complete Releasing of DOX from SWNTs in Acidic Solutions

PL-SWNT-DOX (with DOX loaded at pH 9 as described in the heading "Binding of drugs to solubilized nanoparticles" under "General Methods and Materials) was dialyzed against acetate buffer in a very acidic pH=4 buffer for 3 days (FIG. 9). After this treatment, UV-VIS revealed that the doxorubicin peak at 490 nm almost disappeared from the nanotube solution, indicating that most of the doxorubicin was released from the SWNTs and removed by dialysis. Importantly, the remaining SWNT solution was stable without any aggregation of nanotubes observed. This indicated that the PL-PEG functionalization on SWNTs was intact and without detachment during doxorubicin loading, otherwise nanotubes would have precipitated out from the aqueous solution.

Example 10

Supramolecular Binding of Daunorubicin and FITC-NH2 on Functionalized SWNTs Besides doxorubicin, we also investigated binding of several other aromatic molecules onto water soluble PEGylated SWNTs. Daunorubicin is another chemotherapy drug with a similar structure to doxorubicin. We found that this molecule could also be attached to PL-SWNTs, with similar pH dependent behavior as DOX but a lower maximum loading efficiency of ~¼ of DOX (FIG. 10A). The lower efficiency was attributed to the higher hydrophilicity of daunorubicin than DOX.

Figure 10B:
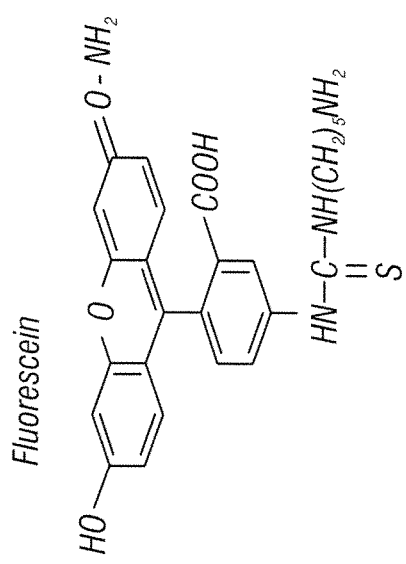
Figure 10B:
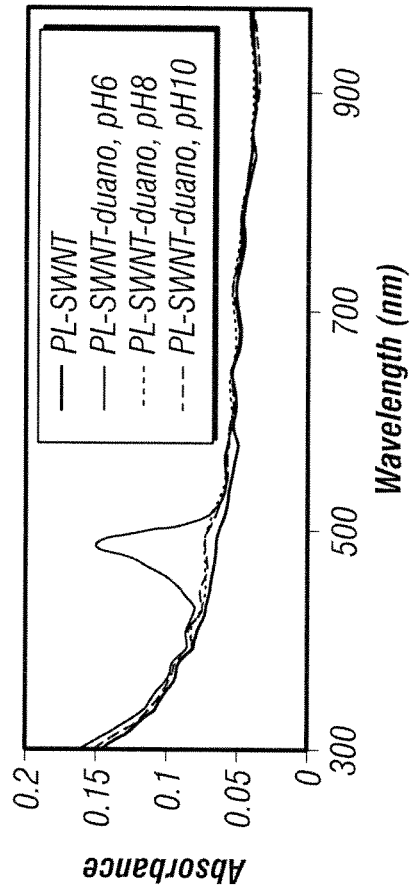

We found that a fluorescein derivative FITC-NH$_2$ was loaded onto PEG-SWNTs with high efficiency at the isoelectric pH (pI~6) of fluorescein (FIG. 10B). About 40 FITC molecules were loaded per 10 nm length of SWNT (vs. ~50 DOX per 10 nm of SWNT loaded at pH 9). FITC was released from PL-SWNTs at high pHs (FIG. 10B) due to increased hydrophilicity resulting from deprotonation of the carboxylic acid group on the molecule.

Figure 11A:
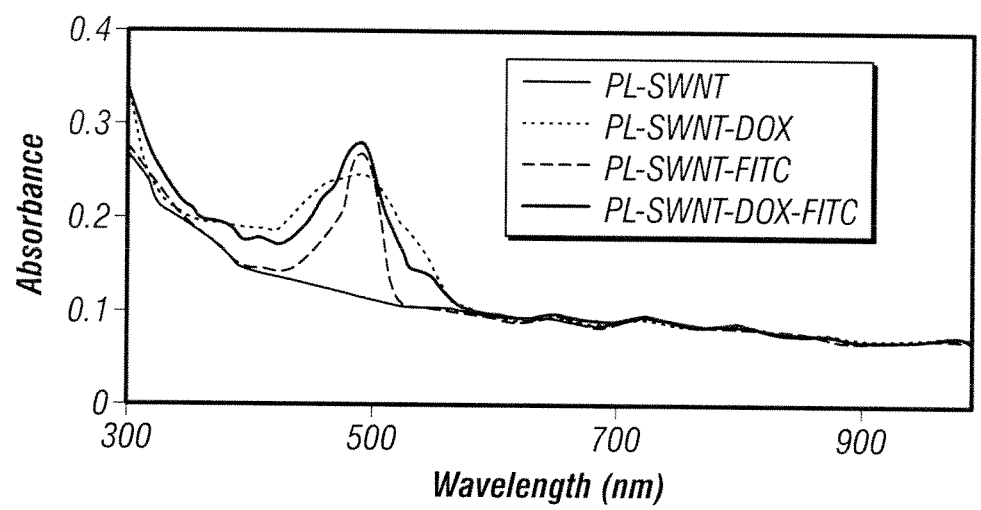
FIGS. 11A and 11B are graphs showing percentage of DOX retained. 11A is a graph showing UV-Vis-NIR spectra of a PL-SWNT solution, and a PL-SWNT solution loaded with doxorubicin, fluorescein, and doxorubicin and fluorescein combined, respectively. For multiple-molecule loading, fluorescein was loaded at pH=6 after loading of doxorubicin at pH=9. The ratio of doxorubicin to fluorescein bound to SWNTs was estimated to be ~2:1.
Figure 11B:
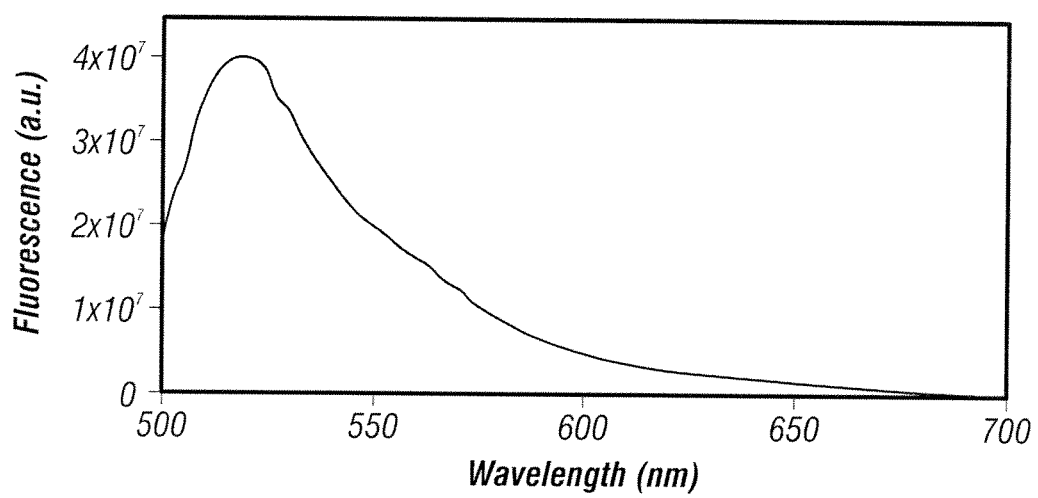

Importantly, our supramolecular approach allows for loading of multiple aromatic molecules onto SWNTs, as illustrated by binding DOX and fluorescein at different pHs (FIGS. 11A and B). Thus, one can readily obtain SWNT assemblies with various functional molecules non-covalently populating SWNT sidewalls, with a small percentage of strongly bound PEG extending out for aqueous solubility of the assembly.

Example 11

Measurement of DOX Binding Energy

The diameter distributions of two types of SWNTs were obtained by AFM topographic height measurements of ~100 PL-PEG functionalized nanotubes in each material, after depositing them on Si substrates from solutions (FIG. 12). Both Laser PL-SWNT-DOX and Hipco PL-SWNT-DOX (DOX loaded at pH=9) were incubated in PBS and kept at various temperatures (20° C., 40° C., 60° C., 80° C.). Released doxorubicin was removed at different time points and the retained doxorubicin was measured by UV-VIS-NIR to get temperature dependent releasing curves (FIGS. 13A and B). Note that the absorbance of free doxorubicin exhibited decreases when heated at high temperatures (dropped by ~30% at 60° C. and ~50% at 80° C. after 24 hours). This was corrected in obtaining our release curves. The half-lives ($t_{1/2}$) of doxorubicin on PEGylated SWNTs at various temperatures were obtained by fitting the releasing curves to exponential decays. We then used Arrhenius fits of $11 t_{1/2}(T) = A \times \exp(-E_B/k_B T)$ where A is a constant for extracting binding energy $E_B$ of DOX on the PEGylated Hipco and laser-ablation nanotubes.

Example 12

SWNTs Loaded with both Paclitaxel (PTX) and Doxorubicin (DOX)

Figure 14:
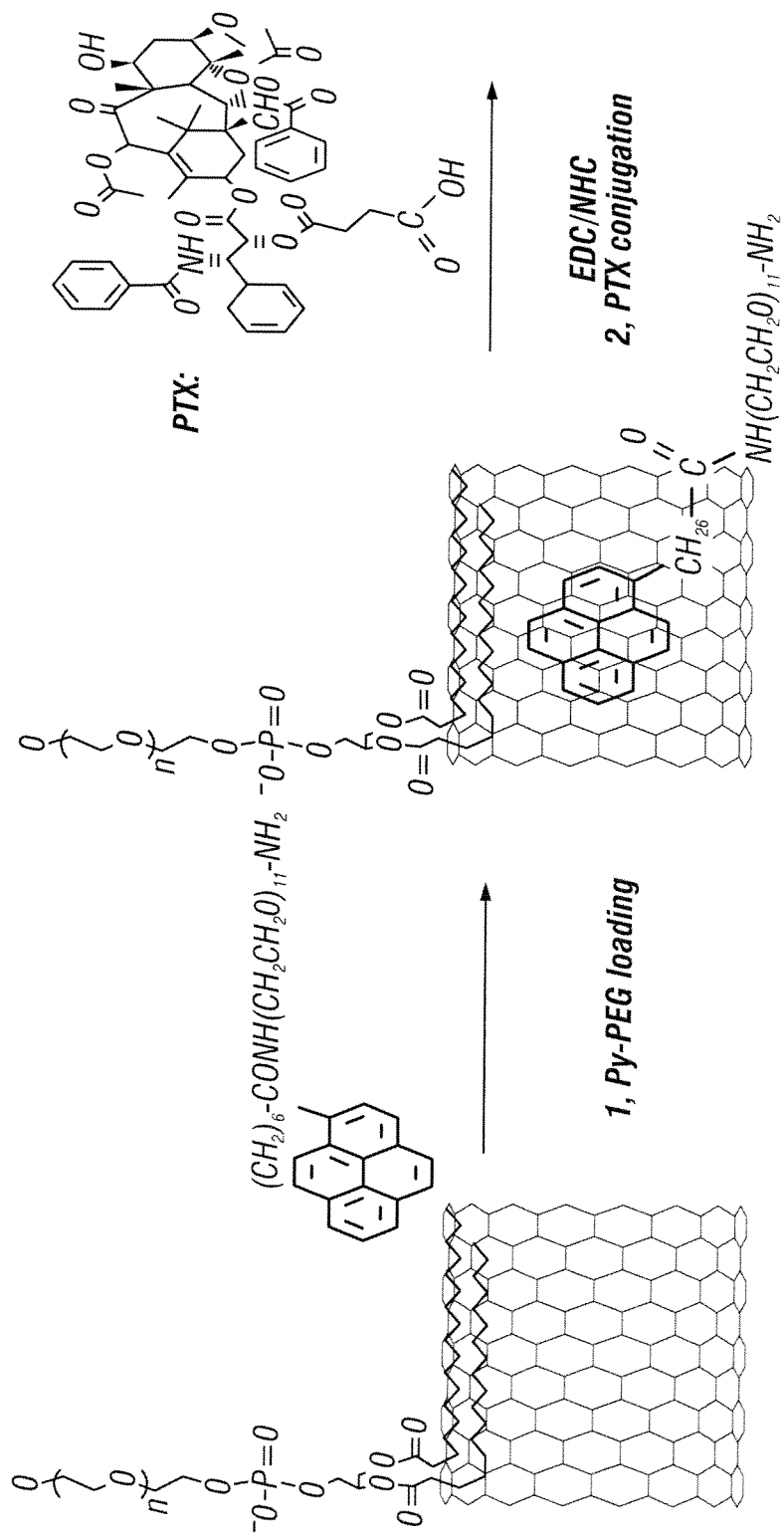
FIG. 14 is a reaction scheme showing SWNTs loaded with paclitaxel (PTX) and doxorubicin (DOX). The PTX is not bound by π stacking, but is rather coupled to a Py-PEG which is adsorbed in step 1 to a PL-PEG functionalized SWNT. The Py-PEG contains a pyrene ring compound linked to an amine-terminated PEG, wherein the amine is used to prepare a cleavable linkage to the active agent (in this case PTX).
Figure 14:
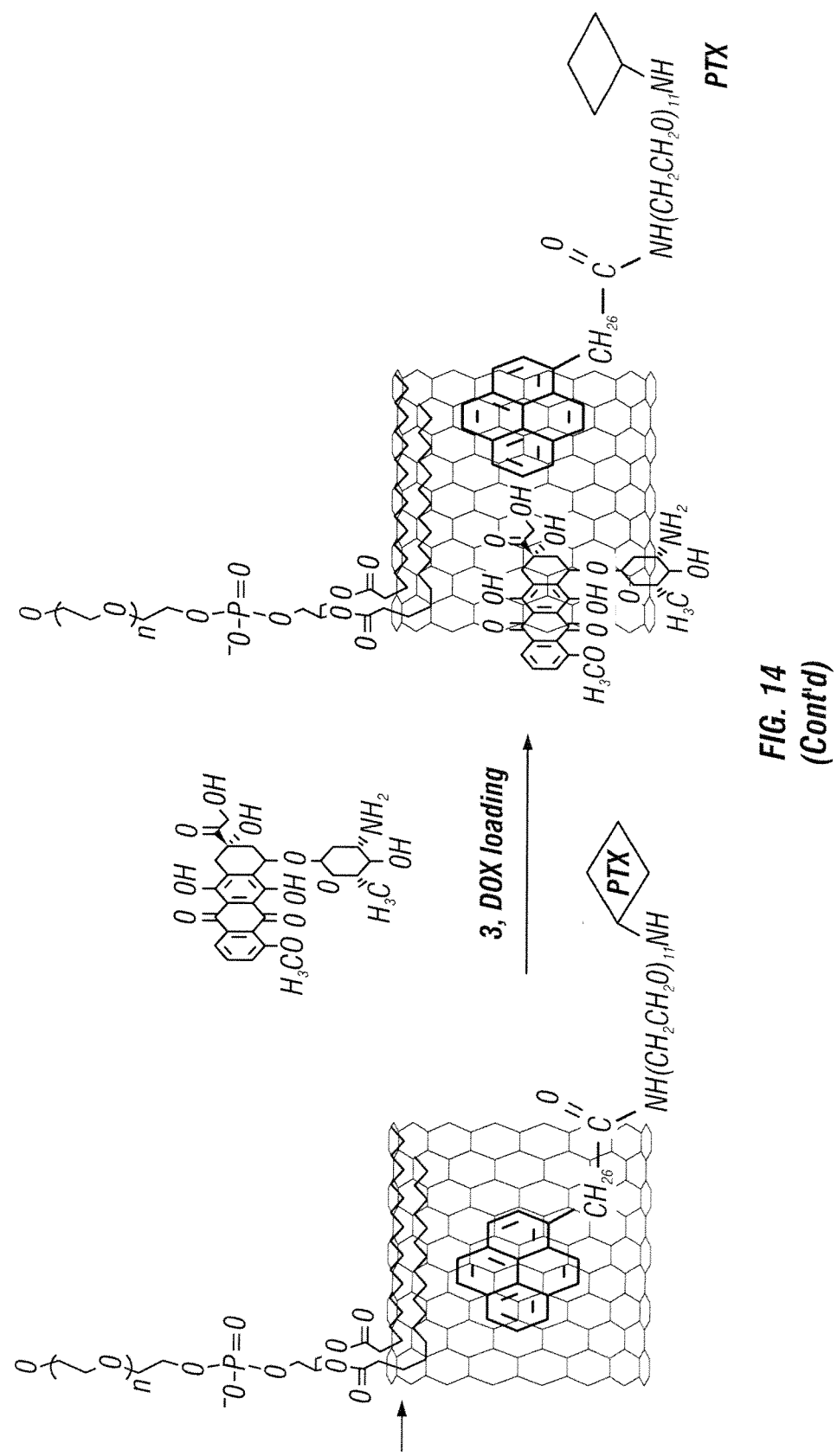

As shown in FIG. 14, SWNTs were loaded with both paclitaxel (PTX) and doxorubicin (DOX). The DOX was adhered to the SWNT surface directly. The PTX was linked to a hydrophilic polymer containing 11 ethylene repeats and having a free amine terminus for conjugation to PTX, and a pyrene terminus for supramolecular bonding to the SWNT. In addition, a solubilizing PEG was non-covalently attached, as described above. This was done first. Then, Py-PEG was added. PTX was then reacted with the amine terminus of the Py-PEG by EDC/NHS reaction. A cleavable linkage was provided between the PTX and the PEG. A variety of cleavable linkages may be employed in order to provide intracellular or circulatory release of the active agent from the PEG or other hydrophilic polymer. An example of a disulfide cleavable linkage is given in *J. Am. Chem. Soc.*, 2005, 36, 12492-12493, cited above. The present ester linkage is illustrated in the box in FIG. 16. Examples of other in vivo cleavable linkages are given in U.S. Pat. Nos. 6,984,396, and 6,096,726. As described there, the language "cleavable linkage" is intended to include those covalent chemical bonds, which attach bioeffecting agents to substrates in a manner such that when disassociation occurs, and the bioeffecting materials are released, the bioeffecting activity of the bioeffecting materials is substantially maintained. Covalent bonds, which are disassociated by hydrolysis reactions, are preferred. Thioether bonds, as described in U.S. Pat. No. 4,981,979 may also be used. As another example, cleavable vinyl ether bonds may be used as described in U.S. Pat. No. 6,979,460. A hydrazone linkage is also preferred. Further description of the synthesis and use of such a cleavable linkage is found at U.S. Pat. No. 4,801,688 to Laguzza, et al., issued Jan. 31, 1989, entitled "Hydrazone immunoglobulin conjugates." As described there, the hydrazides used in forming the active agent-hydrophilic polymer conjugates are prepared differently, depending on whether the hydrazide is attached at C-3 or C-4. The C-3 hydrazides are prepared by the procedure of U.S. Pat. No. 4,203,898, col 12, line 65 et seq. and Example 3, col 18. In this procedure, anhydrous hydrazine is reacted with an active agent in ethanol in a sealed tube at about 60° C. The present cleavable linkages are biologically cleaved and should be physiologically nontoxic.

Then DOX was loaded onto the SWNTs carrying the Py-PEG-PTX. Details are as follows:

Making Pyrene-PEG(11)-NH2 for Step 1 Py-PEG Loading

Reagents: 1) 40 mM—NH2-PEG(11)-BOC, i.e., NH2-PEG(11)-BOC aka O-(2-Aminoethyl)-O'-[2-(Boc-amino)ethyl]decaethylene glycol—Sigma-Aldrich #77090>90% purity MW=644.79; 2) 8 mM—1-pyrenebutyric acid MW, Sigma-Aldrich #257354 MW=288.34; 3) 200 mM—EDC, aka 1-Ethyl-3-[3-dimethylaminopropyl]carbodiimide hydrochloride—Pierce #22980 MW=191.7; 4) 50 mM—NHS, N-hydroxysuccinimide—Pierce #24500 MW=115.09, 5) Methanol, 6) Trifluoroacetic acid (TFA) 100%.

Procedure: Dissolve reagents 1-4 in dry methanol (usually 3 mL scale); mix to react overnight (12-16 hours); dry methanol with house air or rotovap; add equal volume of 100% TFA to deprotect BOC group, overnight with mixing (12-16 hrs); dry TFA with house air; add half equivalent volume of methanol (usually 1.5-2 mL) and dry with air, repeat for total of 3×—should give slightly yellow viscous liquid; dissolve product in full equivalent volume of water—should give approx. 8 mM pyrene-PEG(11)-NH2-transparent, slightly yellow solution, stable for weeks at 4° C.

Note: if solution is cloudy, probably due to unreacted pyrenebutyric acid, can centrifuge to remove solids. Typical pyrene-PEG(11)-NH2 yield was 70% by UV/Vis of pyrene peak at 343 nm ($\epsilon \approx 39,000$ $M^{-1}$ $cm^{-1}$)

Functionalizing Carbon nanotubes with Pyrene-PEG(11)-NH2 (step 1, FIG. 14)

Reagents: 1) 200-300 nM SWNTs suspended in water by PL-xPEG-R where x=2,000, 5,000, or 5,400 Da and R=—NH2 or —OCH3; SWNTs are 0.25 mg/mL Hipco NT, ~260 uM PL-PEG—approx 1-1.5 mg/mL, sonicate in water 1 hr, 15,000 RPM centrifuge for 6 hours, filter through 100 kDa centrifuge filters; concentration determination by UV/Vis at 808 nm ($\epsilon \approx 0.0079$ $nM^{-1}$ $cm^{-1}$); 2) 1 mM pyrene-PEG-NH2 (aq)

Procedure: (1) Mix 200-300 nM SWNTs in water and 1 mM pyrene-PEG(11)-NH2 (typical scale 500-1000 uL). Allow co-functionalization to proceed at 4° C. overnight (12-16 hrs); (2) Filter to remove excess pyrene-PEG(11)-NH2 through 100 kDa ultracentrifuge filters at 10,000 g. To double check thorough excess removal, one may use a 10 kDa filter and take UV/Vis spectrum of filtrate at 343 nm. Quantify pyrene-PEG(11)-NH2 loading by UV/Vis Pyrene-PEG(11)-NH2 $\epsilon \approx 39,000$ $M^{-1}$ $cm^{-1}$ at 343 nm and Hipco SWNT $\epsilon \approx 0.0079$ $nM^{-1}$ $cm^{-1}$ at 808 nm [pyrene-PEG(11)-NH2]/[SWNT]=# pyrene-PEG(11)-NH2 per NT=700~1000

Pacltaxel Conjugation to Loaded Pyrene-PEG(11)-NH2 (step 2, FIG. 14)

Modification of Paclitaxel to Form a Cleavable Ester Bond:
50 mg paclitaxel and 90 mg succinic anhydride were mixed in pyridine and reacted for 4 hours. After evaporating the pyridine, water was added and stirred for 20 minutes. Solid was collected and dissolved in a small amount of acetone. Water was added again to precipitate the paclitaxel. Paclitaxel-COOH was freeze-dried and stored at −20° C.

Paclitaxel-COOH Conjugation on SWNTs
SWNT solution with PL-PEG-NH2 functionalization and pyrene-PEG-NH2 loading was reacted with Paclitaxel-COOH (in DMSO) in the presence of EDC and sulfo-NHS. The final concentrations were: 0.5 mM Paclitaxel-COOH, 5 mM EDC, 5 mM sulfo-NHS, 10% DMSO. After overnight reaction at 4° C., excess reagents were removed by filtration through 5 kD filters and washed thoroughly.

Note that the Paclitaxel conjugation method is the same for NT/PL-PEG+Py-PEG and NT/PL-branched PEG.

DOX Loading on SWNT-PTX (Step 3, FIG. 14)

SWNT-PTX was mixed with 1 mM DOX at pH~8 overnight at 4° C. Excess DOX was removed by filtration through 5 kD filters and washed thoroughly.

The SWNT-PTX complex was studied (without DOX) by UV-VIS of nanotubes (NT); NT-PY and NT-Py-PTX. From the UV-VIS-NIR spectra, we can measure the number of pyrene and PTX per nanotube. SWNT concentration was calculated by absorbance at 808 nm, pyrene: 343 nm, PTX: 220 nm. We estimated the number of Py per 200 nm NT: 700~1100 for Hipco SWNTs (depending on the mixing ratio between Py and SWNT). This characterization showed that ~85% of Py remains on NTs after PTX conjugation. We found that 800~1200 molecules of PTX can be conjugated to SWNTs with the Py-PEG conjugation. Without Py loading only ~100 PTX per nanotube could be attached. These numbers were confirmed by conjugating nanotubes with $H^3$ radiolabeled PTX. Additional UV-VIS spectroscopy resulted in the following calculated results:

TABLE 2

|  | Py # per SWNT | PTX # per SWNT | DOX # per SWNT |
|---|---|---|---|
| SWNT-Py | 600~800 | 0 | 0 |
| SWNT-Py-PTX | 500~700 | 600~800 | 0 |
| SWNT-DOX | 0 | 0 | 800~1000 |
| SWNT-Py-PTX-DOX | 500~700 | 600~800 | 1200~1400 |

The conjugates were also studied by fluorescence spectroscopy. The conjugates were excited at 488 nm (DOX fluorescence) and 343 nm (Pyrene fluorescence). Fluorescence spectra were taken for different SWNT-drug conjugates. DOX fluorescence was quenched after loading on NTs.

Pyrene fluorescence was also quenched after loading on NTs but a "tail" showed up.

The "tail" disappeared after further DOX loading.

Example 13

Cell Toxicity of Conjugates from Example 12

4T1 cells were plated in 98-well plates one day before drug treatment. After 48 hours post drug treatment, a standard MTS assay (Celltiter kit, Promega) was performed to evaluate the percentage of viable cells (compared with untreated control).

Referring now to FIG. 15, viable cells were measured after addition of SWNT, free DOX, NT-DOX, free PTX, NT-DOX, free PTX+DOX and NT-PTX-DOX. 4T1 cells (a murine breast cancer cell line) were incubated with various free drugs and SWNT-drugs for 48 hours followed by MTS assay. Concentration dependent toxicity data showed that SWNTs loaded with both DOX and PTX had the highest toxicity Example 14

SWNT-PTX (Paclitaxel) Conjugates

Figure 17:
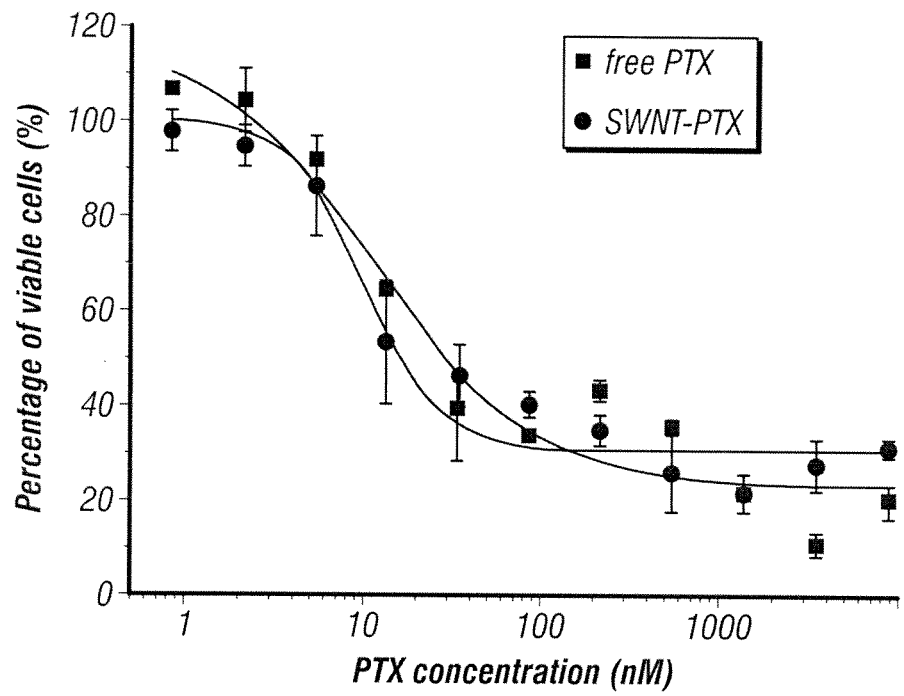
FIG. 17 is a graph showing an in vitro toxicity test with a 4T1 cell line showing that the illustrated structure had a similar in vitro toxic effect as free PTX, where the degree of loading of multiply bound PTX resulted in ~300 PTX per 200 nm of SWNT.

Referring now to FIG. 16, there is illustrated a complex comprising an SWNT having the lipid portion of a phospholid absorbed on it, where the phospholipid is coupled to a branched PEG amine-linked to paclitaxel. The branched hydrophilic polymer (PEG) had a lipid at one end, adsorbed on to the nanoparticles, and had at the other end three arms, with each arm bearing a PTX drug, linked to the PEG with a cleavable linkage (ester). In the figure, m is approximately 57, showing the units distal from the SWNT of the branch point, and n, representing units proximal to the SWNT, is ~188 units. It was estimated that this structure contained ~300 PTX per 200 nm of SWNT. The paclitaxel (PTX) was bound to the branched PEG by an ester linkage (shown in the box), which was stable in solution, but cleaved in vivo. FIG. 17 shows cell culture data from the above conjugate, where viability of cells is shown to be comparable to use of free PTX at various concentrations of PTX.

PL-branched PEG was prepared as follows: First, PL-PEG5000-COOH was synthesized. DSPE-PEG5000-

Amine (PL-PEG5000-NH2, NOF corporation) was mixed with 5 e.q. succinic anhydride in a mixture of methene chloride and pyridine (1:1) and reacted overnight at room temperature. The solvent was evaporated and the product was dissolved in water. After dialysis against pure water for 2 days with 1000 Da MWCO membrane, the product was lyophilized into powder and stored at −20° C. Next, PL-branched PEG was synthesized. Previously synthesized PL-PEG5000-COOH was mixed with 1.5 e.q. N,N'-dicyclohexylcarbodiimide (DCC, Aldrich) and 2 e.q. N-hydroxybenzotriazole (HOBt) for 1 hour in methene chloride. 4 e.q. 4 armed-PEG-Amine (10 kDa, Aldrich) was added into the above reaction solution. After 48 hours reaction, the solvent was evaporated and dissolved in water. Solid precipitate was removed by filtration, and yielded clear PL-branched PEG-NH2 water solution, as diagrammed at FIG. 16.

Then, Hipco SWNTs were sonicated in a 0.2 mM solution of DSPE-PEG5000-4-Arm-(PEG-Amine) for 30 min with a cup-horn sonicator followed by centrifugation at 24,000 g for 6 h, yielding a suspension of SWNTs with non-covalent phospholipid-branched PEG coating in the supernatant Paclitaxel Conjugation on SWNT-PL-Branched PEG The same sonication conditions were used to make SWNT-PL-branched PEG solution. After removal of excess phospholipids, succinic anhydride modified paclitaxel was conjugated to nanotubes using the same protocol described in Example 12.

Example 15

In Vitro PTX Treatment

Figure 18:
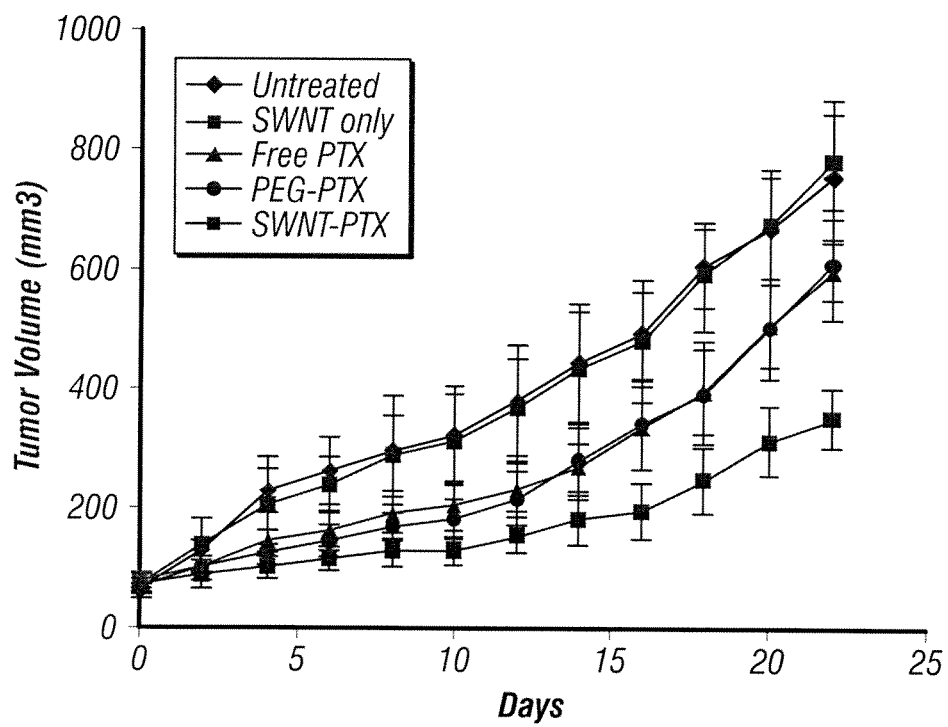
FIG. 18 is a graph showing reduction in tumor volume after treatment with different formulations including SWNT-PTX.
Figure 19:
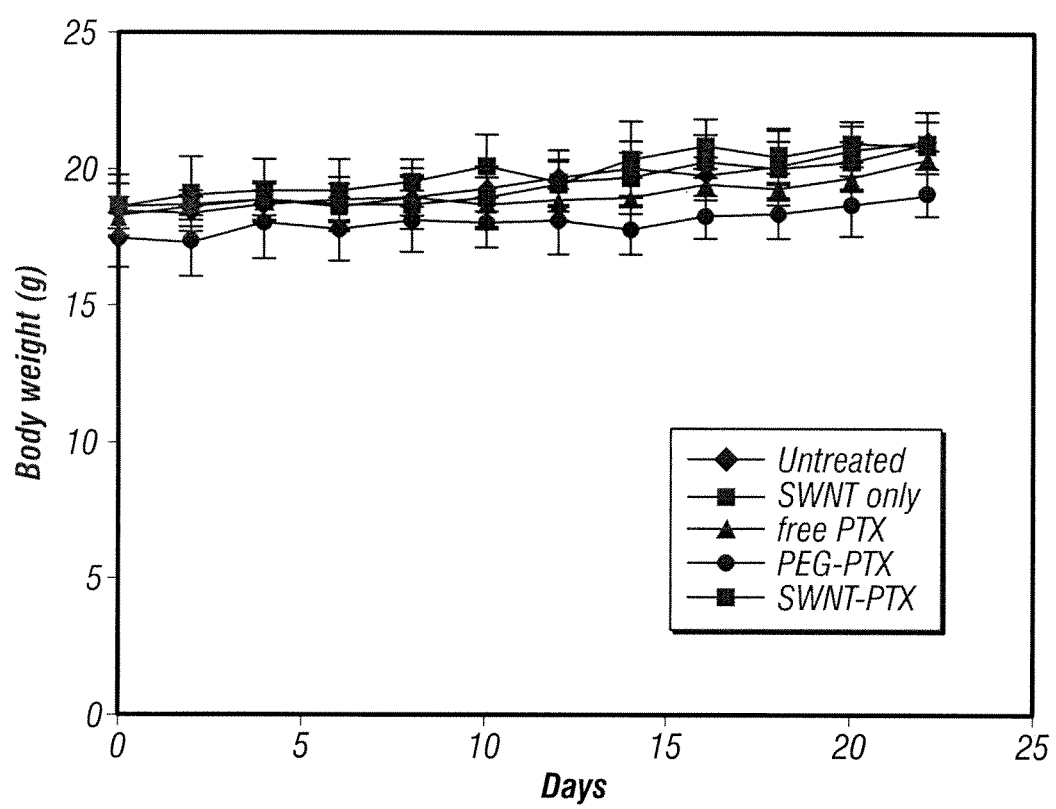
FIG. 19 is a graph showing body weight for the formulations of FIG. 18 over the same period during the treatment.

FIG. 18 shows changes in tumor volume and body weight in an in vivo treatment experiment comparing Free PTX, PEG-PTX, SWNT-PTX, SWNT only and control mice. Female Balb/c mice with implanted 4T1 tumors were treated with the compositions shown in the graphs at the same PTX dose (5 mg/kg, every 6 days). Slower tumor growth rate was observed for mice treated with SWNT-PTX compared with a clinical PTX formulation (Taxol® paclitaxel) or PEGylated PTX. No obvious side effects were seen. No mouse in the treatment group died, and no average drop in body weight was seen (FIG. 19). The tumor growth curves were obtained with 5 mice in each group to get the average tumor volumes and standard deviations. Interestingly, obvious lung metastasis was observed for mice treated with free PTX or PEG-PTX but not for those treated with SWNT-PTX.

Synthesis of PEGylated paclitaxel (labeled "4PEG-PTX"): 0.2 mM of 4 armed PEG-Amine (Aldrich) was reacted with 0.5 mM of succinic anhydride modified paclitaxel at pH 7.5 overnight in the presence of 5 mM EDC and 5 mM Sulfo-NHS. The reaction condition is very similar to the paclitaxel conjugation on SWNTs.

Example 16

In Vivo Fate of Nanoparticles Coated with Branched vs. Linear PEG

Relying on the intrinsic resonance Raman spectroscopic signatures of single walled carbon nanotubes (SWNTs), the blood circulation of SWNTs was measured and SWNTs in various organs and tissues of mice ex vivo were detected over a period of several months. By using SWNTs functionalized by linear PEG with different chain lengths and branched PEG, the results here show that the degree of polyethylene glycol (PEG) functionalization on SWNTs is not only important to their blood circulation time and uptake in the reticuloendothelial system (RES), but also to their clearance behavior. Functionalization of SWNTs by branched PEG exhibits prolonged blood circulation half-life of ~5 h, which is superior to that of linear PEG. SWNTs with higher degree of PEGylation exhibited faster clearance from the RES of mice, likely via the biliary pathway, with nearly complete clearance over a period of ~2 months for SWNTs functionalized with branched PEG. No toxic side effect of SWNTs to the animals was observed in necropsy, histology and blood chemistry measurements.

Figure 20:
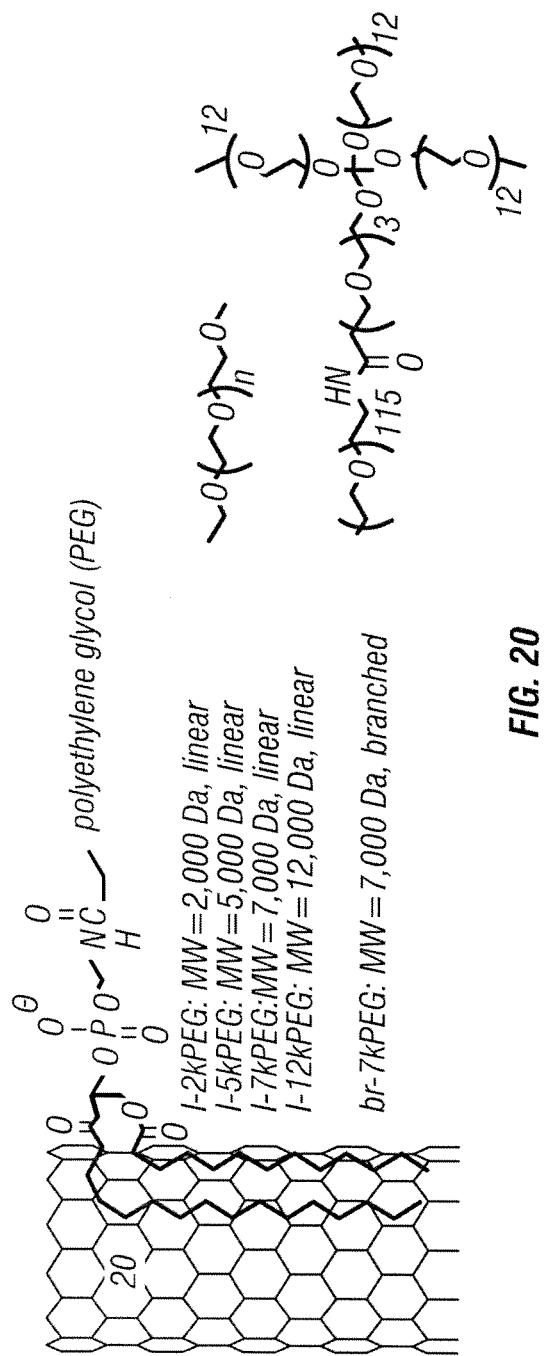
FIG. 20 is a schematic drawing of a SWNT functionalized with different phospholipid-PEGs with linear or branched PEG structure.

Several PL-PEGs with linear PEG structure and one PL-PEG with branched PEG structure were used in this study (as shown in FIG. 20) including commercially available DSPE-PEG(2000) Amine (denoted as 'PL-l-2kPEG' where l stands for linear) and DSPE-PEG(5000) Amine (PL-l-5kPEG) from Avanti Polar Lipids, Inc. PL-l-7kPEG was synthesized by mixing 1 eq. of DSPE-PEG5000-Amine with 2 eq. of NHS-mPEG2000 in methylene chloride overnight followed by addition of N,N'-dicyclohexylcarbodiimide (DCC, 2 eq.). The solvent was evaporated after another 24 hours reaction. Water was added and the insoluble solid (unreacted DCC) was removed by vacuum filtration. The final product was a clear water solution and was stored at −20° C. for future usage. PL-l-12kPEG and PL-br-7kPEG (where br stands for 'branched') were synthesized by similar methods except for the starting materials. 1 eq. of DSPE-PEG2000-Amine and 2 eq. of NHS-mPEG10000 (Nektar Therapeutics) were used to synthesize PL-l-12kPEG while 1 eq. of DSPE-PEG-5000-Amine and 1.5 eq. of (Methyl-PEO$_{12}$)$_3$—PEO$_4$—NHS Ester (Pierce) were used to make PL-br-7kPEG.

Raw Hipco SWNTs (0.2 mg/ml) were sonicated in a 0.2 mM solution of PL-PEG for 1 h followed by centrifugation at 24,000 g for 6 h, yielding a suspension of SWNTs with non-covalent PL-PEG coating in the supernatant. Excess surfactant and un-reacted PEG molecules in the case of synthesized PL-PEG were removed by filtration through a 100 kDa MWCO filter (Millipore), typically 1 day prior to in vivo experiments. Right before injection, the solution was centrifuged again at 24,000 g for 6 h to remove any potential aggregates. UV-VIS-NIR absorption spectrum of the SWNT solution was acquired by a Cary 6000i UV-visible-NIR spectrometer. Atomic force microscopy (AFM) images were taken by depositing SWNTs from solution onto SiO$_2$ substrates. The average length of SWNTs was measured to be ~100 nm averaged over 100 tubes imaged by AFM. The concentration of a SWNT solution was determined by Raman spectroscopy (see below) and by optical absorbance at 808 nm with a weight-concentration based extinction coefficient of 46 L·g$^{-1}$·cm$^{-1}$ or a molar extinction coefficient of 3.9×10$^6$ M$^{-1}$·cm$^{-1}$ for typical ~100 nm long tubes (10).

SWNT solutions of various concentrations in capillary glass tubes were measured using a Renishaw micro-Raman instrument (laser excitation wavelength=785 nm). A glass capillary tube filled with a SWNT solution was placed under the objective (20×) of the Raman microscope. After focusing at the center of the capillary, we recorded the Raman spectrum of the solution (100 mW power with laser spot size of ~25 μm$^2$, 10 second collection time). At least 4 spectra were taken for each sample for averaging. For a given concentration of SWNT solution, the Raman intensity was obtained by integrating the SWNT G-band peak area from 1570 cm$^{-1}$ to 1620 cm$^{-1}$ and averaged over several spectra. 200 μl of ~0.1 mg/ml SWNT saline solution was intravenously (i.v.) injected into the tail vein of 6 week old balb/c mice. Prior to injection of the SWNT solution, a Raman spectrum was recorded and used to calculate the SWNT concentration based on the calibration curve described above. At various time points post injection (p.i.), ~5 µl of blood was collected from the tail vein (using a different vein from the injected one) and dissolved in 5 µl of lysis buffer (1% SDS, 1% Triton X-100, 40 mM Tris Acetate, 10 mM EDTA, 10 mM DTT) for detecting SWNTs in the blood by Raman measurement. The Raman G band peak areas were measured to calculate the SWNT concentrations in the blood. The percentage of the injected dose per gram (% ID/g) of blood was calculated by the following equation:

$$\% \ ID/g = \frac{[SWNT]_{blood\ lysate} \times V_{blood\ lysate}}{[SWNT]_{injected} \times V_{injected\ SWNT} \times \text{blood weight}} \times 100\%$$

For biodistribution in organs, mice were sacrificed at 1 day, 30 days, 60 days and 90 days p.i., and their organs were collected, weighed and solubilized in the lysis buffer using a homogenizer (strong stirring and sonication, 1 min for each sample). After heating at 70° C. for ~2 h, clear homogenate tissue solutions were obtained for Raman measurement. The biodistribution of SWNTs in various organs of mice was then calculated and plotted in unit of % ID/g based on the following equation, $$\% \ ID/g = \frac{[SWNT]_{tissue\ lysate} \times V_{tissue\ lysate}}{[SWNT]_{injected} \times V_{injected\ SWNT} \times \text{tissue weight}} \times 100\%$$

We used 3-4 mice per group at each p.i. time point to obtain the average value and standard deviation for both blood circulation and biodistribution measurements.

We also used a micro-raman technique (Liu, Z., Winters, M., Holodniy, M. & Dai, H. J. (2007) Angewandte Chemie-International Edition 46, 2023-2027) to carry out raman imaging of SWNTs in liver slices. To obtain the Raman mapping image of liver slices (for mice sacrificed at 90 days p.i.), 5 µm thick paraffin embedded liver slices were mounted on $SiO_2$ substrate and mapped under a Renishaw micro-Raman microscope with a line-scan model (100 mW laser power, 40 µm×2 µm laser spot size, 20 pixels each line, 2 second collection time, 20× objective). The SWNT G-band Raman intensity was plotted vs x, y positions across the liver slice to obtain a Raman image.

Figure 21A:
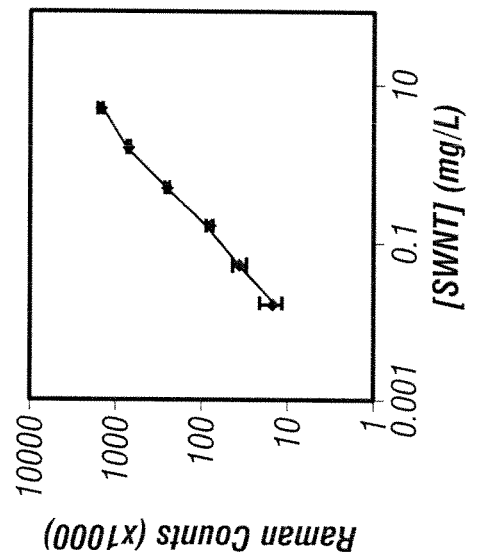
FIG. 21A is a Raman spectrum of SWNTs of FIG. 20. The G band peak at 1590 cm-1 was used for SWNT detection in this work; 21B is a Raman intensity vs SWNT concentration calibration curve. Linear dependence was observed from 0.02 mg/L to 4 mg/L.
Figure 21B:
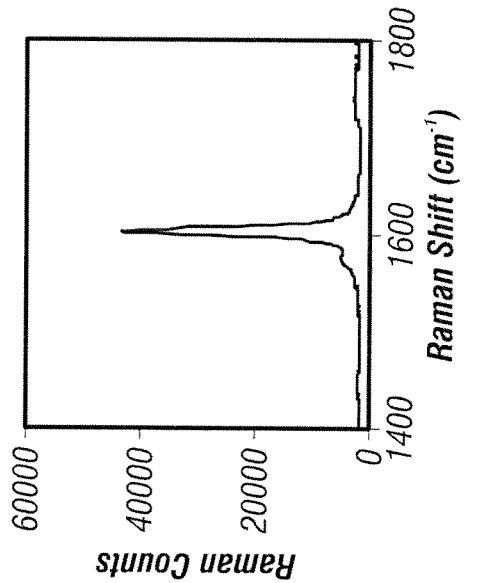

The Hipco SWNTs non-covalently functionalized and solubilized by PEGylated phospholipids were stable without aggregation in various biological solutions including serum. Our previous study also showed that the phospholipid-PEG coating was stable in vivo without rapid detachment (Liu, Z., Cai, W. B., He, L. N., Nakayama, N., Chen, K., Sun, X. M., Chen, X. Y. & Dai, H. J. (2007) Nature Nanotechnology, 2, 47-52). Centrifugation was used to remove big bundles and impurities leaving short individual and small bundles of tubes in the solution. AFM images revealed similar length distributions of different functionalized SWNTs (SWNT-l-2kPEG: 104±49 nm, SWNT-l-5kPEG: 101±51 nm, SWNT-br-7kPEG: 95±46 nm. Strong resonance Raman scattering is an intrinsic optical property of SWNTs with sharp peaks and low background in the spectra. In this work, the tangential graphite-like phonon mode (G band), the strongest peak in the SWNT Raman spectrum, was used to detect nanotubes in solution, blood and tissue lysates. No obvious decay in the Raman signal was observed by measuring the Raman spectrum of a SWNT solution for up to 3 months. Raman spectra of SWNT solutions with known concentrations from 0.2 mg/L to 40 mg/L were taken (see FIG. 21A,B), and the G band intensities (integrated peak areas) were plotted against SWNT concentrations (measured by their NIR absorptions) as the calibration curve. The linear dependence allowed for measurement of SWNT concentration in blood or tissue lysates of mice using Raman spectroscopy (see, e.g., FIG. 21B). Solutions of same concentration SWNTs with different PEG coatings (SWNT-l-2kPEG and SWNT-l-5kPEG, SWNT-br-7kPEG) exhibited very similar Raman intensities in various environments including water, saline, lysis buffer, serum and liver lysate. These suggested that the Raman intensity of SWNTs was relatively insensitive to the coatings and solution environments involved in our experiments.

We intravenously injected ~200 µL saline solutions of different PEG functionalized SWNTs at the same nanotube concentration into mice, and drew blood (~50 µL) at different time points post injection (p.i.) for Raman measurement. The measured percentage of injected SWNTs per gram blood (% ID/g in blood) vs. p.i. time gave blood circulation behavior of SWNTs with various PEGylations (FIG. 22D). As shown there, increasing the linear PEG chain length from 2 kDa (SWNT-l-2kPEG) to 5 kDa (SWNT-l-5kPEG) significantly increased the blood circulation half-life of SWNTs from 0.45 h to 2.4 h (FIGS. 22A, B and D). However, further increase of linear PEG length to 7 kDa (FIG. 22C) (SWNT-l-7kPEG) and even 12 kDa (SWNT-l-12kPEG) showed only minor effect to the blood circulation time (FIG. 22D). On the other hand, SWNT-br-7kPEG, i.e., SWNTs functionalized with three branched PEG chains (FIG. 20A) exhibited a remarkable increase in circulation half-life to 5.3 h (FIG. 21C, D) from ~2.5 h for the SWNT-l-5kPEG. Thus branched PEG structures on SWNTs are preferred in affording optimal inertness of SWNTs that resist osponization or non-specific binding of proteins in vivo, avoid rapid RES uptake and thus prolong circulation in blood. Without wishing to be bound by any one theory, we may attribute this to the idea that the branched PEG structure gives better coverage and higher density of hydrophilic PEG groups on SWNTs, making nanotubes more inert and resistant to non-specific binding and uptake.

To investigate the biodistribution of nanotubes in the main organs 1 day p.i. of SWNTs, we sacrificed mice injected with SWNT-l-2kPEG, SWNT-l-5kPEG and SWNT-br-7kPEG respectively. The organs and tissues were homogenized and solubilized in lysis buffers, for measuring SWNT levels in these organs and tissues by Raman spectroscopy. Dominant SWNT uptake in liver and spleen of the RES over other organs and tissues was observed. Clearly reduced levels of liver and spleen uptake were seen for SWNT-l-5kPEG and SWNT-br-7kPEG compared to SWNT-l-2kPEG, suggesting higher degree of surface PEGylation of SWNTs affording lower RES uptake.

Under our current injected dose and detection conditions, no obvious SWNT signals were detected in other main organs except for minor kidney signal. Note that the detection limit of SWNTs was ~0.4 mg/L in blood and ~2 mg/L in other tissues, corresponding to ~0.2% ID/g and ~1% ID/g of the injected dose respectively. Therefore, the lack of appreciable Raman signals in organs other than liver, kidney and spleen (FIG. 23A) does not mean absolutely no SWNT uptake in those organs. It only suggests that the level of uptake is low, <1% ID/g, and the total amount of SWNTs in these organs could still be non-trivial owing to the large weight of the tissues combined.

To glean the long-term fate of SWNTs in vivo, injected mice were sacrificed at 1 month, 2 months and 3 months p.i. for biodistribution measurements with 3-4 animals per group at each time point. We found that the concentration of SWNTs remained very low in most of the organs of mice except for in the liver and spleen. In these two organs, we did observe SWNT levels steadily decreasing over a 3 months period, with the concentration of retained SWNTs following the trend of SWNT-l-2kPEG>SWNT-l-5kPEG>SWNT-br-7kPEG at later time points (FIGS. 23B and C). In the case of SWNT-l-2kPEG, appreciable amount of SWNTs remained in the liver and spleen with a concentration of ~7% ID/g at even 3 months p.i. In contrast, very low levels (~2% ID/g) of SWNT-l-5kPEG were retained in the RES of mice at 3 months p.i. (FIGS. 23B and C). The least retention of nanotubes in the RES was observed for SWNT-br-7kPEG, with <2% ID/g retention at 2 months p.i. These results suggest that in addition to the advantages of longer blood circulation and lower initial RES uptake, higher degree of PEGylation of SWNTs affords more rapid clearance of SWNTs from mice organs, with branched PEG functionalization giving the most desirable in vivo behavior of SWNTs.

Thus Raman spectroscopy can be used to detect carbon nanotubes in animals to glean the blood circulation behavior and biodistribution in main organs especially in the RES. Although the detection limit is not as satisfactory as the radiolabeling methods, the robust Raman scattering property of SWNTs allows us to track them for a long period of time with high fidelity, without the concern of labels falling off or decay over time. It is found that the surface chemistry of nanotubes is critical to their in vivo behavior, a conclusion that will likely to apply to most nanomaterials, if not all. This is expected since pristine carbon nanotubes have very hydrophobic surfaces and are highly non-specific in binding to biological species. Recently, it has been shown that intravenously injected pristine SWNTs are highly rich in the RES and remain in mice indefinitely (Yang, S.-t., Guo, W., Lin, Y., Deng, X.-y., Wang, H.-f., Sun, H.-f., Liu, Y.-f., Wang, X., Wang, W., Chen, M., Huang, Y.-p. & Sun, Y.-P. (2007) *The Journal of Physical Chemistry CASAP*, 10.1021/jp070712c). This may be blocked by proper chemical functionalization such as the PEG coatings described here, which enables biologically inert SWNTs with long blood circulation, low RES uptake and fast clearance from organs and excretion from the body.

Example 17

Figure 24:
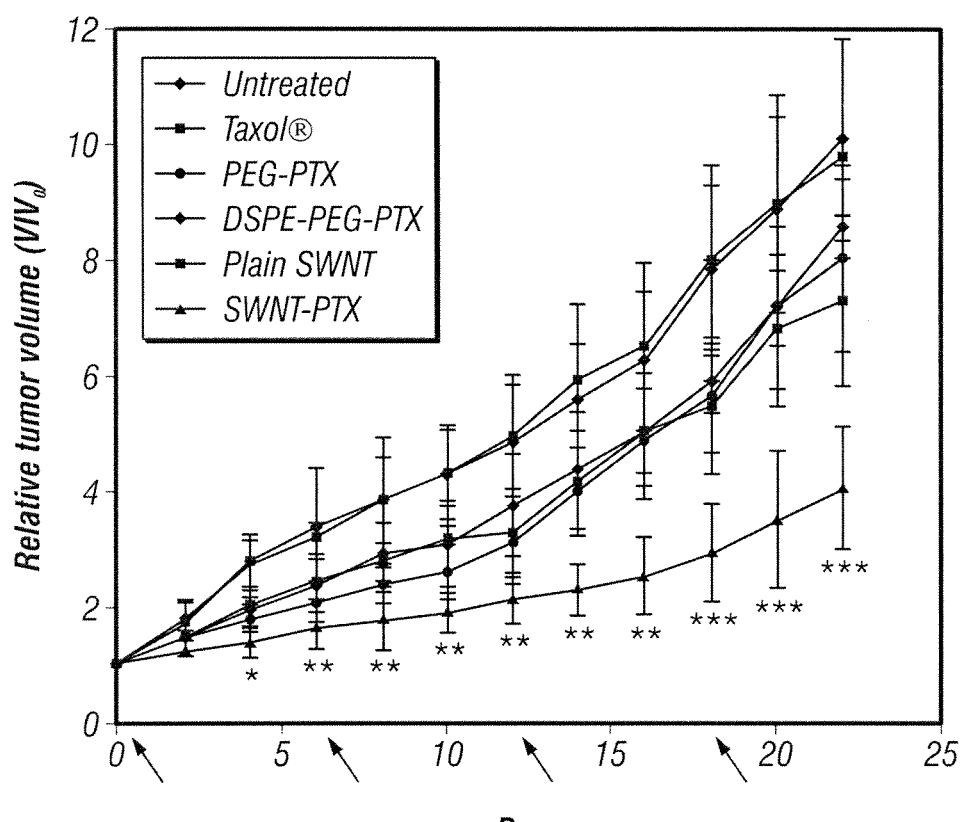
FIG. 24 is a graph showing changes in tumor volume over time in a 4T1 breast cancer mouse model, showing that nanoparticles (SWNTs) bearing branched lipid-PEG, where the lipid is attached to the nanoparticle via supramolecular bonding and further having paclitaxel (PTX) bonded to arms of the PEG, suppresses tumor growth. The same PTX dose (5 mg/kg) was injected on (day 0, 6, 12 and 18, marked by arrows) for Taxol®, PEG-PTX, DSEP-PEG-PTX and SWNT-PTX. P values (Taxol® vs SWNT-PTX): *p<0.05, p<0.01, *p<0.001. Number of mice used in experiments: 8 mice per group for untreated, 5 mice per group for SWNT only, 9 mice per group for Taxol®, 5 mice per group for PEG-PTX, 6 mice per group for DSEP-PEG-PTX, 14 mice per group for SWNT-PTX.

In Vivo Comparison of PTX-Branched PEG Nanoparticles with Taxol® PTX (FIG. 24)

This example extends the exemplification of Examples 14 and 15 to include a comparison between commercially available Taxol® paclitaxel and SWNTs as shown in FIG. 16, having branched PEG bonded by lipid supramolecular interaction to the SWNT, with modified PTX chemically linked to the arms of the PEG by a cleavable ester bond formed with a carboxyl group added to PTX.

This example demonstrates SWNT-based delivery of paclitaxel (PTX) into xenograft tumors in mice with higher tumor suppression efficacy than the clinical drug formulation Taxol® paclitaxel (Bristol-Meyers Squibb, NY, N.Y.). The water insoluble PTX conjugated to PEGylated SWNTs exhibits high water solubility and maintain similar toxicity to cancer cells as Taxol® in vitro. SWNT-PTX affords much longer blood circulation time of PTX than that of Taxol® and PEGylated PTX, leading to high tumor uptake of the drug through EPR effect. The strong therapeutic efficacy of SWNT-PTX is shown by its ability to slow down tumor growth even at a low drug dose (5 mg/kg of PTX). We observe higher tumor uptake of PTX and higher ratios of tumor to normal-organ PTX uptake for SWNT-PTX than Taxol® and PEGylated PTX, highly desired for higher treatment efficacy and lower side effect. PTX carried into RES organs by SWNT-PTX is released from the nanotube carriers likely via in vivo ester cleavage and are cleared out from the body via the biliary pathway. The present formulation preferably does not use Cremophor® (Polyoxyl castor oil), which is used to solubilize paclitaxel. The non-cremophor composition in our SWNT-PTX, rapid clearance of drugs from RES organs, higher ratios of tumor to normal organ drug uptakes, and the fact that tumor suppression efficacy can be reached at low injected drug dose make carbon nanotube drug delivery a very promising nano-platform for future cancer therapeutics.

Functionalization of SWNTs with Phospholipid-Branched PEG

One molar equivalent (eq.) DSPE-PEG5000-Amine (SUNBRIGHT® DSPE-050PA, NOF cooperation) (MW 5800) was reacted with 5 eq. succinic anhydride in dichloromethylene ($CH_2Cl_2$, Aldrich) overnight at room temperature. After evaporating the solvent, the product was dissolved in water. The solution was dialyzed against water with a 3.5 kDa molecular weight cut off (MWCO) membrane for 2 days and then lyophilized into powder. The resulting DSPE-PEG5000-COOH was activated by 1.5 eq. dicyclohexylcarbodiimide (DCC, Aldrich) and 2 eq. hydroxybenzotriazole (HOBt, Aldrich) in $CH_2Cl_2$ at for 1 hour. 4 eq. 4-Arm-(PEG-Amine) (10 kDa, P4AM-10, Sunbio) was added and the reaction solution was stirred for 2 days. After evaporating the solvent, water was added into the container and stirred for 1 hour. Solid precipitate (leftover DCC and HOBt) was removed by filtration via a 0.22 μm filter, yielding clear water solution of DSPE-PEG5000-4-Arm-(PEG-Amine). The product was confirmed by MALDI (matrix-assisted laser desorption/ionization) mass spectrometry in Stanford PAN facility, showing no existence of starting DSPE-PEG5000 material. No further purification was performed since the excess hydrophilic 4-Arm-(PEG-Amine) molecules were confirmed to exhibit no binding affinity to nanotubes.

Raw Hipco SWNTs (0.2 mg/mL) were sonicated in a 0.2 mM solution of DSPE-PEG5000-4-Arm-(PEG-Amine) for 30 min with a cup-horn sonicator followed by centrifugation at 24,000 g for 6 h, yielding a suspension of SWNTs with non-covalent phospholipid-branched PEG coating in the supernatant (14, 18, 23). Excess surfactant and un-reacted PEG molecules were removed by repeated filtration through a 100 kDa MWCO filter (Millipore) and extensive washing with water.

Paclitaxel Conjugation

Paclitaxel (LC Laboratories) was modified by succinic anhydride (Aldrich) according to the literature, adding a carboxyl acid group on the molecule at the C'-2 OH position (see FIG. 16). 300 nM of SWNTs (0.05 mg/ml) with branched PEG-$NH_2$ functionalization was reacted with 0.3 mM of the modified paclitaxel (dissolved in DMSO) in the presence of 5 mM 1-ethyl-3(3-dimethylaminopropyl)carbodiimide hydrochloride (EDC, Aldrich) and 5 mM N-hydroxysulfosuccinimide (Sulfo-NHS, Pierce). The solution was supplemented with 1× phosphate buffered saline (PBS) at pH 7.4. After 6 h reaction, the resulting SWNT-PTX was purified to remove un-conjugated PTX by filtration through 5 kDa MWCO filters and extensive washing.

UV-Vis-NIR absorbance spectra of the SWNT-PTX conjugates were measured by a Cary-6000i spectrophotometer. The concentration of SWNTs were determined by the absorbance at 808 nm with a molar extinction co-efficient of $3.95 \times 10^6$ $M \cdot cm^{-1}$ with an average tube length of ~100 nm (16). Concentration of PTX loaded onto SWNTs was measured by the absorbance peak at 230 nm (characteristic of PTX), after subtracting the absorbance of SWNTs at that wavelength) with a molar extinction coefficient of $31.7 \times 10^5$ M·cm$^{-1}$. Note that thorough removal of free un-bound PTX was carried out by filtration prior to the measurement to accurately assess the amount of PTX loaded onto SWNTs. To confirm the PTX loading measured by UV-VIS, $^3$H-PTX (see the following paragraph) was conjugated to SWNTs. The PTX loading number on nanotubes measured by radioactivity was consistent to that measured by UV-VIS spectra, for same batches of samples.

PEGylated paclitaxel (PEG-PTX) was synthesized by reacting 1 eq. of 4-Arm-(PEG-Amine) (10 kDa) with 4 eq. succinic anhydride modified PTX in the presence of EDC/NHS at the same reaction condition as conjugation of SWNT-PTX. Excess unreacted PTX was removed by filtration via 5 kDa MWCO filters. The concentration of PEG-PTX was measured by its absorbance spectrum. In the case of radiolabeled $^3$H-PTX, 100 µCi (~5 µg) of $^3$H-paclitaxel (Moravek Biochemicals) was mixed with 10 mg of regular non-radioactive paclitaxel and used for conjugation to obtain SWNT-PTX or PEG-PTX to impart radioactivity.

To make DSEP-PEG-PTX, as made DSPE-PEG5000-4-Arm-(PEG-Amine) (MW=16 kDa) was purified by dialysis (membrane MWCO=12-14 kDa) against water to remove excess 4-Arm-(PEG-Amine) (MW=10 kDa). Over 99% of unconjugated 4-Arm-(PEG-Amine) was removed as confirmed by MALDI mass spectrum. The purified product was lyophilized (yield after dialysis ~50%) and stored at −20° C. PTX conjugation was performed following the same procedure as described in the synthesis of PEG-PTX.

Taxol® was constituted following the clinical formulation. 6 mg/ml of paclitaxel with or without addition of $^3$H-paclitaxel (50 µCi/ml, ~2.5 µg/ml) was dissolved in 1:1 (v/v) mixture of Cremophor EL (Aldrich) and anhydrous ethanol (Fisher) and stored at −20° C.

All animal experiments were performed under a protocol approved by Stanford's Administrative Panel on Laboratory Animal Care (APLAC). The 4T1 tumor models were generated by subcutaneous injection of $2 \times 10^6$ cells in 50 µl PBS into the right shoulder of female Balb/c mice. The mice were used for treatment when the tumor volume reached 50-100 mm$^3$ (~6 days after tumor inoculation). For the treatment, 150-200 µl of different formulations of paclitaxel and SWNTs in saline was intravenously (IV) injected into mice via the tail vein every 6 days. The injected doses were normalized to be 5 mg/kg of paclitaxel. The tumor sizes were measured by a caliper every the other day and calculated as the volume=(tumor length)×(tumor width)$^2$/2. Relative tumor volumes (FIG. 24) were calculated as V/V$_0$ (V$_0$ was the tumor volume when the treatment was initiated).

Blood circulation was measured by drawing ~10 µl blood from the tail vein of tumor-free healthy Balb/c mice post injection of $^3$H labeled SWNT-PTX, Taxol® or PEG-PTX. The blood samples were dissolved in a lysis buffer (1% SDS, 1% Triton X-100, 40 mM Tris Acetate, 10 mM EDTA, 10 mM DTT) with brief sonication. Concentration of SWNTs in the blood was measured by a Raman method (18, 22) (see below). For $^3$H-PTX measurement, the blood lysate was decolorized by 0.2 ml of 30% hydrogen peroxide (Aldrich) and the radioactivity was counted by Tri-Carb 2800 TR (Perkin-Elmer) scintillation counter following the vendor's instruction. Raman measurement was done as described in the following section. Blood circulation data were plotted as the blood PTX or SWNT levels (unit: % ID/g) against time p.i. Pharmacokinetic analysis was performed by first-order exponential decay fitting of the blood PTX concentration data with the following equation: Blood concentration=A×exp (−t/λ), in which A was a constant (initial concentration) and t was the time p.i.

For the biodistribution study, 4T1 tumor bearing mice (tumor size ~200 mm$^3$) were sacrificed at 2 h and 24 h post injection of $^3$H labeled SWNT-PTX, Taxol® or PEG-PTX. The organs/tissues were collected and split into two halves for $^3$H-PTX and SWNT biodistribution studies. Majority of food residue and feces in the stomach and intestine was cleaned. For the $^3$H-PTX biodistribution, 50-100 mg of tissue was weighed and solubilized in 1 mL of scintillation counting compatible soluene-350 solvent (Perkin-Elmer) by incubation at 60° C. overnight and decolorized by 0.2 ml of 30% hydrogen peroxide. The $^3$H radioactivity in each organ/tissue was measured by applying the homogenous organ/tissue solutions to a Perkin-Elmer scintillation counter following the vendor's instruction. Biodistribution of $^3$H-PTX was calculated and normalized to the percentage of injected dose per gram tissue (% ID/g). Note that all the biodistribution and circulation tests were carried out at the treatment dose (normalized to 5 mg/kg of PTX).

Necropsy, Blood Chemistry and Histology Study 24 days after initiation of treatment, 3 mice from each treatment group (SWNT-PTX and Taxol®) and 2 age-matched female Balb/c control mice were sacrificed by CO$_2$ asphyxiation. Blood was collected via cardiac puncture at time of sacrifice for analysis of serum chemistries by the Diagnostic Laboratory, Veterinary Service Center, Department of Comparative Medicine, Stanford University School of Medicine. Serum chemistries were run on an Express Plus Chemistry Analyzer (Chiron Diagnostics) and electrolytes were measured on a 644 Na/K/Cl Analyzer (CIBA-Corning). A full necropsy was performed and all internal organs were harvested, fixed in 10% neutral buffered formalin, processed routinely into paraffin, sectioned at 4 microns, stained with hematoxylin & eosin (H&E) and examined by light microscopy. Examined tissues included: liver, kidneys, spleen, heart, salivary gland, lung, trachea, esophagus, thymus, reproductive tract, urinary bladder, eyes, lymph nodes, brain, thyroid gland, adrenal gland, gastrointestinal tract, pancreas, bone marrow, skeletal muscle, nasal cavities, middle ear, vertebrae, spinal cord and peripheral nerves.

Results

As-grown Hipco SWNTs functionalized by PEGylated phospholipid were used, made by sonication of SWNTs in a water solution of phospholipid-PEG and centrifugation to remove large bundles and impurities. The length distribution of the SWNTs was 20-300 nm with a mean of ~100 nm PEG functionalized SWNTs exhibited excellent stability without agglomeration in various biological media including serum. We used branched PEG chains for functionalization of SWNTs to afford more functional amine groups at the PEG termini for efficient drug conjugation. Paclitaxel was conjugated at the 2'-OH position (Deutsch, H. M., Glinski, J. A., Hernandez, M., Haugwitz, R. D., Narayanan, V. L., Suffness, M., and Zalkow, L. H. Synthesis of congeners and prodrugs. 3. Water-soluble prodrugs of taxol with potent antitumor activity. J Med Chem, 32: 788-792, 1989) to the terminal amine group of the branched PEG on SWNTs via a cleavable ester bond, forming a SWNT-PTX conjugate highly soluble and stable in aqueous solutions. The un-conjugated paclitaxel was removed thoroughly from the SWNT-PTX solution by filtration. The loading of paclitaxel on SWNTs was characterized to be ~150 per SWNT with ~100 nm length by radio-labeling method using tritium ($^3$H) labeled paclitaxel and a UV-VIS-NIR optical absorbance. The SWNT-PTX conjugate was found stable in physiological buffers with little drug release within 48 hours. In mouse serum, the release of PTX is faster but SWNT-PTX is still stable for hours, which is much longer than the blood circulation time of SWNT-PTX as described later. In vitro cell toxicity tests performed with a 4T1 murine breast cancer cell line found that SWNT-PTX exhibited similar toxicity as Taxol® and PEGylated PTX without any loss of cancer cell destruction ability. Consistent to the previous Examples, no noticeable toxic effect to cells was observed for plain nanotube carriers without drug even at high SWNT concentrations.

In Vivo Cancer Treatment on the Paclitaxel Resistant 4T1 Murine Breast Cancer Mice Model.

Female Balb/c mice bearing subcutaneously inoculated 4T1 tumors were treated with different forms of paclitaxel over several weeks including the clinical Taxol® formulation, PEGylated PTX, DSEP-PEG conjugated PTX (DSPE-PEG-PTX) and SWNT-PTX (14 mice in this group). The treatments were done by injecting Taxol®, PEG-PTX, DSEP-PEG-PTX and SWNT-PTX (at the same PTX dose of 5 mg/kg for all three formulations, once every 6 days) intravenously into tumor-bearing mice. The mice were observed daily for clinical symptoms and the tumor volume was measured by a digital caliper every other day. As shown in FIG. 24, a time-related increase in tumor volume was observed in the control untreated group and SWNT vehicle only group in which the tumors showed average fractional tumor volumes ($V/V_0$) of 10.1±1.7 and 9.8±2.0, respectively on day 22. Taxol® treatment, PEG-PTX treatment and DSPE-PEG-PTX treatment resulted in $V/V_0$ of 7.3±1.5 (P=0.06 vs untreated), 8.0±1.6 (P=0.18 vs untreated), 8.6±0.9 (P=0.33 vs untreated) on day 22, which represents tumor growth inhibition (TGI) of 27.7%, 20.8% and 14.9% respectively. In contrast, SWNT-PTX treatment resulted in a $V/V_0$ of 4.1±1.1 on day 22 (P=$2.4\times10^{-6}$ vs untreated, P=0.00063 vs Taxol®, P=0.00026 vs PEG-PTX, $2.7\times10^{-5}$ vs DSEP-PEG-PTX), representing a TGI of 59.4%, which is significantly more effective than Taxol®, PEG-PTX and DSPE-PEG-PTX.

Figure 25:
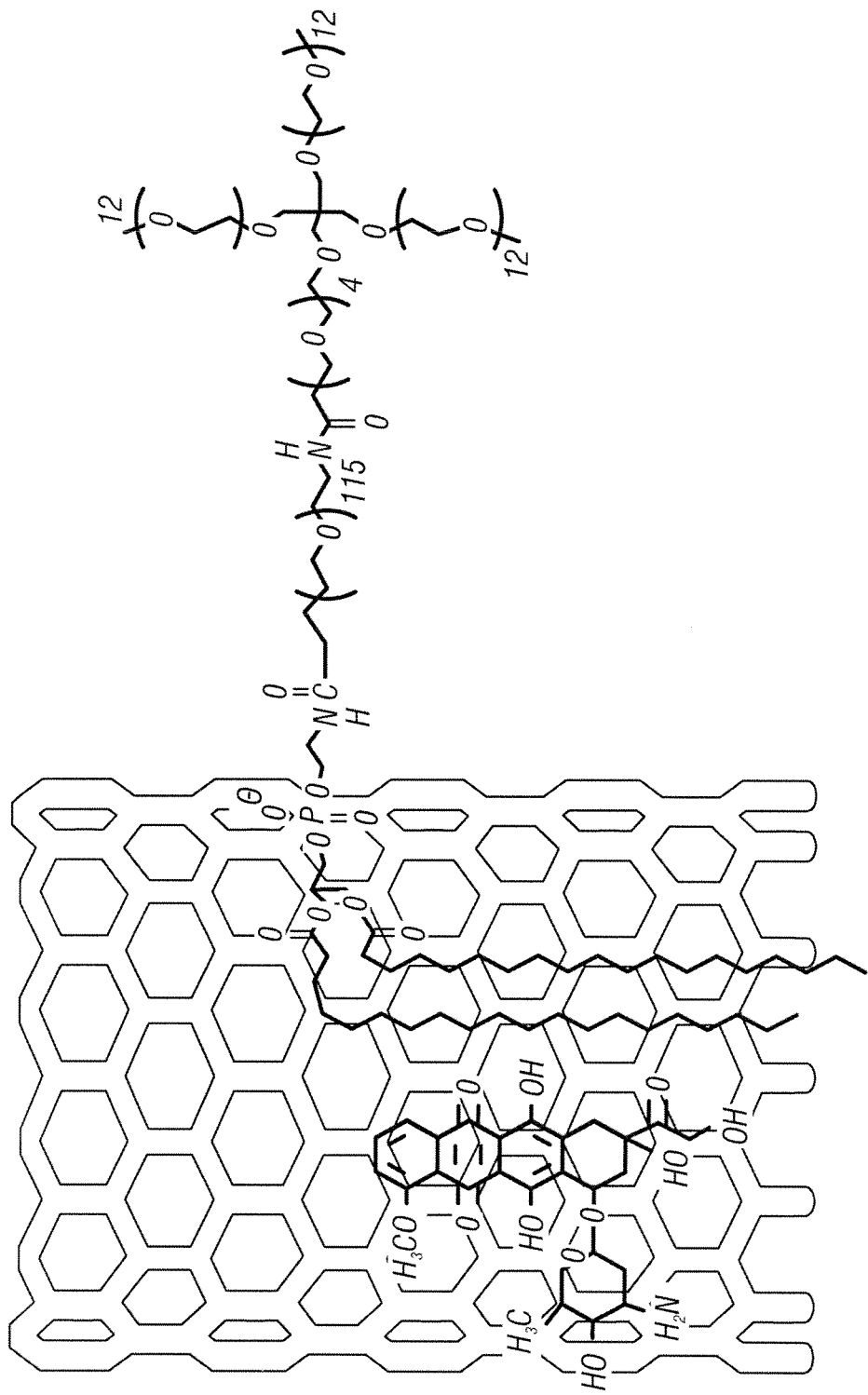
FIG. 25 is a schematic of a DOX-SWNT with branched PEG-lipid. SWNT is shown as coated with biocompatible branched PEG with hydrophobic phospholipid on the nanotube surface, along with a DOX molecule.
Figure 26D:
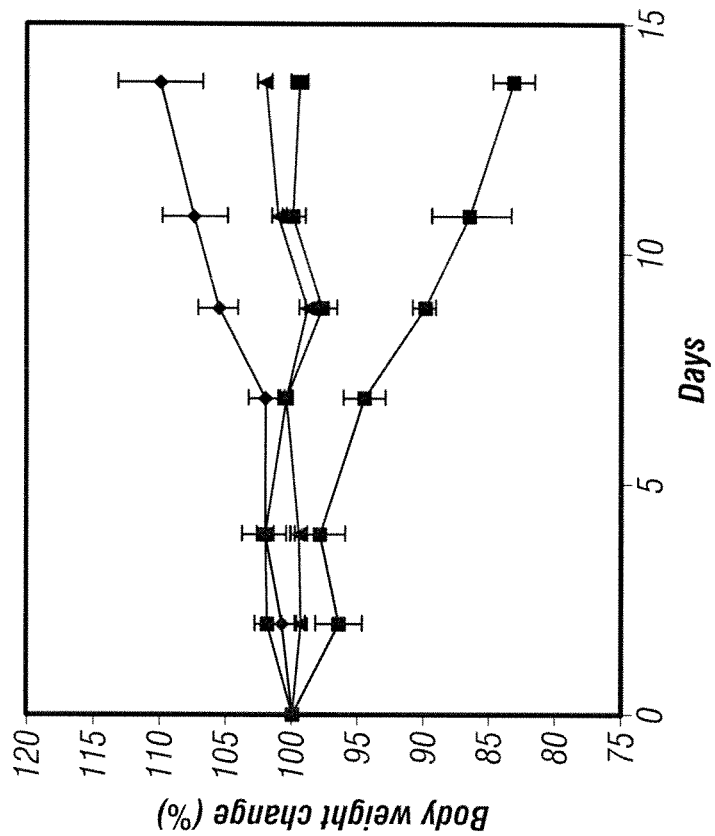
Figure 26C:
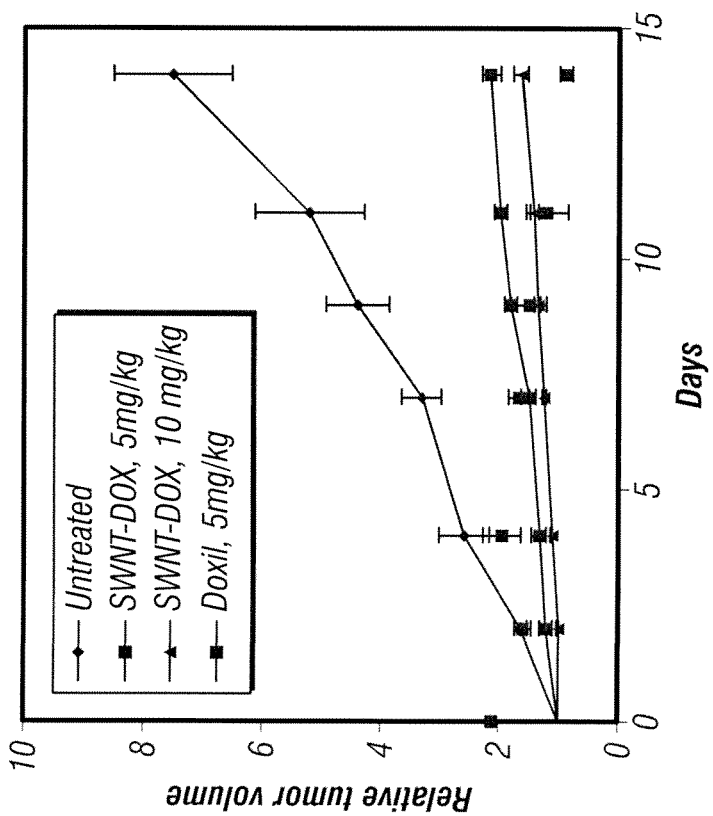

To investigate the tumor suppression mechanism, we performed terminal transferase dUTP nick end labeling (TUNEL) assay to examine the apoptosis level in the tumors from mice received different treatments. Similar to untreated tumor, Taxol® treated tumor showed only 2-3% of apoptotic cells. In contrast, high apoptosis level (~70%, P<0.0001 vs untreated and Taxol® treated tumors) was observed in SWNT-PTX treated tumor, consistent with the improved tumor growth inhibition efficacy (FIG. 25). The Ki-67 antibody staining method has been widely used as a cell proliferation marker to stain proliferation active cells in the G1, G2 and S phases of cell cycle. We found that cell proliferation in Taxol® treated tumor was as active as in untreated tumor. In the SWNT-PTX treated tumor case however, only ~20% of proliferation active cells were noted compared with the number in the untreated tumor. As the control, plain SWNT without PTX showed no effect to the tumors, proving the treatment efficacy of SWNT-PTX is due to PTX carried into tumors by nanotubes. Thus, both TUNEL staining and Ki67 staining results clearly confirmed the treatment efficacy of SWNT-PTX by inhibiting proliferation and inducing apoptosis of tumor cells.

In biodistribution studies similar to those described in connection with FIG. 23, it was found that SWNT-PTX afforded much higher PTX uptake in the tumor than Taxol® and PEG-PTX. The tumor PTX levels in the SWNT-PTX case was higher than those of Taxol® and PEG-PTX by 10 and 6-fold respectively at 2 h p.i., and by 6 and 4-fold higher respectively at 24 h p.i. The ability of higher drug delivery efficiency to tumor by our PEGylated SWNTs was striking and directly responsible for the higher tumor suppression efficacy of SWNT-PTX than the other formulations. This suggests that to reach similar tumor uptake of drug, much lower injected dose can be used by SWNT delivery than Taxol®, which is highly favorable for lowering toxic side effect to normal organs and tissues. An important gauge to drug delivery efficiency is the tumor-to-normal organ/tissue PTX uptake ratios (T/N ratios). We obtained significantly higher T/N PTX uptake ratios (for tumor over liver, spleen, muscle and other organs examined) in the case of SWNT-PTX than Taxol® and PEG-PTX (except at 2 h p.i. for spleen) at the 2 h and 24 h. This again makes SWNT-PTX highly favorable for high tumor suppression efficacy and low side effects.

We investigated the biodistribution of SWNTs injected as SWNT-PTX conjugates into mice by utilizing their intrinsic Raman scattering properties without relying on radio or fluorescent labels. (18, 29) We observed high uptake of SWNTs in the reticuloendothelial systems (RES)(18-20) including liver and spleen. Tumor uptake of SWNT-PTX increased significantly from ~1% ID/g at 30 min to ~5% ID/g at 2 h, indicating accumulation of SWNT-PTX during this period through blood circulation. Tumor uptake of SWNTs at 4.7% (std.=2.1%, n=3) ID/g was observed at 2 h p.i., reasonably consistent with the ~6.4% (std.=1.1%, n=3) ID/g PTX tumor uptake, suggesting that SWNT-PTX was taken up by tumor in a conjugated form. The SWNT biodistribution exhibited little change from 2 h to 24 h p.i., in contrast to the biodistribution of radiolabeled PTX. This suggests that the dissociation of PTX from SWNT carriers in vivo resulted from in vivo cleavage of the ester bond between SWNT and PTX is likely by carboxylesterases.

By themselves, PEGylated SWNTs have been found to be non-toxic to mice in vivo monitored over many months (Schipper, M. L., Nakayama-Ratchford, N., Davis, C. R., Kam, N. W. S., Chu, P., Liu, Z., Sun, X., Dai, H., and Gambhir, S. S. "A pilot toxicology study of single-walled carbon nanotubes in a small sample of mice," *Nature Nanotechnology*, 3: 216-221, 2008; Liu, Z., Davis, C., Cai, W., He, L., Chen, X., and Dai, H. "Circulation and Long-Term Fate of Functionalized, Biocompatible Single-Walled Carbon Nanotubes in Mice Probed by Raman Spectroscopy," *Proc. Natl. Acad. Sci. USA*, 105: 1410-1415, 2008.) We carried out a pilot toxicity study by treating healthy, tumor-free Balb/c mice with Taxol® and SWNT-PTX at the same 5 mg/kg PTX dose once every six days. We observed neither mortality nor noticeable body weight loss of the mice treated with SWNT-PTX and Taxol® compared to untreated control group at this relatively low PTX dose and injection frequency. Blood chemistry test was performed 24 days after initiation of the treatment, showing no physiologically significant difference among the 3 groups. Furthermore, hematoxylin & eosin (H&E) stained sections of the 25 organs and organ systems were examined, without noticing obvious abnormal damage in the main organs including the liver and spleen that had high SWNT uptake, which was consistent to the normal hepatic enzyme levels measured in the blood chemistry test. The observed lack of obvious toxic side effect was partly due to the low dose of PTX used as the maximum tolerable dose of PTX in the Taxol® case ~20-50 mg/kg. Achieving tumor treatment efficacy by SWNT-PTX at a PTX dose well below the toxic limit is owed to ability of drug delivery to tumors by SWNTs. However, further careful studies such as the hepatic macrophage function tests are required to examine any potential near-term or long-term side effect our SWNT-PTX.

Example 18

Nanoparticles Having Doxorubicin Attached by Supramolecular Bonding and Branched PEG Bonded by Lipids Reduce Lymphoma Tumors In this example, SWNTs were functionalized with branched PEG with doxorubicin linked to the SWNT by supramolecular bonding. Initial in vitro cellular toxicity experiments revealed slightly reduced toxicity of SWNT-DOX from free DOX. Pharmacokinetics and biodistribution of DOX in the free DOX and SWNT-DOX formulations were studied, showing prolonged blood circulation and increased tumor uptake in the later case. SCID mice inoculated with Raji B-cell lymphoma tumors were injected with different formulations of DOX including free DOX, Doxil® (doxorubicin HCl liposome injection, Ortho Biotech Products, L.P.), and SWNT-DOX at 5 mg/kg once a week. SWNT-DOX shows higher treatment efficacy than free DOX but lower than Doxil®, a FDA approved liposome-DOX formulation. However, significant side effects were observed for free DOX and Doxil® treated mice as evidenced by their drastic body weight drop but not for SWNT-DOX treated mice. By increasing the SWNT-DOX dose to 10 mg/kg, which is the lethal dose of free DOX and Doxil®, higher efficacy was achieved without showing obvious side effect.

Loading of Doxorubicin on Functionalized SWNTs

As made Hipco SWNTs were functionalized by phospholipid-branched PEG as described above. After removal of big bundles and impurities by harsh centrifugation and the excess surfactant by filtration through 100 kDa molecular weight cutoff (MWCO) filters, the PEGylated SWNTs were loaded with doxorubicin following the protocol in EXAMPLE 2. With branched PEG coating extended to the water phase to obtain the water solubility and biocompatibility of the nanotubes, their surface was packed with small aromatic doxorubicin molecules via supramolecular π-π stacking (FIG. 25). The SWNT-DOX complex had an average length of 100 nm and diameter of 2~3 nm as examined by automatic force microscope (AFM). The loading ratio of doxorobucin was determined by UV-VIS-NIR absorption spectra of SWNT-DOX. Depending on the solution pH and DOX concentration, the DOX loading on nanotubes can be as high as 4 gram DOX per 1 gram SWNTs. In this study, a mild loading was chosen to insure the best stability of SWNT-DOX complex. By finely adjusting the loading conditions, a loading of ~2.5 gram DOX per 1 gram SWNT was utilized in the tests described below.

Phospholipid-branched PEG was synthesized as described earlier. Raw Hipco SWNTs (0.2 mg/mL) were sonicated in a 0.2 mM solution phospholipid-branched PEG for 30 min with a cup-horn sonicator followed by centrifugation at 24,000 g for 6 h, yielding a suspension of SWNTs with non-covalent phospholipid-branched PEG coating in the supernatant. Excess surfactant was removed by repeated filtration through a 100 kDa MWCO filter (Millipore) and extensive washing with water.

DOX loading onto PEGylated SWNTs was done by simply mixing 0.5 mM of DOX with the PEGylated SWNTs at a nanotube concentration of ~0.05 mg/ml (~300 nM) at pH 8 overnight. Unbound excess DOX was removed by filtration through a 100 kDa filter and washed thoroughly with water until the filtrate became free of reddish color (corresponding to free DOX). The formed SWNT-DOX complex was characterized by UV-Vis-NIR absorbance spectra with a Cary-6000i spectrophotometer as described previously and stored at 4° C.

In Vitro Cell Assay

Raji human B-cell lymphoma cell line (from American Type Culture Collection, ATCC) was cultured in RPMI-1640 supplemented with 10% fetal bovine serum (FBS) and 1% Penicillin and streptomycin. Cells were plated in 96-wall plates and treated with different concentrations of free DOX, SWNT-DOX or Doxil® for 3 days. Cell viability after various treatments was measured by the MTS assay with CellTiter96 kit (Promega).

In Vivo Blood Circulation and Biodistribution Studies

Blood circulation was measured by drawing ~15 μl blood from the tail vein of Raji tumor bearing SCID mice post injection of free DOX or SWNT-DOX. The blood samples were dissolved in a lysis buffer 1 (1% SDS, 1% Triton X-100, 40 mM Tris Acetate, 10 mM EDTA, 10 mM DTT) with brief sonication. Concentration of SWNTs in the blood was measured by a Raman method. DOX measurement was carried out following the protocol previously reported with minor modification. In brief, DOX was extracted by incubating blood samples in 1 ml of 0.75 M HCl in isopropanol (IPA) at −20° C. overnight. After centrifuge at 24,000 g for 15 minutes, the supernatant was taken for fluorescence measurement using a fluorolog-3 fluorometer. A standard calibration curve with obtained by measuring fluorescence of extraction solutions with known DOX concentrations. DOX loaded on SWNTs can be completely pulled from nanotubes by the extraction solution with ~100% recover of fluorescence (DOX fluorescence is quenched once loaded on nanotubes).

Blood circulation data were plotted as the blood DOX or SWNT levels (unit: % ID/g) against time p.i. Pharmacokinetic analysis was performed by first-order exponential decay fitting of the blood PTX concentration data with the following equation: Blood concentration=$A \times \exp(-t/\lambda)$, in which A was a constant (initial concentration) and t was the time p.i.

For the biodistribution study, mice were sacrificed at 6 h post injection of free DOX or SWNT-DOX. The organs/tissues (0.1-0.2 g of each) were wet-weighed and homogenized in 0.5 ml of lysis buffer 2 (0.25M sucrose, 40 mM Tris Acetate, 10 mM EDTA) with a PowerGen homogenizer (Fisher Scientific). For DOX measurement, 200 μl of tissue lysate was mixed with 100 μl of 10% Titron X-100. After strong vortex, 1 ml of extraction solution (0.75M HCl in IPA) was added the samples were incubated at −20° C. overnight. After centrifuge at 24,000 g for 15 minutes, the supernatant was taken for fluorescence measurement. For SWNT measurement, 200 μl of tissue lysate was added with 200 μl of lysis buffer 1 and sonicated. After heating at 70° C. for ~2 h, clear homogenous tissue solutions were obtained for Raman measurement (see below).[18, 19] The biodistribution of DOX or SWNT in various organs of mice was then calculated and plotted in unit of % ID/g.

In Vivo Treatment

Each SCID mouse was subcutaneously injected with 10 million Raji cells on its back. The treatment was initiated when the tumors reached sizes of ~400 mm³ (2-3 weeks after tumor inoculation). The tumor bearing mice were i.v. injected with different formulations of DOX including free DOX, SWNT-DOX and Doxil at 5 mg/kg of normalized DOX dose (or 10 mg/kg for SWNT-DOX) as well as related controls weekly. The tumor sizes were measured by a caliper three times a week and calculated as the volume=(tumor length)×(tumor width)²/2. Relative tumor volumes were calculated as $V/V_0$ ($V_0$ was the tumor volume when the treatment was initiated). Mice were weighed with the relative body weights normalized to their initial weights.

In Vivo Pharmacokinetics and Biodistribution

We injected free DOX or SWNT-DOX to Raji tumor bearing SCID mice by intravenous (i.v.) injection via tail veins. Blood was drawn at different time points post injection (p.i.) with DOX concentrations measured by fluorescence spectra. After being loaded on nanotubes, the DOX circulation half-life increased from 0.21 h for the free DOX to 2.22 h for the SWNT-DOX formulation while the total area under curve ($AUC_{0-\infty}$) also increased from to 5.3 mg·h/L to 78.8 mg·h/L. The prolonged blood circulation of a drug is preferred in the cancer chemotherapy.

To examine the biodistribution of DOX, we sacrificed the mice at 6 h p.i. with every major organ taken. After tissue homogenization and DOX extraction, the concentration of DOX in each organ was measured by the fluorescence intensity. The DOX tumor uptake increased over one fold from 0.68 percent of injected dose per gram tissue (% ID/g) for free DOX to 1.51% ID/g in the SWNT-DOX case, which was likely due to the enhanced permeability and retention (EPR) effect that applies to many nanomaterials. As expected, a large amount of DOX in the SWNT-DOX formulation was accumulated in the reticuloendothelial systems (RES) including liver and spleen. Similar to most of nanomaterials, nanotubes tend to be taken up by the macrophages in the RES organs. Urine samples from mice injected with free DOX and SWNT-DOX were collected at 0.5 h and 4 h p.i. with their fluorescence spectra measured after dilution in PBS (50 μl urine in 1 ml PBS). Very strong DOX fluorescence was observed in urine from mice injected with free DOX at 0.5 h p.i. but dropped drastically at 4 h p.i, suggesting the fast urinal excretion of free DOX. In contrast, the DOX level in the urine of mice injected with SWNT-DOX was low at earlier time points (0.5 h) but increased later on (4 h). Considering that no SWNT was detected by Raman spectroscopy in these urine samples, the slow and persistent excretion of DOX from the urine in the SWNT-DOX case was likely due to the gradual dissociation of DOX molecules from nanotubes in vivo.

The intrinsic Raman scattering property of SWNTs can be used for ex-vivo detection. In additional to DOX measurement by fluorescence, we also examined the concentrations of SWNT in blood and other organs by Raman spectroscopy method as in Example 16. The concentrations of SWNT in the unit of % ID/g in the blood were consistent well with those of DOX, suggesting SWNT-DOX was circulating in the blood in the associated form. SWNT levels in other organs also followed the same trend of DOX biodistribution expect in the kidney, in which high DOX concentration was observed with only a low level of nanotubes. This combined with the factor that DOX has been detected in the urine indicates that although almost of SWNT-DOX is still in the associated form in the first few hours after administration, the loaded DOX is slowly falling off from nanotubes and being excreted via kidney. Most of nanotubes are too big to penetrate through kidney and will be slowly excreted via biliary pathway in feces.

In Vivo Treatment

Raji tumor bearing SCID mice were treated with different formulations of DOX at the weekly by i.v. injection. Plain SWNT and separated injections of plain SWNT plus free DOX were used as the controls. The tumor sizes were normalized to their initial size when the treatment was started (FIG. 26A-D). While the tumor sizes in untreated and plain SWNT treated groups increased 7.53±0.99 folds and 6.44±0.42 folds (P value=0.34 between these two groups) in two weeks, respectively, all the other groups showed delayed tumor growth. The free DOX (5 mg/kg) treated group and plain SWNT plus free DOX (5 mg/kg) treated group showed similar growth rate with their tumors enlarged 2.90±0.19 and 2.70±0.12 folds, respectively (P=0.56 between these two groups). SWNT-DOX treated group at the same DOX dose (5 mg/kg) showed 2.15±0.16 folds of tumor growth, which is lower than the free DOX group (P=0.016 vs free DOX group, P=0.039 vs plain SWNT+free DOX group). By increasing the SWNT-DOX dose to 10 mg/kg, improved treatment efficacy was achieved with 1.64±0.11 folds of tumor growth observed (P=0.018 vs 5 mg/kg SWNT-DOX, P=0.0004 vs 5 mg/kg free DOX).

As an important criterion to charge the toxicity of a chemotherapy drug, mice body weights were monitored during the treatment (FIG. 26B). While free DOX at the 5 mg/kg dose induced rapid body weight drop (~20% loss within two weeks) as well as mice death (2 out of 10 tested mice died), SWNT-DOX treated mice exhibited no obvious loss of body weights. Plain SWNT plus free DOX treatment did not help to reduce the body weight loss, proving that the decreased side effect of SWNT-DOX was not due to the nanotubes themselves. Even at the 10 mg/kg dose, which was a lethal dose of free DOX (all the tested mice died within 2 weeks), SWNT-DOX treatment still showed neither mouse death nor significant body weight drop. The minimized side effect of SWNT formulated DOX at high dose tremendously increases the therapeutic window of this drug for in vivo cancer treatment.

A PEGylated liposome formulation of doxorubicin, Doxil®, was also tested to compare with SWNT-DOX. Although 5 mg/kg of Doxil exhibited very high efficacy by shrinking the tumors at later time points, severe body weight loss and mice death (2 out of 5 tested mice) were observed for mice received Doxil. Compared with Doxil, SWNT-DOX showed lower efficacy but significantly reduced side effect to the mice.

SWNTs with ultra-high surface area are able to load doxorubicin efficiently by densely packing of DOX on the nanotube surface (~500 DOX per 100 nm of nanotube). Examples 12 and 13 show that DOX loaded on SWNTs is stable at neutral pH but released in acidic environments. Therefore SWNT-DOX taken up by cells will release free DOX quickly once acidified in endosomes/lysosomes and kill the cells.

Unlike free DOX, which is rapidly cleared out from blood circulation by urinal excretion, SWNT-DOX has a larger size that hampers its filtration through glomerulus. With branched PEG coating, the clearance of SWNT-DOX by macrophages is also slowed down, allowing a long circulation half-life in the blood. Prolonged blood circulation of a drug is generally preferable for better therapeutic effect.

Although the improvement in the treatment efficacy at the same drug dose is not drastic, SWNT-DOX shows significantly reduced side effect even at the lethal dose of free DOX. Interestingly, biodistribution data reveal large amounts of SWNT-DOX accumulated in the liver and spleen but not in the free DOX case, indicating that the RES organs including liver and spleen are more tolerable to doxorubicin chemotherapy. The reduced side effect in the SWNT-DOX case is likely due to the reduced diffusion ability of SWNT-DOX. While free DOX can diffuse into normal tissues easily by going through many biological barriers, SWNT-DOX is too large to penetrate barriers in normal tissue and organs. The pH dependent DOX releasing behavior of SWNT-DOX may also attribute to the improved efficacy/reduced toxicity. While normal organs and tissues have neutral pH, at which SWNT-DOX is stable without much releasing of toxic free DOX, tumor microenvironment is slight acidic[25] that will facilitate the dissociation of DOX from the SWNT carrier.

While 5 mg/kg of free DOX and Doxil® cause drastic body weight drop, SWNT-DOX shows no apparent side effect to the mice even at 10 mg/kg, which is lethal in the free DOX and Doxil® cases. The increased therapeutic window of our novel DOX formulation is promising for the development of future cancer chemotherapy.

Example 19

Figure 27:
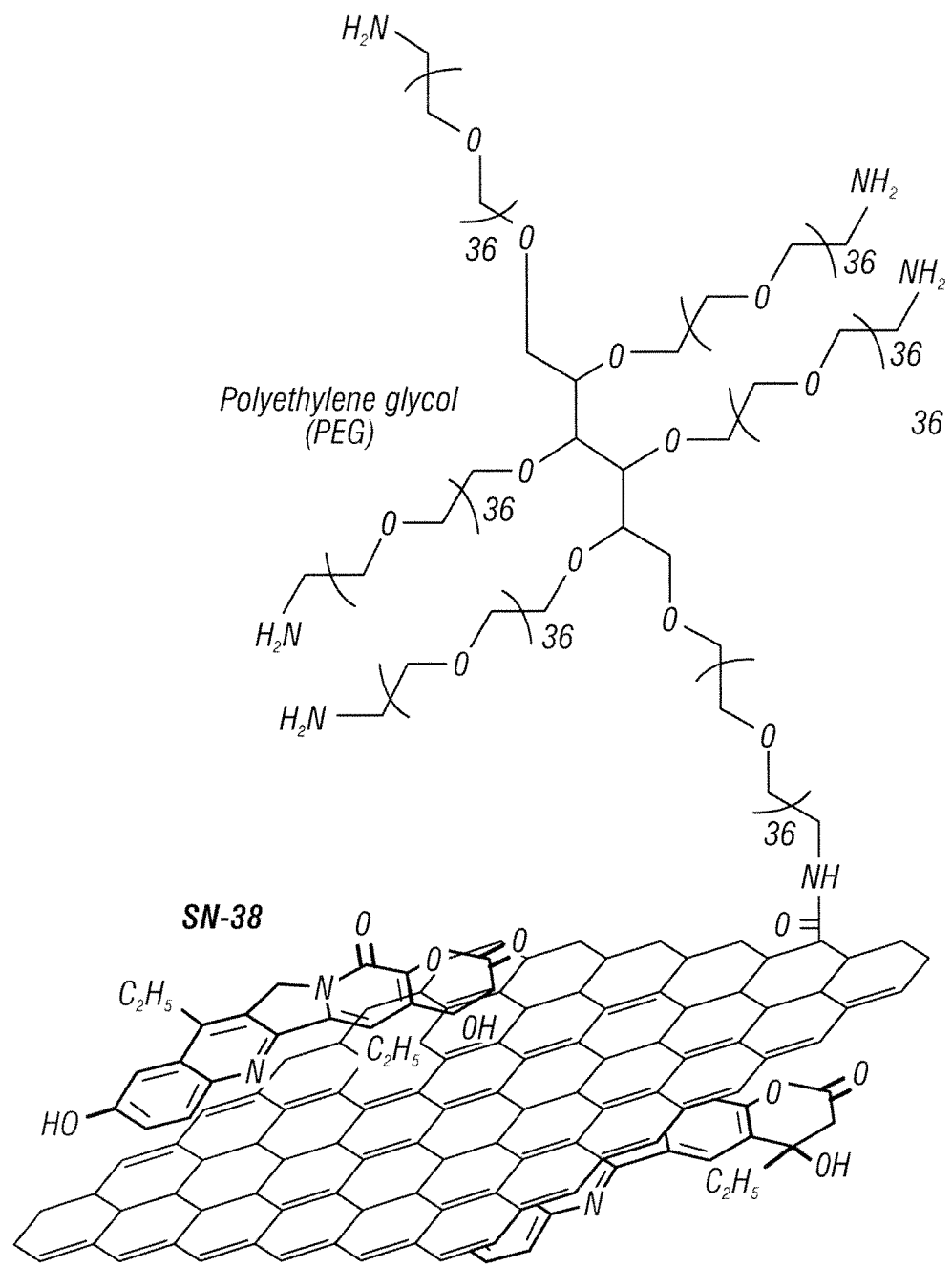
FIG. 27 is a schematic drawing of the drug SN38 loaded onto NGO-PEG (nano-graphene oxide) by supramolecular bonding; as indicated, there are 36 ethylene repeats on the 4 PEG arms, and one arm is attached to the sheet covalently. SN38 is polyaromatic, having both phenyl and heterocyclic rings.

Pegylated Nano-Graphene Oxide Delivers Insoluble Aromatic Drugs Bound to the Surface by Supramolecular Bonding Summary This example uses materials based on graphene, a 2D material with interesting physical properties, as described e.g., at Li, X. L.; Wang, X. R.; Zhang, L.; Lee, S. W.; Dai, H. J. *Science*, 2008, 319, 1229-1232. Described below are synthesized and functionalized nanoscale graphene oxide (NGO) sheets (<50 nm) made by covalently linking it to branched, biocompatible polyethylene glycol (PEG) to render high aqueous solubility and stability in physiological solutions including serum. The ability of graphene in attaching and delivery of aromatic, water insoluble drugs, which are supramolecularly bonded to the graphene sheets by π-π stacking was demonstrated in a recognized in vitro cell toxicity assay. As shown in FIG. 27, PEGylated NGO (NGO-PEG) readily complexed with a water insoluble aromatic molecule SN38, a camptothecin (CPT) analog, (as described in Tanizawa, A.; Fujimori, A.; Fujimori, Y.; Pommier, Y. J. *Natl. Cancer Inst.*, 1994, 86, 836-842) via non-covalent interaction. The NGO-PEG-SN38 complex exhibited excellent aqueous solubility and retains the high potency of free SN38 dissolved in organic solvents. The toxicity exceeds that of irinotecan (CPT-11, a FDA approved SN38 prodrug for colon cancer treatment) by 2-3 orders of magnitude.

Graphene Oxide

We prepared graphene oxide by oxidizing graphite using a modified Hummer's method.[3,11] This method is further described at Stankovich, S.; Dikin, D. A.; Dommett, G. H. B.; Kohlhaas, K. M.; Zimney, E. J.; Stach, E. A.; Piner, R. D.; Nguyen, S. T.; Ruoff, R. S, *Nature*, 2006, 442, 282-286, and Hummers, W. S.; Offeman, R. E. *J. Am. Chem. Soc.*, 1958, 80, 1339-1339.

Using mortar and pestle, 1 gram of graphite was ground with 50 grams of NaCl for a period of 10 minutes. NaCl was then dissolved and removed by filtration with water. This causes a small loss in graphite. The ground graphite flakes were then added to 23 ml of H2SO4 (98%) and left stirring for 12 hours. Afterwards, while keeping the temperature less than 20° C., 6 grams of KMnO4 was added. This was stirred at 40° C. for 30 minutes, then stirred at 90° C. for 90 minutes. (When the mixture reaches 70° C., temperature increases rapidly). Next, 46 ml distilled water were added, and the heat was increased to 105° C. for 25 min. The reaction was ended by a final addition of 140 ml distilled water and 10 ml 30% $H_2O_2$ solution. For purification, the resulting mixture was washed multiple times, first with 5% HCl solution and then with DI water. 200 ml of water were added to the graphite oxide product. The product was deposited on a substrate and imaged by AFM, which revealed that most of the GO sheets are single to few-layered with topographic height of 1-2 nm. The resulting graphene oxide (GO) was single layered and few-layered (2-3 layers).

The GO was soluble in water but aggregated in solutions rich in salts or proteins such as cell medium and serum. This was likely due to screening of the electrostatic charges and non-specific binding of proteins on the GO. To impart aqueous stability and prevent bio-fouling, we sonicated the GO sheets to make them into small pieces and conjugated a 6-armed PEG-amine stars to the carboxylic acid groups on GO via carbodiimide catalyzed amide formation.

In order to attach PEG, we introduced carboxylic acid functional groups. This was done by taking 10 ml of graphite oxide in water (~4 mg/ml) and bath-sonicating it for 1 hour. Following this, 10 ml of 3M NaOH was added to the graphite oxide solution and bath-sonicated for 3 hours.

The resulting PEGylated NGO exhibited excellent stability in all biological solutions tested including serum. PEGylation was further confirmed by infrared (IR) spectroscopy. The as-made GO sheets were 50-500 nm in size, whereas NGO-PEG was ~5-50 nm (as shown by AFM) due to sonication steps. The average thickness of GO was measured to be 1.8 nm with a standard deviation of 0.6 nm.

Afterwards, HCl was added to neutralize and the solution is filtered and rinsed. The final product is carboxylic acid modified graphite oxide (GO—COOH).

The modified GO was diluted by water until is ~1 mg/ml (O.D. of 0.4 at 808 nm with 1 mm optical path). It was then bath-sonicated with 10 mg/ml of 6-arm Polyetheylene Glycol-Amine (Sunbio Inc.) for 5 minutes. N-(3-Dimethylaminopropyl-N'-ethylcarbodiimide hydrochloride (EDC, from Sigma Inc.) was then added to reach 5 mM and the solution is bath sonicated for another 30 minute, followed by adding enough EDC to reach 4 mM and stirring for 12 hours. The reaction was terminated by adding Mercaptoethanol (Fluka Inc.). After 1 hr. of centrifugation (45 k rpm) in 2× phosphate buffer solution (PBS) for the solution, the supernatant was saved. The supernatant was the final product, NGO-PEG. The PEGylation was confirmed by IR spectroscopy of NGO-PEG in which pronounced C—H and C—O vibration bands of the PEG chains were observed. The fact that NGO-PEG was stable in serum without aggregation also confirmed successful PEGylation. The resulting structure is shown in FIG. 27.

Binding of SN38 to NGO-PEG

SN38 (7-ethyl-10-hydroxycamptothecin) is a potent topoisomerase I inhibitor and inhibitor of tumor growth, as described at Tanizawa, A.; Fujimori, A.; Fujimori, Y.; Pommier, Y. *J. Natl. Cancer Inst.*, 1994, 86, 836-842. CPT-11 is a related compound originally synthesized by the introduction of an ethyl group at the 7-position of camptothecin and a hydroxyl group at the 10-position, which formed an ester linkage with a piperidinopiperidino carbonyl group. The ester linkage enhanced the polarity of the compound. To be active, CPT-11 currently used in clinic, has to be metabolized to SN38 after systematic administration. However a large amount of CPT-11 is excreted before transforming to SN38 or metabolized to other inactive compounds.[14] The water insolubility has prevented the direct use of SN38 in the clinic. SN38 was complexed with NGO-PEG (FIG. 27 by simple mixing of SN38 dissolved in DMSO with a NGO-PEG water solution. The excess, uncoupled SN38 precipitated and was removed by centrifugation. Repeated washing and filtration were used to remove DMSO and any residual free SN38. UV-VIS spectrum of the resulting solution revealed SN38 peaks superimposing with the absorption curve of NGO-PEG, suggesting loading of SN38 onto NGO-PEG. Based on the extinction coefficients, we estimated that 1 gram of NGO-PEG loaded ~0.1 gram of SN38. An increase in sheet thickness was observed after SN38 loading on NGO-PEG. A control experiment revealed no loading of SN38 on PEG polymer in a solution free of NGO.

Unlike free SN38, which was very insoluble in water, NGO-PEG-SN38 complexes were water soluble at concentrations up to ~1 mg/mL (in terms of SN38). Fluorescence spectra of NGO-PEG-SN38 and free SN38 at the same SN38 concentration showed drastic fluorescence quenching of SN38 in the NGO-PEG-SN38 case, suggesting close proximity of SN38 to the NGO sheets. We suggest that binding of SN38 onto NGO-PEG was non-covalent in nature, driven by hydrophobic interactions and π-π stacking between SN38 and aromatic regions of the graphene oxide sheets. The existence of aromatic conjugated domains on GO has been shown by NMR previously (Lerf, A.; He, H. Y.; Forster, M.; Klinowski, J., *J. Phys. Chem. B*, 1998, 102, 4477-4482).

SN38 was purchased from Guanyu Bio Inc from China. 5 ml of 0.05 mg/ml NGO-PEG in water was mixed with 0.5 ml of 2.5 mM SN38 DMSO solution and stirred overnight at room temperature. Excess SN38 precipitated as solid was removed by centrifuge. The supernatant was filtered through a 0.45 μm filter to fully remove any solid. The solution was then filtered through a 30 kDa molecular weight cutoff filter (Millpore) to remove the small amount of solubilized free SN38. NGO-PEG-SN38 retained in the filter was washed 4 to 6 times and re-suspended in water. The formed NGO-PEG-SN38 was stored at 4° C.

To determine the stability of SN38 loaded on NGO-PEG and release rate, we incubated NGO-PEG in phosphate buffer saline (PBS) and mouse serum respectively at 37° C. and measured the percentage of retained SN38 on NGO-PEG. We found that SN38 on NGO-PEG exhibited negligible release from NGO in PBS and ~30% release in serum in 3 days. This suggested strong non-covalent binding of SN38 on graphene oxide sheets. The slow but finite release of SN38 in serum was likely caused by the binding of SN38 by serum proteins. These results show that the complex is useful for drug delivery. Fluorescence method was used to measure the retained SN38 concentrations after incubating NGO-PEG-SN38 in buffer and serum. Because the fluorescence was quenched once loaded on NGO-PEG-SN38, SN38 should be detached from NGO-PEG in order to use fluorescence to quantitatively measure its concentration. We found that after addition of isopropanol (IPA) into the NGO-PEG-SN38 water solution, the loaded SN38 will be fully released as evidenced by the recovery of SN38 fluorescence at 560 nm.

Cell Toxicity

We used the multicellular tumor spheroids (MTS) systems for assaying tumor inactivating agents. See, J. M. Yuhas et al., "In Vitro Analysis of the Response of Multicellular Tumor Spheroids Exposed to Chemotherapeutic Agents in Vitro or in Vivo," 38 *Cancer Res.*, 3595-3598 (1978).

HCT-116 colon cancer cell line, OVCAR-3 ovarian cancer cell line, U87MG glioma cell line and MDA-MB-435 breast cancer cell line were all obtained from American Type Culture Collect (ATCC) and cultured in the recommended conditions. For the in vitro cell toxicity assay, cells were plated in 96 well plates and added with desired concentrations of NGO-PEG, NGO-PEG-SN38, free SN38 (dissolve in DMSO and diluted in PBS) and CPT-11 added. After incubation for 72 hours, relative cell viability was measured by standard MTS assay using a CellTiter 96 kit (promega). For NGO-PEG toxicity test, cell medium containing NGO-PEG was changed to fresh medium at 72 h before cell viability test to avoid the dark color of NGO-PEG at high concentrations, which interferes the absorbance reading in MTS assay.

Figure 28A:
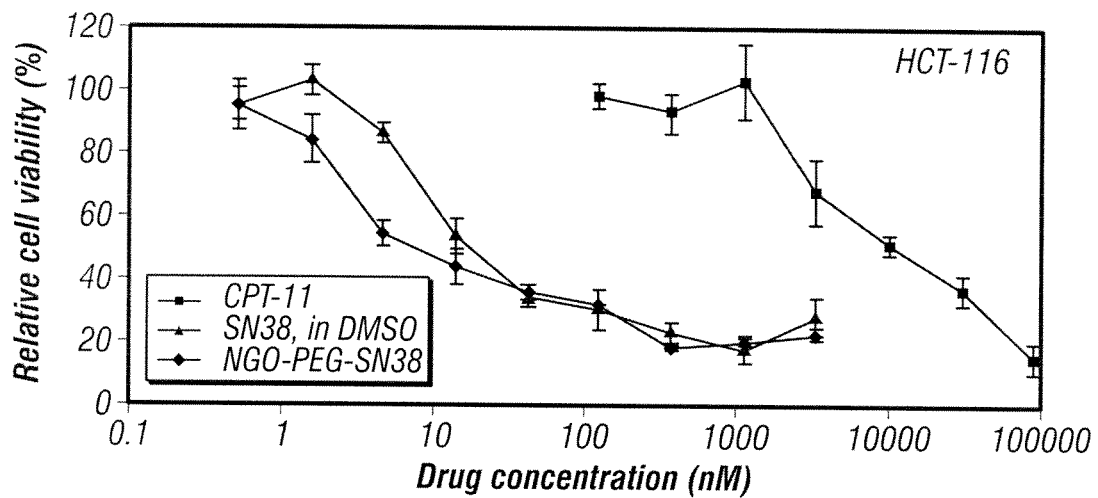
FIG. 28 (A) and (B) are graphs showing relative cell viability of nanographene oxide attached to PEG (as in FIG. 27), compared to different formulations In FIG. 28 (A) is shown the relative cell viability (versus untreated control) data of HCT-116 cells incubated with CPT-11, SN38 and NGO-PEG-SN38 at different concentrations for 72 h. Free SN38 was dissolved in DMSO and diluted in PBS. Water-soluble NGO-PEG-SN38 showed similar toxicity as SN38 in DMSO and far higher potency than CPT-11.
Figure 28B:
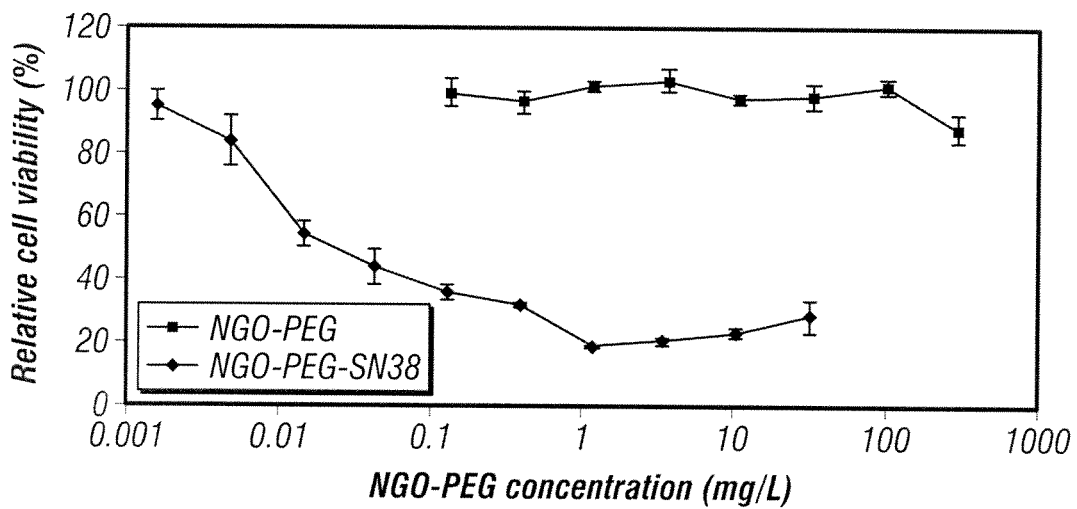

The MTS assay found that NGO-PEG-SN38 afforded highly potent cancer cell killing in vitro with a human colon cancer cell line HCT-116. The water-soluble drug CPT-11 was found to be the least toxic, with a 50% growth inhibition concentration (IC50) of ~10 μM (FIG. 28). Our water-soluble NGO-PEG-SN38 exhibited high potency with IC50 values of ~6 nM for HCT-116 cells, which is ~1000 fold more potent than CPT-11 and similar to that of free SN38 dissolved in DMSO (FIG. 28A). The high potency of NGO-PEG-SN38 was also observed with various other cancer cell lines tested, as shown in the following table:

TABLE 3

IC50 values (nM) of different cell lines after 72 h drug incubation.

| Cell line | CPT-11 | SN38 | NGO-PEG-SN38 |
|---|---|---|---|
| HCT-116 (colon) | 11,000 | 15 | 6 |
| OVCAR-3 (ovarian) | 3,000 | 0.3 | 0.12 |
| U87MG (glioma) | >20,000 | 67 | 50 |
| MDA-MD-435 (breast) | 6,000 | 3 | 2 |

Importantly, no obvious toxicity was measured for various concentrations of plain NGO-PEG without drug loading (FIG. 28B), suggesting that the PEGylated nanographene oxide sheets were not cytotoxic by themselves. Apoptosis assay further confirmed no obvious increase of cell death or apoptosis after incubating cells with plain NGO-PEG. The cellular uptake of NGO-PEG was likely via endocytosis as evidenced by confocal fluorescence microscopy data.

We found that the strategy of attaching various types of insoluble, aromatic drug molecules onto NGO-PEG via simple adsorption was general. Other drugs that we succeeded in loading onto NGO-PEG by simple adsorption included different camptothecin analogs and Iressa (gefitinib), 4-quinazolinamine,N-(3-chloro-4-fluorophenyl)-7-methoxy-6-[3-(4-morpholinyl)propoxy, an potent epidermal growth factor receptor (EGFR) inhibitor. It is further described in Johnson, D. H. Lung Cancer 2003, 41, S23-S28. It has the formula

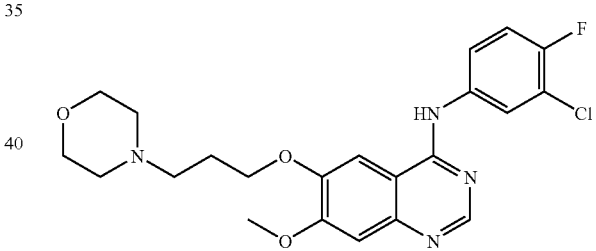

Graphitic nanocarriers including nanographene sheets and carbon nanotubes afford strong noncovalent binding with aromatic drugs via supramolecular bonding, probably through simple adsorption or π-π stacking. With the use of the present graphene sheets as drug carriers, both sides of a single sheet could be accessible for drug binding. The unique 2D shape and ultra-small size (down to 5 nm) of NGO-PEG may offer certain advantages, as well as advantages in low cost and large production scalability.

Example 20

Other Graphene sheets

The previous example describes the preparation of graphite oxide sheets by harsh oxidation using the Hummer's method. However, irreversible defects and disorder exist in the GO sheets. The reduced GO exhibits non-metallic behavior with decreased conductance by about 3 orders of magnitude upon cooling down to low temperature, while pristine graphene is nearly metallic. Thus, one may use other graphene sheet materials, which are made hydrophilic and used as drug carriers. For example, we have obtained pristine graphene nanoribbons (GNR) by sonicating thermally exfoliated graphite in a 1,2-dichloroethane (DCE) solution of poly(m-phenylenevinylene-co-2,5-dioctoxy-p-phenylenevinylene)(PmPV). These are described in Li, X. L., Wang, X. R., Zhang, L., Lee, S. W., Dai, H. J., "Chemically Derived, Ultrasmooth Graphene Nanoribbon Semiconductors," *Science*, (2008).

Figures 29A, 29B, 29C:
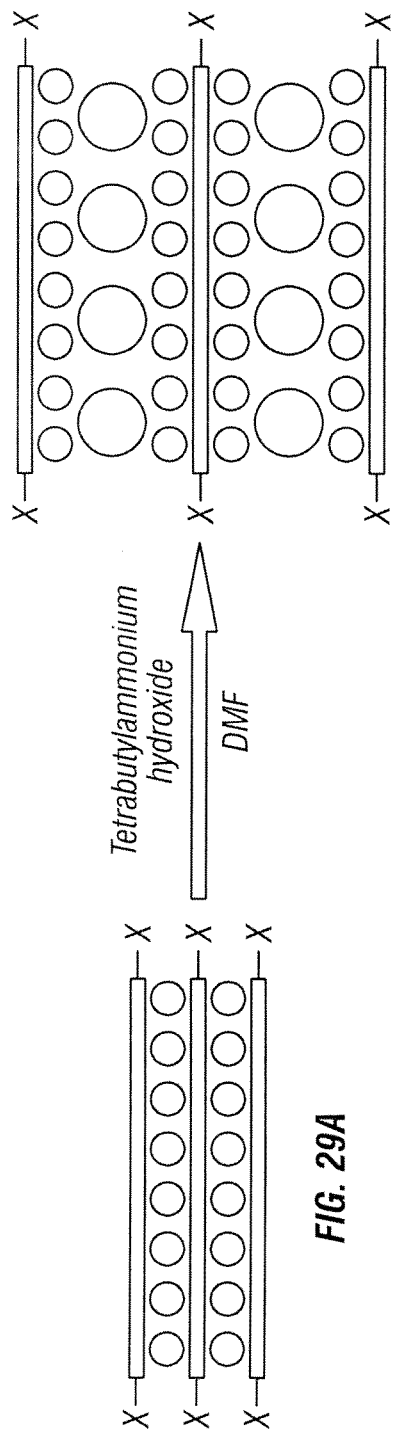
FIG. 29 is a schematic illustration of a three-step process for preparing chemically derived single layer graphene sheets (GS) from solution phase. Step (a) shows the exfoliated graphite re-intercalated with sulphuric acid molecules (teal spheres) between the layers. Step (b) shows TBA (large spheres) insertion into the intercalated graphite. Step (c) shows GS (graphene sheet) coated with two DSPE-mPEG molecules. These sheets are used as nanoparticles according to the present invention.

In a new method to make pristine graphene sheet, we started by first exfoliating commercial expandable-graphite (160-50N, Grafguard Inc.) by brief (60 s) heating to 1000° C. in forming gas. We then ground the exfoliated graphite, re-intercalated with oleum (fuming sulfuric acid with 20% free $SO_3$), and inserted tetrabutylammonium hydroxide (TBA, 40% solution in water) into oleum intercalated graphite (FIG. 29A) in N,N-dimethylformamide. The bars represent graphene; the smaller spheres represent sulfate. We then sonicated the TBA-inserted oleum-intercalated graphite (FIG. 29B) in a DMF solution of 1,2-distearoyl-sn-glycero-3-phosphoethanolamine-N-[methoxy(polyethyleneglycol)-5000 (DSPE-mPEG) for 60 mins to form a homogeneous suspension. The larger spheres represent DMF. Centrifugation was used to remove large pieces of materials from the supernatant to yield individual suspended sheets, which were then Pegylated (FIG. 29C). This method easily obtained large amounts of graphene sheets suspended in DMF and could be transferred to other solvents including water and organic solvents.

We used atomic force microscopy (AFM) to characterize the materials deposited on substrates from the supernatant and observed ~90% single layer GS with various shapes and sizes. For over hundreds of graphene sheets measured, we found that the single-layer GS have an average size of about 250 nm and topographic height of ~1 nm, (about one carbon atom thick). Transmission electron microscopy (TEM) and electron diffraction (ED) were used to characterize the single layer GS. The ED pattern of our GS was similar to that of 'peeled off' graphene, (Meyer et al. "The structure of suspended graphene sheets," *Nature*, 446, 60-63 (2007)), suggesting well-crystallized single layer graphene structure.

Our starting expandable graphite was prepared by chemical intercalation of oxidizing sulfuric acid and nitric acid. Upon heating, they exfoliated violently due to volatile gaseous species released from the intercalant. Most of the exfoliated graphite was still in multi-layer graphene form. In order to get single layer graphene sheets, we invoked re-intercalation by oleum, a chemical known to strongly debundle carbon nanotubes due to intercalation. TBA was a molecule capable of inserting and expanding the distance between heavily oxidized graphite layers. (Liu, Z. H., Wang, Z. M., Yang, X. J., Ooi, K., "Intercalation of organic ammonium ions into layered graphite oxide," *Langmuir*, 18, 4926-4932 (2002). Without wishing to be bound by any one theory, we suggest that TBA also insert into oleum-intercalated graphite to increase the distance between adjacent graphitic layers (FIG. 29B), which facilitated the separation of graphene sheets upon sonication in a surfactant solution. This was evidenced by that without the TBA treatment step, the yield of single layer GS was extremely low by the otherwise identical method. We also found that DMF was a better solvent than water for our method. Further, DSPE-mPEG was a surfactant capable of suspending nanotubes, and was another important factor to obtaining homogeneous suspension of GS.

Figure 30:
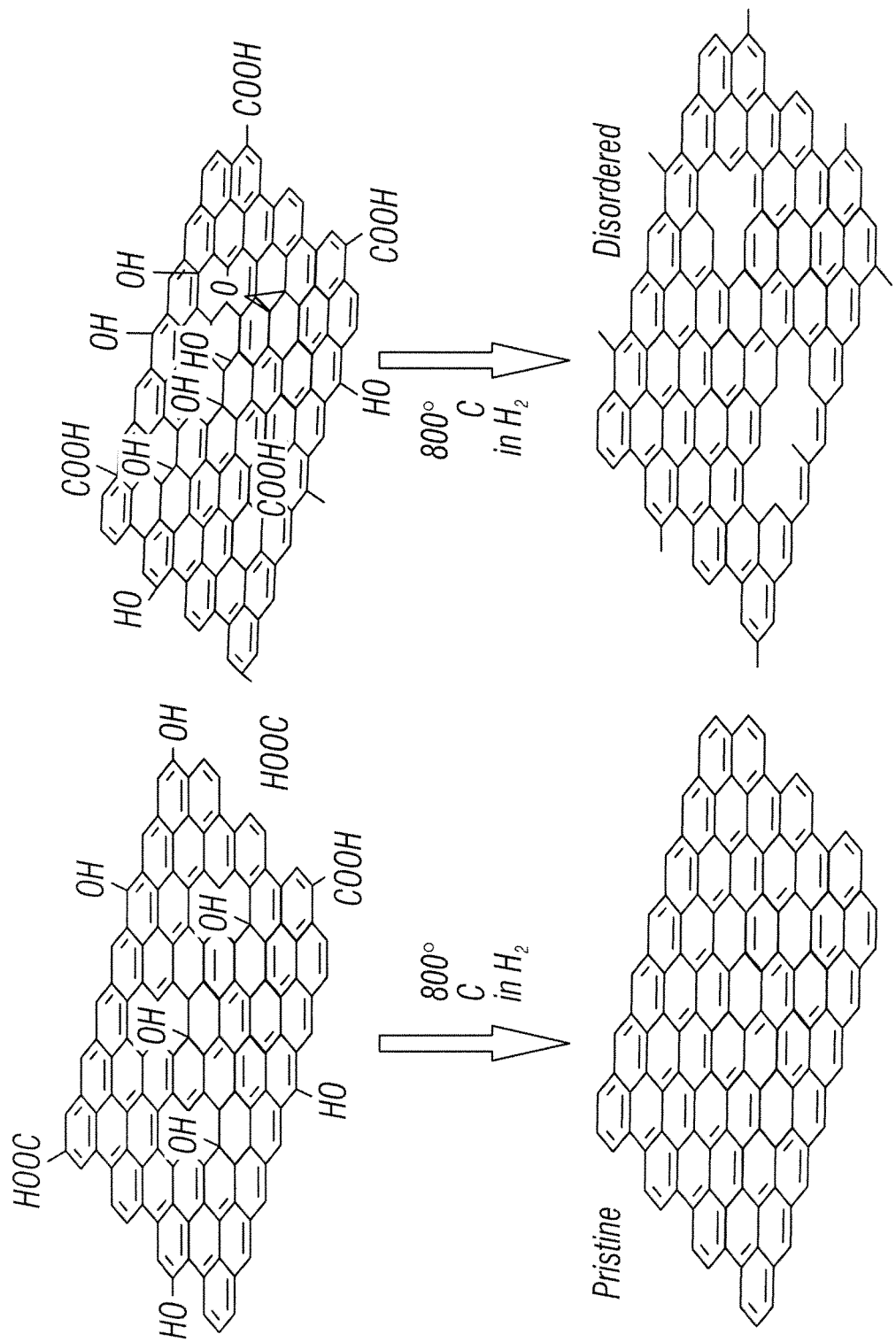
FIG. 30 is a schematic drawing of a graphene sheet (left) and a graphene oxide sheet (right), showing atomic structure of the as made and annealed sheets. Broken bonds and missing atoms are shown in the disordered graphene oxide sheet.

Our weak oleum treatment condition (soaking in oleum at room temperature for one day) is important to obtain the intermediate, nearly pristine as-made GS and final pristine GS upon thermal annealing. The conjugate graphene plane is largely free of irreversible modifications through the treatment steps. Room temperature oleum treatment is much less oxidative than the Hummer's method, evidenced by the as-made GS exhibiting significantly fewer functional groups than as-made Hummer's GO in infrared (IR) spectra. The IR spectrum of as-made GS showed weaker signals of carboxylic groups than the Hummer's GO. X-ray photoelectron spectroscopy (XPS) Our as-made GS was nearly pristine with small but noticeable signals at higher binding energy corresponding to small amount of C—O species. That is, the graphene sheet made according to the present method contained an ordered array of fused aromatic rings, without carbon atoms or bonds. Prior to heating, both methods produced hydroxyl and carboxyl groups attached to some carbon atoms in the sheet. These species were removed by 800° C. $H_2$ annealing, indicating the formation of pristine graphene in the case of the present method. The annealed GS exhibited the same XPS spectrum as a pristine highly oriented pyrolytic graphite (HOPG) crystal. This confirmed the highly pristine nature of the final GS product. The proposed schematic structures of our GS (pristine) and Hummer's GO (disordered) is shown in FIG. 30. Oxidization of our GS was relatively mild and the few covalently attached functional groups such as carboxylic group and hydroxyl group were most likely at the edges of as-made GS. The Hummer's GO was heavily oxidized with disrupted conjugation in the plane, missing carbon atoms in the plane (holes, like in oxidized carbon nanotubes), and abundant functional groups such as epoxide, hydroxyl, carbonyl and carboxyl groups at both the edges and in the plane (FIG. 30, left) Importantly, these abundant functional groups weaken the van der Waals interactions between the layers of GO and make them hydrophilic, which is the reason of single-layer GO exfoliation in aqueous media to form stable suspensions without the need of insertion agent such as TBA or the assistance of surfactant for suspension. Thermal annealing removed some of the functional groups but was unable to repair holes and other defects irreversibly formed within the plane of Hummer's GO sheets.

To explore the utility of our high quality graphene sheet, we transferred large quantities of GS from DMF to organic solvent DCE with excellent stability against agglomeration. The fact that our as-made GS was stably suspended in DCE without additional surfactant indicates high hydrophobicity of the graphene, consistent with low degree of graphene oxidation. In contrast, Hummer's GO were highly hydrophilic and completely insoluble in organic solvents. The organic stability of our GS enabled Langmuir-Blodgett (LB) films to be made on various transparent substrates including glass and quartz for producing transparent and conducting films. This was done by adding GS suspensions onto water subphase, vaporizing the DCE solvent from water surface, compressing the floating GS and transferring the GS LB film onto a substrate by dip-coating. We were able to transfer GS repeatedly to achieve multi-layer films. The 1-, 2-, and 3-layer LB films on quartz afforded a sheet resistance of ~150 k, 20 k, and 8 k ohm at room temperature and a transparency (defined as transmittance at 1000 nm wavelength) of ~93%, 88% and 83% respectively.

The single layer graphene sheets (GS) preparation started by exfoliating expandable graphite (160-50N of Grafguard Inc.) at 1000° C. in forming gas for 60 s. Then exfoliated graphite (~10 mg) was grounded with NaCl crystallites for 3 mins forming a uniform grayish mixture. Small pieces of exfoliated graphite were separated and collected by dissolving NaCl with water and filtration. The resulting sample was then treated with oleum at room temperature for a day. After complete removal of acid by filtration and repeated washing, the resulting sample was ultra-sonicated in DMF (10 mL) solution of TBA (130 µl) for 5 mins. The suspension was put at room temperature for 3 days to let the TBA fully inserted into graphene layers. Then 5 mL suspension was taken out and bath-sonicated with DSPE-mPEG (Laysan Bio. Inc., Arab, Ala.) (15 mg) for 1 hr forming a homogeneous suspension. After centrifuging the suspension at 24 kg for 3 mins, we obtained black suspension with mostly single layer GS retained in the supernatant.

Given the present example, one may prepare drug conjugates by bonding the drugs directly to the present sheets by supramolecular bonding, or by bonding the drugs to the PEG, which is attached by a lipid chain to the graphene sheet by supramolecular bonding.

Example 22

Nanographene-Oxide Single Layer Sheet Covalently Linked to Hydrophilic Polymer (PEG) Linked to a Monoclonal Antibody and to Doxorubicin by Supramolecular Bonding Introduction In this example, nano-graphene oxide (NGO), i.e., single-layer graphene-oxide sheets down to a few nanometers in lateral width, are treated to impart solubility and compatibility in biological environments. We obtain size separated pegylated NGO sheets that are soluble in buffers and serum without agglomeration. π-π stacking is used for ultra-high drug loading onto NGO for selective cancer cell destruction. Owing to the optical properties, large surface area on both sides of the sheets, useful non-covalent interactions with aromatic drug molecules and ultra-low cost, NGO is shown to be a promising new material for biological and medical applications.

Ultrasmall graphene oxide down to <10 nm was prepared in a low cost and scalable fashion. Aqueous stability to the NGO in buffer solutions and other biological media was obtained by covalently grafting polyethylene glycol (PEG) star-polymers onto the chemically activated surfaces and edges. A rate separation method was developed to separate the pegylated NGO according to size. Interestingly, the NGO sheets showed photoluminescence from visible to the near-infrared (NIR) range, which was used for cellular imaging with little background. Furthermore, an aromatic anti cancer drug doxorubicin was loaded onto the NGO sheets at an ultrahigh capacity via simple π-π stacking. The drug was selectively shuttled into cancer cells by antibody guided targeting of NGO for selective cancer cell killing.

Preparation of Graphene Sheets

Figure 31:
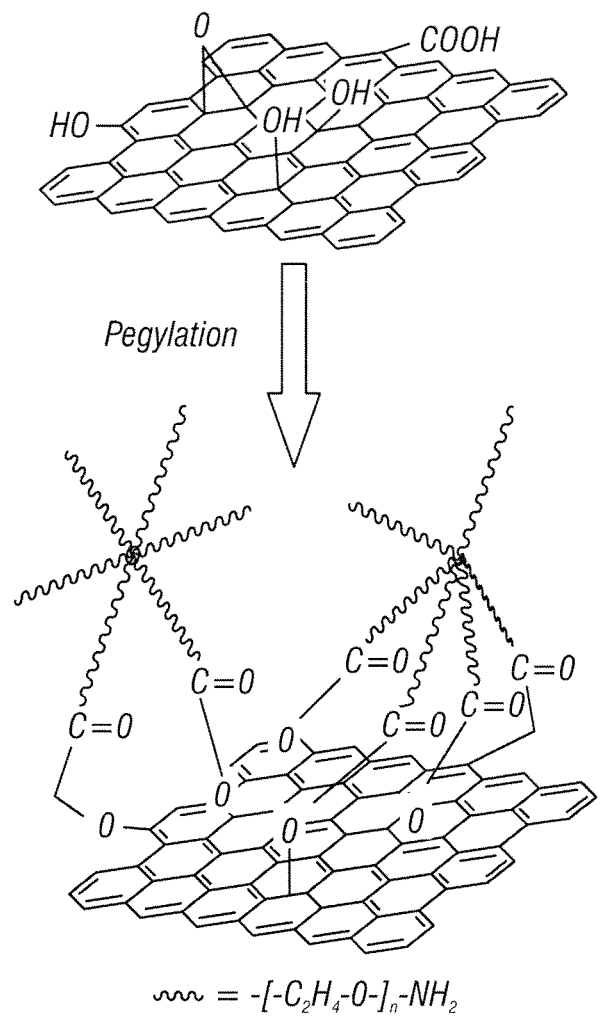
FIG. 31 is a schematic drawing showing a method of synthesis of nanographene oxide and its covalent pegylation. Active agents may then be bound to the surface of the graphene sheet by supramolecular bonding.

The preparation of ultrasmall graphene sheets started from graphene oxide (GO) made by using a modified Hummer's method (FIG. 31). Briefly, expandable graphite (Graftech Inc.) was used as starting material instead of graphite flakes for more uniform oxidization. The graphite powder was ground with NaCl salt crystals to reduce the particle size, and then soaked in sulfuric acid for 8 h for intercalation. We then added oxidizing $KMnO_4$, increased the oxidization temperature and extended the oxidization time to ~2 h to make fully and uniformly oxidized graphite. The products were washed with diluted acid and water. The resulting GO sheets after 1 h sonication were mostly single layered (>70%), 10-300 nm in size, as shown by AFM.

Infrared (IR) spectroscopy revealed the existence of —OH (~3400 cm-1), C=O (1715 cm-1), and C=C (1580 cm-1) functional groups on as made GO. We then activated the GO sample with chloroacetic acid in a strong basic condition to activate groups like epoxides and esters, and to convert the hydroxyl groups to carboxylic acid (—COOH). The intermediate product, named GO—COOH, had increased water solubility and more carboxylic acids for consequent PEGylation.

Graphite oxide for chemical activation and pegylation was made by modified Hummer's method 10 using expandable graphite flake (Graftech) as starting material. 1 g Expandable graphite flake was ground with 50 g NaCl solids for 10 minutes. Water was added inside to dissolve NaCl and filtration was used to remove them (lose ~15% carbon). Grinded expandable graphite flake (0.85 g) was stirred in 23 ml H2SO4 (98%) for 8 h. 3 g KMnO4 was gradually added (T<20° C.), and stirred at 35-40° C. for 30 min and 65-80° C. for 45 min. 46 ml water was added and heated at 98-105° C. for 30 min. The reaction was terminated by addition of 140 ml distilled water and 10 ml 30% $H_2O_2$ solution. The mixture was washed with 5% HCl aqueous solution and DI water. 160 ml water was added to the final product and vortexed well to make an even suspension. A small fraction (e.g., 5 ml) was diluted by 2, then sonicated for 1 h to make a clear solution. 1.2 g NaOH and 1.0 g chloricacetic acid (Cl—CH2-COOH) was added into the 10 ml GO suspension (~2 mg/ml) and bath sonicated for 1-3 h 14. The obtained GO—COOH solution was neutralized, and purified by rinsing and filtrations. GO—COOH suspension was diluted by water to make OD=0.4 at 808 nm (1 mm optical path). 2 mg/ml 6-arm Polyetheylene Glycol-Amine (Sunbio Inc.) was added into GO—COOH suspension and sonicated for 5 min. N-(3-Dimethylaminopropyl-N'-ethylcarbodiimide hydrochloride (EDC, from Sigma Inc.) was added twice to reach 4 mM and reacted overnight, then quenched by Mercaptoethanol (Fluka Inc.). The final product (NGO-PEG) was obtained by ultracentrifugation at 45 k rpm in 2× phosphate buffered saline (PBS) for 1 h to save the supernatant (yield ~50%). The aggregates were discarded.

Rate separation in step density was used for NGO-PEG separation. In a typical experiment, OptiPrep® (60% (w/v) iodixanol, 1.32 g·cm-3) (Sigma-Aldrich Inc.) was diluted with water to make 5%, 10%, 15%, and 20% iodixanol solutions. Gradients were created directly in Beckman centrifuge tubes (polycarbonate, inner diameter 13 mm, length 51 mm) by adding the 4 layers (0.6 ml each) to the tube in order of increasing density. Finally, 0.4 mL of 60% iodixanol was added to the bottom of the centrifuge tube to raise the height of the gradient in the centrifuge tube. 0.2 mL freshly made GO-6PEG was immediately layered on top of density gradient prior to ultracentrifugation. The typical centrifugation condition was 2.5 h at 50 k RPM (~300 kg). Calibrated micropipettors were used to manually sample 100 μL fractions along the centrifuge tube after ultracentrifugation.

Grafting of PEG

Upon grafting PEG stars (6-arm branched PEG molecules) onto the —COOH groups, we obtained a product (NGO-PEG) with high solubility and stability in salt and cellular solutions, which is desirable for biological applications. Without pegylation, GO and GO—COOH suspensions immediately aggregated in salt and any other biological solutions. Atomic force microscopy (AFM) observed mostly <20 nm in sheet size of NGO-PEG, while the as-made GO sheets were 10-300 nm in size. The ultra-small size of the NGO was caused by sonication involved in GO—COOH making and PEGylation steps. IR characterization on carefully purified NGO-PEG sample indicated strong —CH2- (2870 cm-1) vibrations due to PEG chains, and characteristic amide-carbonyl (NH—CO) stretching vibration (~1650 cm-1, consistent with the grafting of PEG molecules on NGO sheets.

Chemical activation and PEGylation steps reduced the GO sheet size and changed the chemical functional groups on the sheets, as evidenced by shift in fluorescence emission maximum blue-shifted to about 520 nm. Photoluminescence (PL) of both GO and NGO-PEG was also observed in the IR and NIR regions.

A density gradient ultracentrifugation method was used to separate the NGO-PEG sheets by size and gain insight to the photoluminescence properties of NGO. By making use of the different sedimentation rate of different sized graphene in a density gradient, and by terminating the sedimentation at suitable time points, we captured different sized graphene sheets at different positions along the centrifuge-tube. AFM of different fractions clearly indicated size separation of NGO-PEG sheets by our method. Surprisingly, the different sized NGO sheets exhibited similar optical absorbance, photoluminescence and PLE spectra, without apparent quantum confinement effects expected due to the different physical sizes of the separated NGO sheets.

This unexpected result suggested that small, conjugated aromatic domains existed on a NGO sheet. That is, small conjugated domains with various sizes (~1-5 nm) coexist in a single, physically connected NGO sheet. Indeed, careful AFM imaging found small domain-like structures 1-5 nm in size. Separation of NGO sheets by physical size afforded various fractions exhibiting similar photoluminescence since the NGO-PEG sheets contained similar smaller aromatic domains. The domain sizes were inhomogeneous and ranged from small aromatic molecules to large macromolecular domains. The former was responsible for fluorescence in the visible range, while the latter gave PL in IR range. Fluorescent species in the NIR and IR range are potentially useful for biological applications since cells and tissues exhibit little autofluorescence in this region.

Antibody Conjugation and Imaging

We covalently conjugated a B-cell specific antibody, Rituxan® rituximab (anti-CD20) to NGO-PEG (NGO-PEG-rituximab) to selectively recognize and bind to B cell lymphoma cells. We incubated B-cells and T-cells in solutions of NGO-PEG-rituximab conjugates at 4° C. to allow the conjugates to interact with the cell surface but block internalization via endocytosis. The cells were then washed and imaged by detecting NIR photoluminescence from 1100 to 2200 nm using an InGaAs detector under 658 nm excitation (laser spot size ~1 μm). We detected the intrinsic NIR photoluminescence of NGO-PEG selectively on positive Raji B-cells surface and not on negative CEM T-cells. This confirmed selective NGO-PEG-Ab binding to B-cells over T cells. It also established NGO as novel NIR fluorophores for selective biological detections and imaging with the advantage of little or no cellular autofluorescence in IR region. As a result, NGO-PEG as NIR fluorescent tags may allow for highly sensitive detection of low expression levels of cell surface proteins, which could be valuable to various biological and medical applications such as disease diagnosis at single cell level. Another advantage of the NGO-PEG fluorophores is the lack of photobleaching due to the robust graphene structure. No noticeable decay or loss of photoluminescence intensity was observed under hours of laser excitation. Nevertheless, the fluorescence quantum yield (QY) in the NIR-IR region appeared low. In our control experiments, we found that the QY of GO is similar to single-walled carbon nanotubes (SWNTs), which is on the order of a few percent.

Thiolated Rituxan® was conjugated to the amine groups on NGO-PEG via a sulfo-SMCC linker (Pierce Inc.). For the cell incubation, 200 μl of CEM.NK T-cell and Raji B-cell (~1 million/ml) were incubated with 50 μl of NGO-PEG with or without Rituxan conjugation in PBS for 1 h at 4° C. The NGO-PEG concentration in the solution during incubation was ~0.7 mg/ml. Cells were washed with PBS 3 times to remove unbound NGO-PEG before use for NIR photoluminescence imaging. Cell samples prepared as described above were placed in a sample holder with a thin 200 μm quartz window. All NIR fluorescence images were taken using an inverted NIR fluorescence microscope in confocal mode. Excitation from a diode laser at 658 nm (Renishaw) was focused using a 100×IR coated objected lens (Olympus). The laser spot size width on the sample was about 1 μm FWHM. The laser intensity at the sample was ~20 mW. Emitted light was collected through the same objective and focused onto an OMA-V 1024 element linear InGaAs array (Princeton Instruments). The collected light went through a 900 nm long pass filter (Omega) and a 1100 nm long pass filter (ThorLabs) to block reflected excitation and reduce background fluorescence from the sample holder. High resolution images were taken by inserting a 50 μm pinhole in the collection path, and 1 micron steps were taken in 2 directions. Background fluorescence from the sample holder (~160 counts) was subtracted to give relevant statistics about the effectiveness of NGO-PEG binding.

Addition of Doxorubicin

Figure 32:
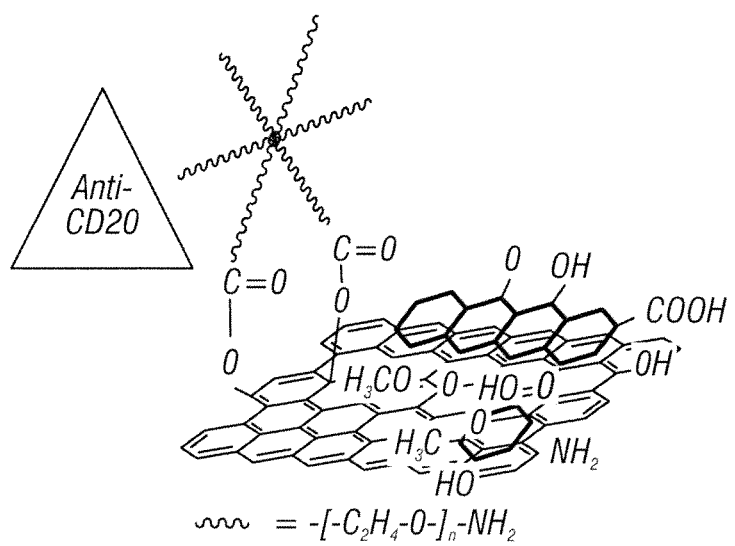
FIG. 32 is a schematic drawing showing the nanographene oxide of the preceding figure attached to doxorubicin (DOC) by supramolecular bonding, as well as Rituxan® (rituximab) which is linked to the PEG.

Next, we explored using NGO as sheet-like vehicles to transport an aromatic anticancer drug doxorubicin (DOX) into cancer cells. Rituximab conjugated NGO-PEG was used to target specific cancer cells for selective cellular killing. FIG. 32 illustrates schematically the NGO with rituximab as described above, plus DOX adsorbed to the NGO. In FIG. 32, the anti-CD 20 is covalently attached to an arm of a branched PEG; the PEG is linked to a carboxyl group linked through an ether linkage to the graphene sheet; and the loading of DOX, a widely used chemotherapy drug for treating various cancers, was performed by simple mixing of a NGO-PEG-Ab solution with DOX at pH 8 overnight, followed by repeated filtering to remove free, unbound DOX in solution. The formation of NGO-PEG/DOX was visible by the reddish color of the NGO-PEG/DOX solutions due to adsorbed DOX and its characteristic UV-vis absorbance peak at 490 nm on top of the NGO-PEG absorption spectrum. On the basis of optical absorbance data and molar extinction coefficients of DOX and NGO-PEG we estimated, a high weight ratio of ~3:1 between DOX and graphitic carbon in NGO-PEG can be reached. The loading of DOX onto NGO was attributed to simple π-stacking, similar to that in carbon nanotubes described in the previous examples. Under AFM, an obvious thickness increase was observed as DOX was stacked onto graphene sheets.

Doxorubicin (DOX) loading onto NGO-PEG (and NGO-PEG-Rituxan) was done by simply mixing 0.5 mM of DOX with the NGO-PEG solution (~0.2 mg/ml) at pH 8 overnight. Unbound excess DOX was removed by filtration through a 100 kDa filter and repeated rinse. The formed NGO-PEG/DOX complexes were re-suspended and stored at 4° C. Concentration of DOX loaded onto NGO-PEG was measured by the absorbance peak at 490 nm (characteristic of DOX, after subtracting the absorbance of NGO-PEG at that wavelength) with a molar extinction coefficient of $1.05 \times 10^4$ M·cm-1. Both Raji and CEM cells were incubated with free DOX, NGO-PEG/DOX, NGO-PEG/DOX+Rituxan (unconjugated) and NGO-PEG-Ri/DOX at DOX concentrations of 2 μM or 10 μM for 2 hours and washed by PBS twice before transferring into fresh cell medium. After another 48 h incubation, Cell viability was measured by the MTS assay with CellTiter96 kit (Promega).

Drug Release

Drug release from NGO-PEG sheets was observed as the chemical environment changed to neutral or acidic condition.

We found that ~40% of DOX loaded on NGO-PEG was released over 1 day in an acidic solution of pH 5.5, which was attributed to the increased hydrophilicity and solubility of DOX at this pH. The release rate was slowed down as the pH was adjusted to pH 7.4, ~15% over 2 days. The pH-dependent drug release from NGO-PEG could be exploited for drug delivery applications since the micro-environments in the extracellular tissues of tumors and intracellular lysosomes and endosomes are acidic, which will afford active drug release from NGO-PEG delivery vehicles.

Figure 33:
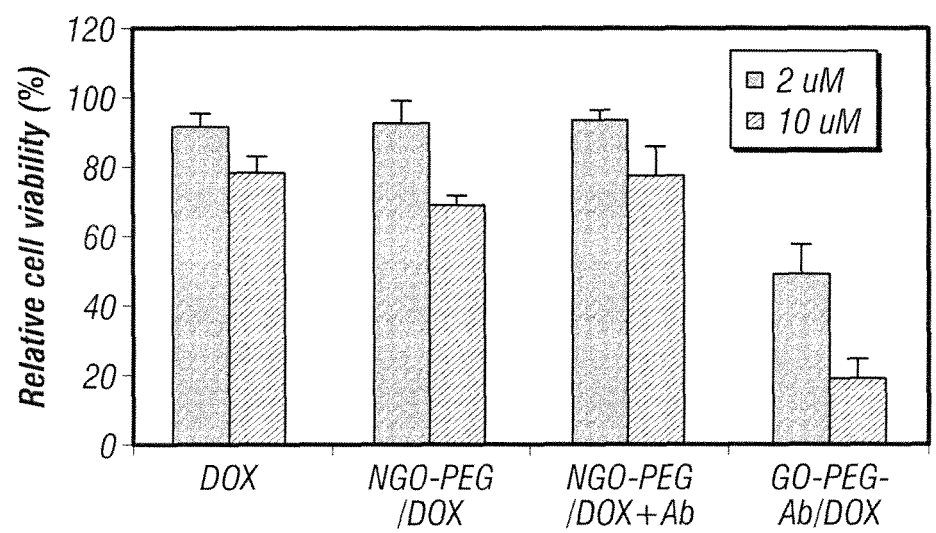
FIG. 33 is a bar graph showing results of an in vitro toxicity test at 2 µM and 10 µM DOX concentration to show Rituxan selectively enhanced doxorubicin delivery into Raji B-cells by comparing NGO-PEG-Rituxan/DOX with free DOX, mixture of DOX with NGO-PEG, and mixture of DOX, Rituxan and NGO-PEG. The viable cell percentage was measured by the MTS assay.

For DOX loaded onto NGO-PEG-rituximab, we incubated the conjugates with Raji cells at 2 uM and 10 uM DOX concentrations. Much enhanced DOX delivery and cell killing was evidenced by comparison with Raji cells treated by free DOX, NGO-PEG/DOX without rituximab, and a mixture of NGO-PEG/DOX and rituximab without covalent binding (FIG. 33). This clearly demonstrated selective killing of cancer cells using NGO-PEG-antibody/drug conjugates in vitro.

In summary, multifunctional biocompatible nano-graphene oxides with various physical sizes were prepared in a highly scalable and low cost manner. Photoluminescence of NGO from visible through infrared range was revealed and used for cellular imaging. Anti cancer drug was loaded onto NGO with ultrahigh capacity, and selectively transported into specific cancer cells by antibody guided targeting. The novel graphitic nanostructures, combined with multi-functionalities including biocompatibility, photoluminescence and drug loading, suggest promising applications of graphene materials in biological and medical areas.

CONCLUSION

The above specific description is meant to exemplify and illustrate the invention and should not be seen as limiting the scope of the invention, which is defined by the literal and equivalent scope of the appended claims. Any patents or publications mentioned in this specification are indicative of levels of those skilled in the art to which the patent or publication pertains as of its date and are intended to convey details of the invention which may not be explicitly set out but which would be understood by workers in the field. Such patents or publications are hereby incorporated by reference to the same extent as if each was specifically and individually incorporated by reference, as needed for the purpose of describing and enabling the method or material referred to.

REFERENCES

1. Britz, D. A.; Khlobystov, A. N., *Chem. Soc. Rev.* 2006, 35, (7), 637.
2. Kam, N. W. S.; Jessop, T. C.; Wender, P. A.; Dai, H. J., *J. Am. Chem. Soc.* 2004, 126, 6850-6851.
3. Liu, Z.; Cai, W. B.; He, L. N.; Nakayama, N.; Chen, K.; Sun, X. M.; Chen, X. Y.; Dai, H. J., *Nature Nanotech.* 2007, 2, (1), 47-52.
4. Cherukuri, P.; Bachilo, S. M.; Litovsky, S. H.; Weisman, R. B., *J. Am. Chem. Soc.* 2004, 126, (48), 15638-15639.
5. Bianco, A.; Kostarelos, K.; Partidos, C. D.; Prato, M., *Chem. Commun.* 2005, (5), 571-577.
6. Herranz, M. A.; Martin, N.; Campidelli, S. P.; Prato, M.; Brehm, G.; Guldi, D. M., *Angew. Chem. Int. Ed.* 2006, 45, (27), 4478-4482.
7. Kam, N. W. S.; Liu, Z.; Dai, H., *J. Am. Chem. Soc.* 2005, 127, (36), 12492-12493.
8. Banerjee, S.; Hemraj-Benny, T.; Wong, S. S., *Advanced Materials* 2005, 17, (1), 17.
9. Chen, R.; Zhang, Y.; Wang, D.; Dai, H., *J. Am. Chem. Soc.* 2001, 123.
10. Nakayama-Ratchford, N.; Bangsaruntip, S.; Sun, X.; Welsher, K.; Dai, H., *J. Am. Chem. Soc.* 2007, 129, 2448-2449.
11. Chen, J.; Hammon, M. A.; Hu, H.; Chen, Y. S.; Rao, A. M.; Eklund, P. C.; Haddon, R. C., *Science* 1998, 282, 95-98.
12. Storm, G.; ten Kate, M. T.; Working, P. K.; Bakker-Woudenberg, I. A. J. M., *Clin. Cancer Res.* 1998, 4, (1), 111.
13. Lee, C. C.; Gillies, E. R.; Fox, M. E.; Guillaudeu, S. J.; Frechet, J. M. J.; Dy, E. E.; Szoka, F. C., *Proc. Nat. Aca. Sci. USA* 2006, 103, (45), 16649.

What is claimed is:

1. A dispersed nanoparticle complex in a stable suspension for delivery of active agents into a cell, comprising:
   (a) a nanoparticle having an extended aromatic structure on its surface;
   (b) hydrophilic polymers bound to the nanoparticle in sufficient numbers to render the nanoparticle soluble in said suspension; and
   (c) a plurality of small molecule active agents attached directly to the surface of the nanoparticle, wherein the small molecule active agents comprise a fused aromatic ring structure, directly attached to the surface of the nanoparticle through supramolecular bonding, said bonding being reversible $\pi$ stacking between said fused aromatic ring structure and said extended aromatic structure on the nanoparticle.

2. The nanoparticle complex of claim 1 wherein the nanoparticle is a carbon nanotube.

3. The nanoparticle complex of claim 2 wherein the carbon nanotube is an SWNT.

4. The nanoparticle complex of claim 1 wherein the nanoparticle comprises boron nitride.

5. The nanoparticle complex of claim 1 wherein the nanoparticle comprises a graphitic surface.

6. The nanoparticle complex of claim 5 wherein the nanoparticle comprises a graphene sheet.

7. The nanoparticle complex of claim 6 wherein the nanoparticle is graphitic oxide, the hydrophilic polymers are covalently bonded to the graphitic oxide, and the agents are bonded to the graphitic oxide through supramolecular bonding.

8. The nanoparticle complex of claim 6 wherein the graphene sheet is a pristine single layer graphene sheet.

9. The nanoparticle complex of claim 5 wherein the nanoparticle is either (i) a coated nanocrystal, (ii) a nanotube, or (iii) a graphene sheet.

10. The nanoparticle complex of claim 5 wherein the nanoparticle is a graphitic coated metal core.

11. The nanoparticle complex of claim 10 wherein the metal core is a nanocrystal and the graphitic coat is a single layer.

12. The nanoparticle complex of claim 11 wherein the nanocrystal comprises FeCo or Au.

13. The nanoparticle complex of claim 1 wherein the nanoparticle has an average length of 50-500 nm.

14. The nanoparticle complex of claim 1 wherein the nanoparticle is an SWNT having a diameter of between 1 and 2 nm prior to functionalization.

15. The nanoparticle complex of claim 1 wherein the hydrophilic polymers comprise PEG and the PEG is from 10 to 500 polyethylene oxide units.

16. The nanoparticle complex of claim 15 wherein the PEG is amine-terminated.

17. The nanoparticle complex of claim 1 where the hydrophilic polymers comprise two to seven branches.

18. The nanoparticle complex of claim 17 wherein the hydrophilic polymers have four to six branches.

19. The nanoparticle complex of claim 18 comprising at least two drug molecules linked to different branches.

20. The nanoparticle complex of claim 19 wherein the drug molecules are linked to the hydrophilic polymers by a cleavable linkage.

21. The nanoparticle complex of claim 17 wherein the hydrophilic polymers are PEG.

22. The nanoparticle complex of claim 17 wherein the hydrophilic polymers are dextran.

23. The nanoparticle complex of claim 21 wherein the hydrophilic polymers are further linked to a targeting agent.

24. The nanoparticle complex of claim 23 wherein the targeting agent is an RGD peptide.

25. The nanoparticle complex of claim 23 where the targeting agent is an antibody.

26. The nanoparticle complex of claim 1 wherein the hydrophilic polymers are covalently bound to the nanoparticle.

27. The nanoparticle complex of claim 1 wherein the hydrophilic polymers are noncovalently bound to the nanoparticle.

28. The nanoparticle complex of claim 1 wherein the hydrophilic polymers are comprised of an organic amphiphilic molecule.

29. The nanoparticle complex of claim 28 wherein the organic amphiphilic molecule comprises a polar lipid adsorbed on the nanoparticle through supramolecular hydrophobic bonding.

30. The nanoparticle complex of claim 29 wherein the polar lipid is a phospholipid.

31. The nanoparticle complex of claim 1 wherein the hydrophilic polymers are bound to the nanoparticle by a lipid portion linked to the hydrophilic polymers.

32. The nanoparticle complex of claim 1, wherein said small molecule active agents are selected from the group consisting of: doxorubicin (DOX), 7-Ethyl-10-hydroxy-camptothecin (SN38), daunorubicin, paclitaxel (PTX), toxorubicin, vinca-alcaloide, actionmycin, toposites, tamoxifen, cisplatin, carboplatin and satraplatin.

33. The nanoparticle complex of claim 1 wherein the active agents are small molecule drugs.

34. The nanoparticle complex of claim 33 wherein said small molecule drugs are anti-cancer drugs.

35. The nanoparticle complex of claim 1 wherein the active agents are hydrophobic small molecules bonded to a surface of the nanoparticle.

36. The nanoparticle complex of claim 1 wherein the active agents are linked to the hydrophilic polymers by a cleavable linkage.

37. The nanoparticle complex of claim 20 wherein the cleavable linkage is a linkage which is one of hydrazone, ester or disulfide.

38. The nanoparticle complex of claim 1 wherein the active agents are selected from the group consisting of doxorubicin, camptothecin, daunorubicin, fluorescein and paclitaxel.

39. The nanoparticle complex of claim 1 where 1-40% of the nanoparticle surface area is complexed with the hydrophilic polymers and 30-95% is complexed with the active agents.

40. A preparation of the nanoparticle complex of claim 1 in an aqueous suspension.

41. A preparation of the nanoparticle complex of claim 1 in unit dosage form.

42. The nanoparticle complex of claim 1 wherein the hydrophilic polymers are branched.

43. A nanoparticle complex for delivery of at least two different active agents into a cell, comprising:
    (a) a nanoparticle having an extended aromatic structure on its surface;
    (b) hydrophilic polymers bound to the nanoparticle by supramolecular bonding;
    (c) a first active agent coupled to the hydrophilic polymers; and
    (d) a plurality of second active agents, comprising a fused aromatic ring structure, directly bonded to the nanoparticle through supramolecular bonding
        wherein said nanoparticle complex is as defined in claim 1.

44. The complex of claim 43 where the second active agents are small molecules having fused aromatic rings and the supramolecular bonding is by pi stacking.

45. A method for preparing a nanoparticle complex for delivery of active agents inside a cell, comprising the steps of:
    (a) obtaining a nanoparticle, which has an extended aromatic surface, in dispersed form;
    (b) attaching a hydrophilic polymer to the nanoparticle;
    (c) attaching through supramolecular bonding an active agent to the surface of the nanoparticle; and
    (d) forming a stable aqueous suspension of the nanoparticle complex wherein said nanoparticle complex is as defined in claim 1.

46. A method for delivering delivery of active agents inside a cell, wherein said active agents are in a complex comprising:
    a nanoparticle having an extended aromatic structure on its surface;
    hydrophilic polymers bound to the nanoparticle; and
        small molecule active agents, comprising a fused aromatic ring structure, directly attached to the surface of the nanoparticle through supramolecular bonding wherein said nanoparticle complex is as defined in claim 1,
    comprising the step of:
        contacting the cell with the complex for a time sufficient to allow internalization of the complex by the cell.

47. The method of claim 46 wherein the hydrophilic polymers further comprise a targeting agent for delivering the active agents to a cell type providing a target for the targeting agent.

48. The method of claim 46 wherein the adsorbed active agents are more dissociated at low pH.

49. The method of claim 46 comprising the step of contacting the complex with serum, whereby the complex does not dissociate in serum.

50. The method of claim 46 where the active agents are an anti-cancer drug.

51. The method of claim 46 where the active agents are hydrophobic.

* * * * *

UNITED STATES PATENT AND TRADEMARK OFFICE
CERTIFICATE OF CORRECTION

| | | Page 1 of 1 |
|---|---|---|
| PATENT NO. | : 8,535,726 B2 | |
| APPLICATION NO. | : 12/178891 | |
| DATED | : September 17, 2013 | |
| INVENTOR(S) | : Dai et al. | |

It is certified that error appears in the above-identified patent and that said Letters Patent is hereby corrected as shown below:

In the specification

Please replace Column 1, lines 12-16 with:

--STATEMENT OF GOVERNMENT SUPPORT

This invention was made with Government support under contract CA119367 awarded by the National Institutes of Health. The Government has certain rights in the invention.--

Signed and Sealed this
Fifth Day of April, 2016

Michelle K. Lee
*Director of the United States Patent and Trademark Office*